(12) United States Patent
Evans et al.

(10) Patent No.: US 11,708,574 B2
(45) Date of Patent: Jul. 25, 2023

(54) NUCLEIC ACID SEQUENCING ADAPTERS AND USES THEREOF

(71) Applicant: Myriad Women's Health, Inc., South San Francisco, CA (US)

(72) Inventors: Eric Andrew Evans, Brisbane, CA (US); Imran Saeedul Haque, San Francisco, CA (US); Kyle Beauchamp, San Francisco, CA (US); Clement Chu, South San Francisco, CA (US); Carlo G. Artieri, San Bruno, CA (US); Noah Welker, Half Moon Bay, CA (US)

(73) Assignee: Myriad Women's Health, Inc., South San Francisco, CA (US)

( * ) Notice: Subject to any disclaimer, the term of this patent is extended or adjusted under 35 U.S.C. 154(b) by 79 days.

(21) Appl. No.: 15/619,078

(22) Filed: Jun. 9, 2017

(65) Prior Publication Data

US 2017/0355984 A1    Dec. 14, 2017

Related U.S. Application Data

(60) Provisional application No. 62/447,784, filed on Jan. 18, 2017, provisional application No. 62/364,256, (Continued)

(51) Int. Cl.
  *C12N 15/10*  (2006.01)
  *C12Q 1/6869*  (2018.01)
  (Continued)

(52) U.S. Cl.
  CPC ....... *C12N 15/1093* (2013.01); *C12N 9/1252* (2013.01); *C12Q 1/6806* (2013.01);
  (Continued)

(58) Field of Classification Search
  CPC .............. C12N 15/1093; C12Q 1/6806; C12Q 2525/191
  See application file for complete search history.

(56) References Cited

U.S. PATENT DOCUMENTS

| 5,476,930 A | 12/1995 | Letsinger |
| 5,695,937 A | 12/1997 | Kinzler |

(Continued)

FOREIGN PATENT DOCUMENTS

| CN | 104232626 A | * 12/2014 |
| WO | 2010151842 A2 | 12/2010 |

(Continued)

OTHER PUBLICATIONS

Schmitt (Proceedings National Academy of Sciences (2012) pp. 1-6).*

(Continued)

*Primary Examiner* — Joseph G. Dauner
(74) *Attorney, Agent, or Firm* — Foley & Lardner LLP

(57) ABSTRACT

High-fidelity, high-throughput nucleic acid sequencing enables healthcare practitioners and patients to gain insight into genetic variants and potential health risks. However, previous methods of nucleic acid sequencing often introduces sequencing errors (for example, mutations that arise during the preparation of a nucleic acid library, during amplification, or sequencing). Provided herein are sequencing adapters comprising a nondegenerate or variable length molecular barcode and compositions comprising a plurality of sequencing adapters, which can be useful for sequencing nucleic acids. Further provided are methods of using the sequencing adapters, including methods of sequencing nucleic acids, methods of identifying an error in a nucleic acid sequence, and methods of determining the number of nucleic acid molecules in a library.

19 Claims, 19 Drawing Sheets

Related U.S. Application Data filed on Jul. 19, 2016, provisional application No. 62/348,791, filed on Jun. 10, 2016.

(51) Int. Cl.

| | |
|---|---|
| *C12Q 1/6806* | (2018.01) |
| *C12N 9/12* | (2006.01) |
| *C12Q 1/6832* | (2018.01) |
| *C12P 19/34* | (2006.01) |

(52) U.S. Cl.
CPC ......... *C12Q 1/6832* (2013.01); *C12Q 1/6869* (2013.01); *C12N 15/10* (2013.01); *C12P 19/34* (2013.01); *C12Q 2525/191* (2013.01); *C12Q 2527/107* (2013.01); *C12Q 2563/179* (2013.01); *C12Y 207/07007* (2013.01)

(56) References Cited

U.S. PATENT DOCUMENTS

| | | | |
|---|---|---|---|
| 5,780,613 A | 7/1998 | Letsinger | |
| 6,258,540 B1 | 7/2001 | Lo | |
| 7,109,178 B2 | 9/2006 | Ji | |
| 7,115,400 B1 | 10/2006 | Adessi | |
| 7,332,277 B2 | 2/2008 | Dhallan | |
| 7,799,531 B2 | 9/2010 | Mitchell | |
| 8,383,338 B2 | 2/2013 | Kitzman | |
| 9,092,401 B2 | 7/2015 | Richards | |
| 9,309,556 B2 | 4/2016 | Myllykangas | |
| 9,476,095 B2 | 10/2016 | Vogelstein | |
| 10,752,946 B2 | 8/2020 | Chu | |
| 2005/0164241 A1 | 7/2005 | Hahn | |
| 2007/0134658 A1 | 6/2007 | Bohmer | |
| 2008/0160580 A1 | 7/2008 | Adessi | |
| 2008/0286795 A1 | 11/2008 | Kawashima | |
| 2009/0136938 A1* | 5/2009 | Tao | G16B 30/00 435/6.11 |
| 2010/0022406 A1 | 1/2010 | Srinivasan | |
| 2011/0319290 A1* | 12/2011 | Raymond | C12Q 1/6869 506/9 |
| 2012/0058468 A1 | 3/2012 | McKeown | |
| 2012/0295819 A1 | 11/2012 | Leamon | |
| 2013/0157870 A1* | 6/2013 | Pushkarev | C12Q 1/6874 506/2 |
| 2013/0171185 A1 | 7/2013 | Settembre | |
| 2013/0261019 A1 | 10/2013 | Lin | |
| 2013/0298265 A1 | 11/2013 | Cunnac | |
| 2014/0024536 A1 | 1/2014 | Richards | |
| 2014/0024541 A1 | 1/2014 | Richards | |
| 2014/0121116 A1 | 5/2014 | Richards | |
| 2014/0141982 A1 | 5/2014 | Jacobson | |
| 2014/0162278 A1 | 6/2014 | Richards | |
| 2014/0180594 A1 | 6/2014 | Kim | |
| 2014/0274740 A1 | 9/2014 | Srinivasan | |
| 2015/0017635 A1 | 1/2015 | Myllykangas | |
| 2015/0044687 A1 | 2/2015 | Schmitt | |
| 2015/0080266 A1 | 3/2015 | Volkmuth | |
| 2015/0197798 A1 | 7/2015 | Xu | |
| 2015/0205914 A1 | 7/2015 | Richards | |
| 2015/0275289 A1 | 10/2015 | Otwinokowski | |
| 2015/0284712 A1 | 10/2015 | Kurihara | |
| 2015/0353926 A1 | 12/2015 | Rigatti | |
| 2015/0361492 A1 | 12/2015 | Vogelstein | |
| 2016/0068903 A1 | 3/2016 | Zhou | |
| 2016/0115544 A1 | 4/2016 | Elzinga | |
| 2016/0319345 A1 | 11/2016 | Gnerre | |
| 2017/0321270 A1 | 11/2017 | Hague | |
| 2017/0355984 A1 | 12/2017 | Evans | |
| 2018/0089364 A1 | 3/2018 | Muzzey | |
| 2018/0201994 A1 | 7/2018 | Beauchamp | |
| 2018/0216103 A1 | 8/2018 | Lai | |
| 2018/0216176 A1 | 8/2018 | Chu | |
| 2018/0237837 A1 | 8/2018 | Osborne | |

FOREIGN PATENT DOCUMENTS

| | | |
|---|---|---|
| WO | 2012003374 A2 | 1/2012 |
| WO | 2012040387 | 3/2012 |
| WO | 2012078792 | 6/2012 |
| WO | 2012088456 | 6/2012 |
| WO | 2013112923 A1 | 8/2013 |
| WO | 2013142389 | 9/2013 |
| WO | 2014144495 A1 | 9/2014 |
| WO | 2016010856 A1 | 1/2016 |
| WO | 2016130704 A2 | 8/2016 |
| WO | 2017037657 A1 | 3/2017 |
| WO | 2018144216 A1 | 8/2018 |
| WO | 2018144217 A1 | 8/2018 |

OTHER PUBLICATIONS

Sehnert (Clinical Chemistry (2011) vol. 57, pp. 1-8).*
MacLean (Nature Reviews Microbiology (2009) vol. 7, pp. 287-296).*
Wong (.Current Protocols in Molecular Biology 7.11.1-7.11.11, Jan. 2013).*
Nikooienejad( 2012 IEEE International Workshop on Genomic Signal Processing and Statistics (GENSIPS) Dec. 2-4, 2012, Washington, DC, USA, pp. 26-30).*
Gundmundsson et al., "Genome-wide association and replication studies identify four variants associated with prostate cancer susceptibility", Nat Genet, 41:1122-1126, 2009.
Illumina, Calculating Percent Passing Filter for Patterned and Nonpatterned Flow Cells, Pub. No. 770-2014-043-B, 2017.
Illumina, Quality Scores for Next Generation Sequencing, Pub. No. 770-2011-030, Oct. 31, 2011.
Illumina, Understanding Illumina Quality Scores, Pub. No. 770-2012-058, Apr. 23, 2014.
International Preliminary Report on Patentability dated Aug. 15, 2019 in PCT/US2018/013959 (10 pages).
International Search Report and Written Opinion issued in PCT/US2018/020744 dated May 10, 2018 (4 pages).
Kircher et al. , "Double indexing overcomes inaccuracies in multiplex sequencing on the Illumina platform", Supplementary pp. 1-17. Nucleic acids research. Jan. 1, 2012; 40(1):e3 pp. 1-8. (Year: 2012).
Kircher et al., "Double indexing overcomes inaccuracies in multiplex sequencing on the Illumina platform", Nucleic acids research. Jan. 1, 2012; 40(1):e3 pp. 1-8. (Year: 2012).
Knapp et al., "Generating barcoded libraries for multiplex high-throughput sequencing", Methods Mol Biol., 2012, 840:155-70. doi: 10.1007/978-1-61779-516-9_19.
Kozich et al., "Development of a dual-index sequencing strategy and curation pipeline for analyzing amplicon sequence data on the MiSeq Illumina sequencing platform.", Appl. Environ. Microbiol. , Sep. 1, 2013; 79(17):5112-20. (Year: 2013).
Lovett , Susan T., "The DNA Exonucleases of *Escherichia coli*", EcoSal Plus. Dec. 2011;4(2):10.1128/ecosalplus.4.4.7. doi: 10.1128/ecosalplus.4.4.7.
Meyer et al., "Illumina sequencing library preparation for highly multiplexed target capture and sequencing", Cold Spring Harb Protoc., Jun. 2010;2010(6):pdb.prot5448. doi: 10.1101/pdb.prot5448.
Murgha, Yusuf Esmai, "Large-Scale Generation of Synthetic DNA Libraries: Sequence-Specific Priming of Reverse Transcription", PhD diss., 2012.
Nikiforov et al, "The use of phosphorothioate primers and exonuclease hydrolysis for the preparation of single-stranded PCR products and their detection by solid-phase hybridization", Genome Research. Apr. 1, 1994; 3(5): 285-91. (Year: 1994).
Peng et al., "Reducing amplification artifacts in high multiplex amplicon sequencing by using molecular barcodes", BMC genomics. Dec. 2015; 16(1):589 pp. 1-12.
Samorodnitsky et al. "Comparison of custom capture for targeted next-generation DNA sequencing," J Mol Diagn, Jan. 1, 2015 (Jan. 1, 2015), vol. 17, pp. 64-75.

(56) References Cited

OTHER PUBLICATIONS

Turner et al., "Massively parallel exon capture and library-free resequencing across 16 genomes", Nat. Methods, 6:315-316, 2009.
Biomek, BiomekTips and Labware, Beckman Coulter, 2012, 1-24. (Year: 2012).
Kammerer, et al., Oligonucleotide Modifications: Choosing the Right Mod For Your Needs, Integrated DNA Technologies, 2012, 1-5. Obtained online at:https://www.idtdna.com/pages/education/decoded/article/choosing-the-right-mod-for-your-needs on Aug. 25, 2021. (Year: 2012).
Neb, Restriction Enzyme Digestion Products, New England Biolabs, 2021, 1-9. Obtained online at: https://www.neb.com/ plications/cloning-and-synthetic-biology/dna-preparation/restriction-enzyme-digestion/products on Aug. 25, 2021. (Year: 2021).
Ahn, J. et al., "Asymmetrical barcode adapter assisted recovery of duplicate reads and error correction strategy to detect rare mutations in circulating tumor DNA", Nature, (May 2, 2017), vol. 7, No. 46678, pp. 1-9, XP055455428.
Allhoff, M. et al. (2013). "Discovering motifs that Induce Sequencing Errors," BMC Bioinformatics 14(Suppl. 5):S1, pp. 1-10.
Alnemri, E.S., et al., Activation of Internucleosomal DNA Cleavage in Human CEM Lymphcytes by Glucocorticoid and Novobiocin, J. Biol. Chem., 1990, 265(28): 17323-17333.
Altschul, S.F., et al., Basic Local Alignment Search Tool, 1990, J. Mol. Biol. 215:403-410.
Arbeithuber, B. et al. (Jul. 31, 2016). "Artifactual Mutations Resulting from DNA Lesions Limit Detection Levels in Ultrasensitive Sequencing Applications," DNA Res. 23(6):547-559.
Casbon, J.A. et al. (Jul. 2011; e-published on Apr. 13, 2011). "A Method for Counting PCR Template Molecules With Application to Next-Generation Sequencing," Nucleic Acids Res. 39(12):e81, pp. 1-8.
Chen, L. et al. (Feb. 17, 2017). "DNA Damage is a Pervasive Cause of Sequencing Errors, Directly Confounding Variant Identification," Science 355:752-756, (with supplementary material), twenty eight pages.
Cibulskis, K. et al. (Mar. 2013; e-published on Feb. 10, 2013). "Sensitive Detection of Somatic Point Mutations in Impure and Heterogeneous Cancer Samples," Nat. Biotechnol. 31(3):213-219, twenty one pages.
Costello, M. et al. (Apr. 2013; e-published on Jan. 8, 2013). "Discovery and Characterization of Artifactual Mutations in Deep Coverage Targeted Capture Sequencing Data Due to Oxidative DNA Damage During Sample Preparation," Nucleic Acids Res. 41(6):e67, pp. 1-12.
De Vlaminck, I. et al. (Oct. 27, 2015; e-published on Oct. 12, 2015). "Noninvasive Monitoring of Infection and Rejection After Lung Transplantation," Proc. Natl. Acad. Sci. USA 112(43):13336-13341.
Fierer, N. et al. (Nov. 18, 2008). "The Influence of Sex, Handedness, and Washing on the Diversity of Hand Surface Bacteria," Proc. Nat'l Adad. Sci. 105(46):17994-17999.
Hamady, M. et al. (Mar. 2008). "Error-Correcting Barcoded Primers Allow Hundreds of Samples to by Pyrosequenced in Multiplex," Nature Methods 5(3):235-237, six pages, (with supplementary material), fifty three pages.
Henikoff, S., et al., Amino acid substitution matrices from protein blocks, Proc. Natl. Acad. Sci., 1992, 89:10915-10919.
Higgins, D.G., et al., CLUSTAL: a package for performing multiple sequence alignment on a microcomputer, Gene, 1998, 73:237-244.
Hopmans, E.S. et al. (Apr. 29, 2014). "A Programmable Method For Massively Parallel Targeted Sequencing," Nucleic Acids Res. 42(10):e88, pp. 1-16.
Horhota, A., et al., Glycerol Nucleoside Triphosphates: Synthesis and Polymerase Substrate Activities, Organic Letters, 2006, 8(23):5345-5347.
Hybridization capture of DNA libraries using xGen Lockdown Probes and Reagents, IDT Integrated DNA Technologies 2015.
Jabara, C.B. et al. (Dec. 13, 2011). "Accurate Sampling and Deep Sequencing of the HIV-1 Protease Gene Using a Primer ID," Proc. Natl. Acad. Sci. U.S.A. 108(50):20166-20171.
Karlin, S., et al., Applications and statistics for multiple high-scoring segments in molecular sequences, Proc. Natl. Acad. Sci., 1993, 90:5873-5877.
Kennedy, S.R. et al. (Nov. 2014; e-published on Oct. 9, 2014). "Detecting Ultralow-Frequency Mutations by Duplex Sequencing," Nat. Protoc. 9(11):2586-2606, forty pages.
Kinde, I. et al. (Jun. 7, 2011). "Detection and Quantification of Rare Mutations With Massively Parallel Sequencing," Proc. Natl. Acad. Sci. U.S.A. 108(23):9530-9535.
Krimmel, J.D. et al. (May 24, 2016; e-published on May 5, 2016). "Ultra-Deep Sequencing Detects Ovarian Cancer Cells In Peritoneal Fluid And Reveals Somatic TP53 Mutations In Noncancerous Tissues," Proc. Natl. Acad. Sci. U.S.A. 113(21):6005-6010.
Krishnan, A.R. et al. (Feb. 24, 2011). "Barcodes for DNA Sequencing With Guaranteed Error Correction and Capability," Electronics Letters 47(4):236-237.
Kunkel, T.A. (Apr. 23, 2004). "DNA Replication Fidelity," J. Biol. Chem. 279(17):16895-16898.
Lanman, R.B. et al. (Oct. 16, 2015). "Analytical and Clinical Validation of a Digital Sequencing Panel for Quantitative, Highly Accurate Evaluation of Cell-Free Circulating Tumor DNA," PLoS One 10:e0140712, pp. 1-27.
Lefrançois et al., Efficient yeast ChiP-Seq using multiplex short-read DNA sequencing, BMC Genomics, vol. 10, pp. 1-18 (2009).
Mardis, E., Next-Generation DNA Sequencing Methods, Annu Rev Genomics Hum Genet 9:387-402,2008.
Margulies, M., et al., Genome Sequencing in Open Microfabricated High Density Picoliter Reactors, Nature 437 7057):376-380, 2005.
Mertes, F. et al. (Nov. 2011; e-published on Nov. 26, 2011). "Targeted Enrichment of Genomic DNA Regions for Next-Generation Sequencing," Briefings in Functional Genomics 10(6):374-386.
Myllykangas, S. et al. (Nov. 2011; e-published on Oct. 23, 2011). "Efficient Targeted Resequencing of Human Germline and Cancer Genomes by Oligonucleotide-Selective Sequencing," Nat Biotechnol. 29(11):1024-1027.
Needleman, S.B. et al. (Mar. 1970). "A General Method Applicable to the Search for Similarities in the Amino Acid Sequence of Two Proteins," Journal of Molecular Biology 48(3):443-453.
Newman, A.M. (2016; e-published on Mar. 28, 2016). "Integrated Digital Error Suppression for Improved Detection of Circulating Tumor DNA," Nature Biotechnology 34:547-555 (includes Supplementary material).
NimbleGen Seq EZ Library SR Users Guide, Roche, 2014.
O'Roak, B.J. et al. (Dec. 21, 2012; e-published on Nov. 15, 2012). "Multiplex Targeted Sequencing Identifiers Recurrently Mutated Genes in Autism Spectrum Disorders," Science 338(6114):1619-1622, thirteen pages.
Pearson, W.R., et al., Improved tools for biological sequence comparison, Proc. Natl. Acad. Sci., 1988, 85:2444-2448.
Richards, O.C., et al., Chemical Mechanism of Sonic, Acid, Alkaline and Enzymic Degradation of DNA, J. Mol. Biol., 1965, 11:327-340.
Schirmer, M. et al. (Mar. 11, 2016). "Illumina Error Profiles: Resolving Fine-Scale Variation in Metagenomics Sequencing Data," BMC Bioinformatics 17:125, pp. 1-15.
Schmitt, M.W. et al. (May 2015; Apr. 6, 2015). "Sequencing Small Genomic Targets with High Efficiency and Extreme Accuracy," Nat. Methods 12(5):423-425, nine pages.
Schmitt, M.W. et al. (Sep. 4, 2012; e-published on Aug. 1, 2012). "Detection of Ultra-Rare Mutations by Next-Generation Sequencing," Proc. Natl. Acad. Sci. U.S.A. 109(36):14508-14513.
Schwarzenbach, H. et al. (Jun. 2011; e-published on May 12, 2011). "Cell-Free Nucleic Acids as Biomarkers in Cancer Patients," Nature Reviews Cancer 11(6):426-437.
Soni, G., et al., Progress toward Ultrafast DNA Sequencing Using Solid-State Nanopores, Clin Chem 53:1996-2001, 2007.
Talevich, E. et al. (Apr. 21, 2016). "CNVkit: Genome-Wide Copy Number Detection and Visualization from Targeted DNA Sequencing," PLoS Comput. Biol. 12(4):e1004873, pp. 1-18.
Travers, K.J. et al. (2010; e-published on Jun. 22, 2010). "A Flexible and Efficient Template Format for Circular Consensus Sequencing and SNP Detection," Nucleic Acids Research 38(15):e159, pp. 1-8.

(56) References Cited

OTHER PUBLICATIONS

Troutt, A., et al., Ligation-anchored PCR: A simple amplification technique with single-sided specificity, Proc Natl Acad Sci USA 89:9823-9825, 1992.

Zhong, S. et al. (2011). "High-Throughput Illumina Strand-Specific RNA Sequencing Library Preparation," Cold Spring Harbor Protocols 2011(8):940-949.

Zimmermann, B. et al. (Dec. 2012; e-published on Oct. 30, 2012). "Noninvasive Prenatal Aneuploidy Testing of Chromosomes 13, 18, 21, X, And Y, Using Targeted Sequencing of Polymorphic Loci," Prenat. Diagn. 32(13):1233-1241, twenty one pages.

* cited by examiner

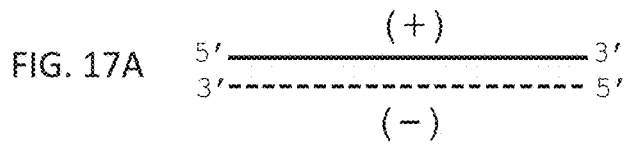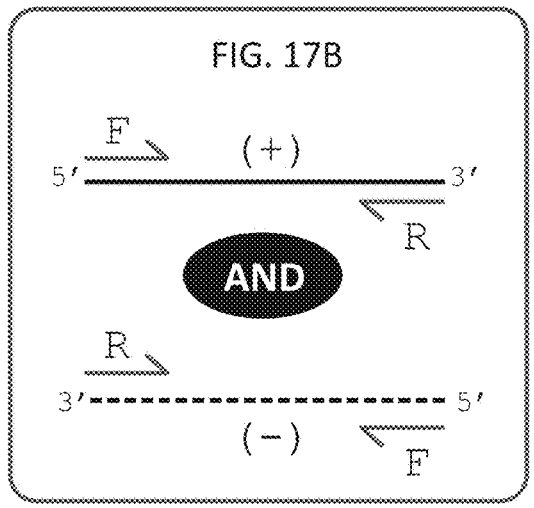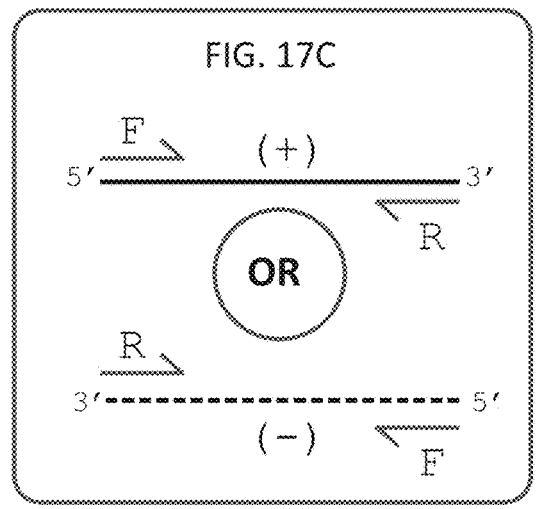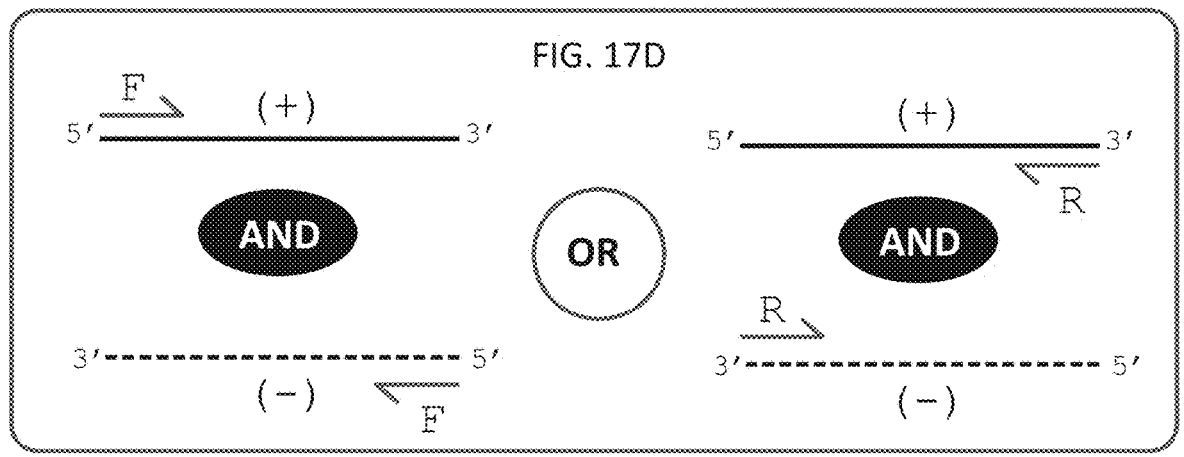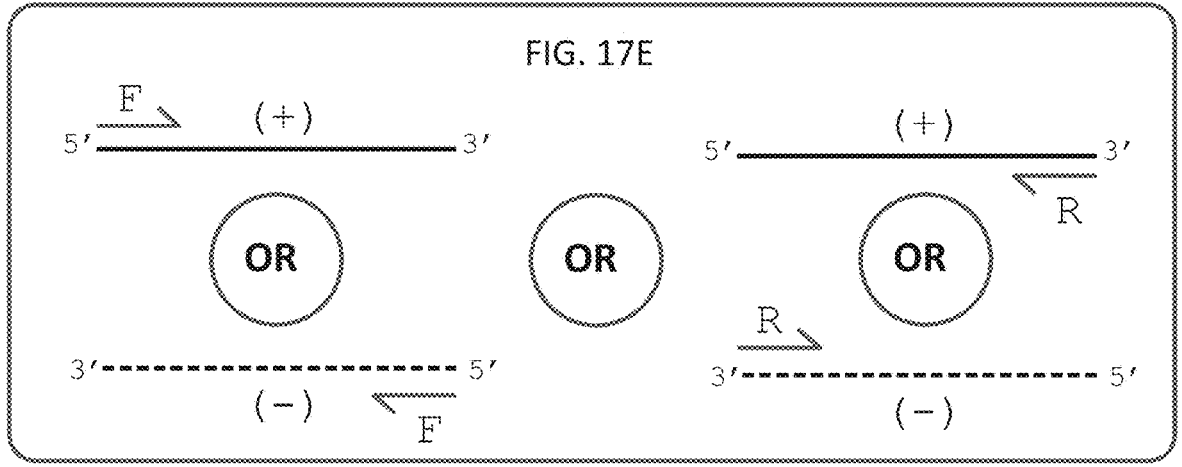

NUCLEIC ACID SEQUENCING ADAPTERS AND USES THEREOF

CROSS-REFERENCE TO RELATED APPLICATIONS

This applications claims priority benefit to U.S. Provisional Application No. 62/348,791, filed on Jun. 10, 2016, entitled "NUCLEIC ACID SEQUENCING ADAPTERS AND USES THEREOF"; U.S. Provisional Application No. 62/364,256, filed on Jul. 19, 2016, entitled "NUCLEIC ACID SEQUENCING ADAPTERS AND USES THEREOF"; and U.S. Provisional Application No. 62/447,784, filed on Jan. 18, 2017, entitled "NUCLEIC ACID SEQUENCING ADAPTERS AND USES THEREOF"; each of which is incorporated herein by reference for all purposes.

FIELD OF THE INVENTION

The present invention relates to methods and compositions for sequencing nucleic acids.

BACKGROUND

Next generation sequencing (NGS) of nucleic acids has greatly increased the rate of genomic sequencing, thereby bringing in a new era for medical diagnostics, forensics, metagenomics, and many other applications. Cell-free DNA in plasma, for example, has emerged as a promising biomarker in cancer, fetal medicine, and transplantation. See Schwarzenbach et al., *Cell-free nucleic acids as biomarkers in cancer patients*, Nat. Rev. Cancer, vol. 11, pp. 426-437 (2011); Zimmermann et al. *Noninvasive prenatal aneuploidy testing of chromosomes 13, 18, 21, X, and Y, using targeted sequencing of polymorphic loci*, Prenat. Diagn. vol. 32, pp. 1233-1241 (2012); and De Vlaminck et al., *Noninvasive monitoring of infection and rejection after lung transplantation*, Proc. Natl. Acad. Sci. U.S.A, vol. 112, pp. 13336-13341 (2015). However, these high-throughput approaches often incorporate errors, resulting in inaccuracies in a constructed consensus sequence. These errors can arise, for example, during nucleic acid amplification or sequencing, or downstream analysis. Additionally, errors can arise due to chemical damage of the original nucleic acid molecule. In some cases, as many as 1% of sequenced bases can be incorrectly identified. See, for example, Schirmer et al., *Illumina error profiles: resolving fine-scale variation in metagenomics sequencing data*, BMC Bioinformatics, vol. 17, p. 125 (2016). These errors in the nucleic acid consensus sequence limit the reliability of known NGS methods. Widespread clinical application relies on robust detection of genetic variants at ultra-low abundance.

Several fundamental barriers limit the facile detection of low-frequency variants. First, NGS technologies are subject to sequencer error, which imposes a lower limit of detection for rare alleles. Second, both the surrounding chemical environment as well as methods used during sample processing can cause strand-specific chemical damage of DNA bases that lead to incorrect nucleotide calls during sequencing, particularly in the case of cytosine and guanine nucleotides. See Costello et al., *Discovery and characterization of artefactual mutations in deep coverage targeted capture sequencing data due to oxidative DNA damage during sample preparation*, Nucleic Acids Res., vol. 41, e67 (2013). Finally, the total amount of sample also restricts the lower limit of detection as increasing the number of DNA molecules incorporated during sequencing library construction improves the likelihood that a rare variant of interest will be sequenced.

Tagging individual nucleic acid molecules with a molecular barcode (also referred to as a single molecule identifier (SMI) or a unique molecular identifier (UMI)) can reduce some of the errors that arise during nucleic acid sequencing methods. The molecular barcodes are ligated to nucleic acid fragments before being amplified and sequenced. Amplicons with the same molecular barcode would be assumed to arise from the same original nucleic acid molecule.

Prior methods of sequencing using molecular barcodes relied on molecular barcodes with an unknown sequence and uniform length prior to combining the sequencing adapters with the nucleic acid sequencing library. The molecular barcodes were either degenerate sequences (i.e., random N-mers) or semi-degenerate sequences (i.e., random N-mers with biases for a particular base at a given position). See, for example, US 2015/0044687, the full disclosure of which is hereby incorporated by reference. The strategy behind employing degenerate or semi-degenerate sequences for the molecular barcodes was to include a very large number of unique molecular barcode sequences in a pool of sequencing adapters. However, use of such molecular barcodes can still give rise to considerable error or mis-assignment, thereby propagating errors or generating new errors in a constructed consensus sequence.

The disclosures of all publications, patents, and patent applications referred to herein are hereby incorporated herein by reference in their entireties.

SUMMARY OF THE INVENTION

Provided herein, there is a method of sequencing a nucleic acid molecule, comprising: sequencing a first strand of a duplex nucleic acid molecule, resulting in a first strand read; wherein the duplex nucleic acid molecule is ligated to a sequencing adapter prior to being amplified; and the sequencing adapter is randomly selected from a plurality of sequencing adapters comprising a duplex molecular barcode with a predetermined sequence.

Also provided herein, there is a method of sequencing a nucleic acid molecule, comprising: sequencing a set of amplified first strands formed from a first strand of a duplex nucleic acid molecule, resulting in a set of first strand reads; and constructing a first strand consensus sequence using the set of first strand reads; wherein the duplex nucleic acid molecule is ligated to a sequencing adapter prior to being amplified; and the sequencing adapter is randomly selected from a plurality of sequencing adapters comprising a duplex molecular barcode with a predetermined sequence.

In some embodiments, of the above methods, the plurality of sequencing adapters comprises: a first sequencing adapter comprising a first duplex molecular barcode n nucleotides in length with a predetermined sequence; and a second sequencing adapter, comprising a second duplex molecular barcode n+x nucleotides in length with a predetermined sequence, wherein x is not zero.

Further provided herein, there is a method of sequencing a nucleic acid molecule, comprising: sequencing a first strand of a duplex nucleic acid molecule, resulting in a first strand read; wherein the duplex nucleic acid molecule is ligated to a sequencing adapter; and the sequencing adapter is randomly selected from a plurality of sequencing adapters comprising: a first sequencing adapter comprising a first duplex molecular barcode n nucleotides in length; and a second sequencing adapter comprising a second duplex molecular barcode n+x nucleotides in length, wherein x is not zero.

Additionally, there is provided herein a method of sequencing a nucleic acid molecule, comprising: sequencing a set of amplified first strands formed from a first strand of a duplex nucleic acid molecule, resulting in a set of first strand reads; and constructing a first strand consensus sequence using the set of first strand reads; wherein the duplex nucleic acid molecule is ligated to a sequencing adapter prior to being amplified; and the sequencing adapter is randomly selected from a plurality of sequencing adapters comprising: a first sequencing adapter comprising a first duplex molecular barcode n nucleotides in length; and a second sequencing adapter comprising a second duplex molecular barcode n+x nucleotides in length, wherein x is not zero.

In some embodiments of the methods described above, the plurality of sequencing adapters further comprises a third sequencing adapter comprising a third duplex molecular barcode n+y nucleotides in length with a predetermined sequence, wherein y is not zero or x. In some embodiments, x is 1 and y is 2.

In some embodiments of the methods described above n is between 8 and 16. In some embodiments, n is 12.

In some embodiments of the methods described above, the method further comprises amplifying the first strand of the duplex nucleic acid molecule.

In some embodiments of the methods described above, the method further comprises compiling the set of first strand reads. In some embodiments, the set of first strand reads is compiled based on sequence distance or alignment to a reference sequence.

In some embodiments of the methods described above, constructing the first strand consensus sequence comprises: comparing the first strand reads in the set of first strand reads; identifying and removing errors in the set of first strand reads; and constructing an error-corrected first-strand consensus sequence.

In some embodiments of the method described above, constructing the first strand consensus sequence comprises: constructing a first strand consensus sequence from the set of first strand reads; comparing the first strand consensus sequence to the set of first strand reads; identifying and removing errors in the set of first strand reads; and constructing an error-corrected first strand consensus sequence.

In some embodiments of the methods described above, the first strand is sequenced in a first direction and a second direction.

In some embodiments of the method described above, the method further comprises sequencing a set of amplified second strands formed from a second strand of the duplex nucleic acid molecule, resulting in a set of second strand reads; and constructing a second strand consensus sequence using the set of second strand reads. In some embodiments, the method further comprises amplifying the second strand of the duplex nucleic acid molecule to form the amplified second strands. In some embodiments of the methods described above, the second strand is sequenced in a first direction and a second direction. In some embodiments, the method further comprises compiling the set of second strand reads. In some embodiments, the method further comprises compiling the set of second strand reads based on sequence distance or alignment to a reference sequence. In some embodiments, the method further comprises comparing the first strand consensus sequence and the second strand consensus sequence; identifying and removing errors in the set of first strand reads and the set of second strand reads; and constructing an error-corrected duplex consensus sequence.

In some embodiments of the method described above, the method further comprises ligating sequencing adapters from the plurality of sequencing adapters to duplex nucleic acid molecules.

In some embodiments of the method described above, the sequencing adapters in the plurality of sequence adapters comprise a first constant 3'-overhang, and the duplex nucleic acid molecule comprises a second constant 3'-overhang complementary to the first 3'-overhang prior to ligation. In some embodiments, the first constant 3'-overhang is a thymine nucleotide and the second constant 3'-overhang is an adenine nucleotide.

In some embodiments of the method described above, the number of unique molecular barcodes in the plurality of sequencing adapters is between 2 and about 500.

In some embodiments of the method described above, the ratio of A/C to G/T nucleotides at any given position of the molecular barcodes is between about 2:1 and about 1:2 at the corresponding position relative to the length of the shortest molecular barcode in the plurality of sequencing adapters.

In some embodiments of the method described above, the ratio of A/C to G/T nucleotides at any given position of the molecular barcodes is about 1:1 at the corresponding position relative to the shortest molecular barcode in the plurality of sequencing adapters.

In some embodiments of the method described above, the proportion of adenine at any given position of the molecular barcodes is between 0.2 and 0.4 at the corresponding position relative to the shortest molecular barcode in the plurality of sequencing adapters; the proportion of cytosine at any given position of the molecular barcodes is between 0.2 and 0.4 at the corresponding position relative to the shortest molecular barcode in the plurality of sequencing adapters; the proportion of thymine at any given position of the molecular barcodes is between 0.2 and 0.4 at the corresponding position relative to the shortest molecular barcode in the plurality of sequencing adapters; and the proportion of guanine at any given position of the molecular barcodes is between 0.2 and 0.4 at the corresponding position relative to the shortest molecular barcode in the plurality of sequencing adapters.

In some embodiments of the method described above, the proportion of adenine within any given molecular barcodes is between 0.2 and 0.3; the proportion of cytosine within any given molecular barcodes is between 0.2 and 0.3; the proportion of thymidine within any given molecular barcodes is between 0.2 and 0.3; and the proportion of guanine within any given molecular barcodes is between 0.2 and 0.3.

In some embodiments of the method described above, the edit distance between each molecular barcode is 2 or more.

In some embodiments of the method described above, the sequencing adapters in the composition comprise a primer annealing site.

In some embodiments of the method described above, the sequencing adapters comprise a sample index nucleic acid sequence. In some embodiments, the sample index is incorporated into the sample index by amplifying the nucleic acid molecule. In some embodiments, the sequencing adapter comprises the sample index ligation of the sequencing adapter to the nucleic acid molecule. In some embodiments, the sample index nucleic acid sequence comprises a first portion and a second portion. In some embodiments, the first portion is within a first nucleic strand; and the second portion is within a second nucleic acid strand. In some embodiments, the sample index nucleic acid sequence is between about 6 and about 20 nucleotides in length. In some embodiments, the first portion and the second portion are each between about 3 and about 10 nucleotides in length. In some embodiments, the first portion and the second portion are of equal length. In some embodiments, the sample index nucleic acid sequence is about 16 nucleotides in length. In some embodiments, the proportion of adenine within the sample index nucleic acid sequence is between 0.2 and 0.4; the proportion of cytosine within the sample index nucleic acid sequence is between 0.2 and 0.4; the proportion of thymidine within the sample index nucleic acid sequence is between 0.2 and 0.4; and the proportion of guanine within the sample index nucleic acid sequence is between 0.2 and 0.4.

In some embodiments of the method described above, the plurality of sequence adapters comprises U-shaped sequence adapters, Y-shaped sequence adapters, or a combination thereof.

Also provided herein, there is a method of identifying an error in a nucleic acid sequence, comprising: sequencing a first strand of a duplex nucleic acid molecule, resulting in a first strand read; sequencing a second strand of the duplex nucleic acid molecule, resulting in a second strand read; and comparing the first strand read to the second strand read; wherein the duplex nucleic acid molecule is ligated to a sequencing adapter; and the sequencing adapter is randomly selected from a plurality of sequencing adapters comprising a duplex molecular barcode with a predetermined sequence.

Further provided herein, there is a method of identifying an error in a nucleic acid sequence, comprising: sequencing a set of amplified first strands formed from a first strand of a duplex nucleic acid molecule, resulting in a set of first strand reads; sequencing a set of amplified second strands formed from a second strand of the duplex nucleic acid molecule, resulting in a set of second strand reads; constructing a first strand consensus sequence using the set of first strand reads; constructing a second strand consensus sequence using the set of second strand reads; and comparing the first strand consensus sequence to the second strand consensus sequence; wherein the duplex nucleic acid molecule is ligated to a sequencing adapter prior to being amplified; and the sequencing adapter is randomly selected from a plurality of sequencing adapters comprising a duplex molecular barcode with a predetermined sequence.

Additionally, there is provided herein a method of identifying an error in a nucleic acid sequence, comprising: sequencing a first strand of a duplex nucleic acid molecule, resulting in a first strand read; sequencing a second strand of the duplex nucleic acid molecule, resulting in a second strand read; comparing the first strand read to the second strand read; wherein the duplex nucleic acid molecule is ligated to a sequencing adapter; and the sequencing adapter is randomly selected from a plurality of sequencing adapters comprising: a first sequencing adapter comprising a first duplex molecular barcode n nucleotides in length; and a second sequencing adapter comprising a second duplex molecular barcode n+x nucleotides in length, wherein x is not zero.

Also provided herein, there is a method of identifying an error in a nucleic acid sequence, comprising: sequencing a set of amplified first strands formed from a first strand of a duplex nucleic acid molecule, resulting in a set of first strand reads; sequencing a set of amplified second strands formed from a second strand of the duplex nucleic acid molecule, resulting in a set of second strand reads; constructing a first strand consensus sequence using the set of first strand reads; constructing a second strand consensus sequence using the set of second strand reads; and comparing the first strand consensus sequence to the second strand consensus sequence; wherein the duplex nucleic acid molecule is ligated to a sequencing adapter prior to being amplified; and the sequencing adapter is randomly selected from a plurality of sequencing adapters comprising: a first sequencing adapter comprising a first duplex molecular barcode n nucleotides in length; and a second sequencing adapter comprising a second duplex molecular barcode n+x nucleotides in length, wherein x is not zero.

In some embodiments of the methods described above, the first strand is sequenced in a first direction and a second direction. In some embodiments, the second strand is sequenced in a first direction and a second direction.

In some embodiments of the methods described above, the duplex nucleic acid molecule is ligated to two sequencing adapters.

In some embodiments of the methods described above, the duplex nucleic acid molecule is a cell-free DNA molecule. In some embodiments, the duplex nucleic acid molecule is a cell-free tumor DNA molecule or a cell-free fetal DNA molecule.

In some embodiments of the methods described above, the duplex nucleic acid molecule is enriched from a nucleic acid library. In some embodiments, the duplex nucleic acid molecule is enriched using a set of capture probes for a region of interest. In some embodiments, the set of capture probes is balanced to provide a reduced sequencing depth variance relative to a set of capture probes comprising a plurality of approximately equally represented capture probes. In some embodiments, the set of capture probes is prepared by: sequencing a reference sequencing library comprising a plurality of nucleic acid molecules enriched using a first set of capture probes, wherein each capture probe comprises a sequence that is substantially complementary to a portion of or adjacent to a region of interest included in the reference sequencing library, and wherein an initial known amount of each capture probe is used to form the first set of capture probes; determining a sequencing depth attributable to each capture probe; selecting a subsequent known amount of each capture probe based on the initial known amount and the sequencing depth attributable to said capture probe, wherein the subsequent known amount of each capture probe is selected to minimize a difference between a predicted sequencing depth profile and a desired sequencing depth profile; and constructing the balanced set of capture probes by combining at least a fraction of the capture probes at the subsequent known amount of each capture probe in the balanced set of capture probes. In some embodiments, minimization of the difference is constrained by a minimum subsequent amount or a maximum subsequent amount of each capture probe. In some embodiments, the desired sequencing depth profile is uniform. In some embodiments, the desired sequencing depth profile is non-uniform. In some embodiments, the difference between the predicted sequencing depth profile and the desired sequencing depth profile is defined by an objective function. In some embodiments, the desired sequencing depth profile is implied by the objective function.

In some embodiments, the initial known amount is an initial known volume and the subsequent known amount is a subsequent known volume. In some embodiments, the initial known amount is an initial known mass or an initial known number of moles, and the subsequent known amount is a subsequent known mass or a subsequent known number of moles. In some embodiments, the initial known amount is an initial known relative amount and the subsequent known amount is a subsequent known relative amount.

In some embodiments, the sequencing depth is based on a number of sequencing reads that comprise a sequence substantially complementary to a sequence within the capture probe. In some embodiments, the sequencing depth is based on a number of sequencing reads that comprise a sequence substantially complementary to at least half of the capture probe. In some embodiments, the number of sequencing reads is a number of consensus sequencing reads. In some embodiments, the number of sequencing reads is a number of duplex consensus sequencing reads.

In some embodiments, the capture probes are not substantially complementary to overlapping portions of the region of interest. In some embodiments, at least two capture probes in the plurality of capture probes are substantially complementary to overlapping portions of the region of interest.

In some embodiments, the method comprises obtaining for each capture probe a binding fraction based on the sequencing depth attributable to the capture probe; and wherein the subsequent known amount is based on the initial known amount and the binding fraction. In some embodiments, the method comprises obtaining for each capture probe a binding fraction, wherein the binding fraction is determined for the fraction of nucleic acid molecules comprising a segment substantially complementary to at least half of the capture probe that bound to the capture probe during enrichment of the reference sequencing library based on the sequencing depth attributable to the capture probe; and wherein the subsequent known amount is based on the initial known amount and the fraction. In some embodiments, obtaining the binding fraction comprises approximating the sequencing depth for a given capture probe i as a Poisson distribution:

$$d_{is} = \text{Poisson}(N_s \pi_i)$$

wherein $d_{is}$ is the determined sequencing depth attributable to the capture probe i; $N_s$ is the number of nucleic acid molecules in reference sequencing library s; and $\pi_i$ is the binding fraction for capture probe i. In some embodiments, $\pi_i$ is determined by fitting a maximum likelihood model or a Markov chain Monte Carlo model.

In some embodiments, the difference is defined by an objective function of the subsequent amounts of the capture probes in the balanced set of capture probes, according to:

$$f(\vec{v}) = V(\vec{\pi}(\vec{v}))$$

wherein:

$$(\vec{\pi}(\vec{v}))_i = \left(1 + \frac{\gamma_i}{v_i c_i}\right)^{-1}$$

wherein: $V(\ )$ is a user-defined objective function for the set of capture probes; $(\vec{\pi}(\vec{v}))_i$ is the binding fraction for capture probe i for the vector $\vec{\pi}(\vec{v})$; $c_i$ is an effective concentration for capture probe i for the vector $\vec{\pi}(\vec{v})$; $v_i$ is the subsequent amount of capture probe i for the vector $\vec{\pi}(\vec{v})$; and $\gamma_i$ is the initial amount of capture probe i for the vector $\vec{\pi}(\vec{v})$.

In some embodiments, the difference is an objective function defined by a coefficient of variation.

In some embodiments of the methods described above, the method further comprises enriching the reference sequencing library using the balanced set of capture probes; sequencing the reference sequencing library enriched using the balanced set of capture probes; determining a sequencing depth attributable to each capture probe in the balanced set of capture probes; selecting a second subsequent known amount of each capture probe based on the subsequent known amount of said capture probe in the balanced set of capture probes and the sequencing depth attributable to said capture probe, wherein the second subsequent known amount of each capture probe is selected to minimize a difference between a second predicted sequencing depth profile and the desired sequencing depth profile; and constructing a re-balanced set of capture probes by combining at least a fraction of the capture probes at the second subsequent known amount of each capture probe in the re-balanced set of capture probes. In some embodiments, minimization of the difference is constrained by a minimum second subsequent amount or a maximum second subsequent amount of each capture probe.

In some embodiments, constructing the balanced set of capture probes comprises combining each capture probe in the first set of capture probes at the subsequent known amount of each capture probe in the balanced set capture probe.

Further provided herein, there is a composition comprising a plurality of sequencing adapters comprising a duplex molecular barcode having a nondegenerate sequence. In some embodiments, the plurality of sequencing adapters comprises: a first sequencing adapter comprising a first duplex molecular barcode n nucleotides in length; and a second sequencing adapter, comprising a second duplex molecular barcode n+x nucleotides in length, wherein x is not zero.

Also provided herein, there is a composition comprising: a first sequencing adapter comprising a first duplex molecular barcode n nucleotides in length; and a second sequencing adapter, comprising a second duplex molecular barcode n+x nucleotides in length, wherein x is not zero.

In some embodiments of the compositions described above, the composition further comprises a third sequencing adapter comprising a third molecular barcode comprising a nucleic acid duplex n+y nucleotides in length, wherein y is not zero or x. In some embodiments, x is 1 and y is 2.

In some embodiments of the composition described above, n is between 8 and 16. In some embodiments, n is 12.

In some embodiments of the composition described above, the sequencing adapters in the composition comprise a constant 3'-overhang. In some embodiments, the constant 3'-overhang is a thymine nucleotide.

In some embodiments of the composition described above, the number of unique molecular barcodes in the plurality of sequencing adapters is between 2 and about 500.

In some embodiments of the composition described above, the ratio of A/C to G/T nucleotides at any given position of the molecular barcodes is between about 2:1 and about 1:2 at the corresponding position relative to the shortest molecular barcode in the plurality of sequencing adapters.

In some embodiments of the composition described above, the ratio of A/C to G/T nucleotides at any given position of the molecular barcodes is about 1:1 at the corresponding position relative to the shortest molecular barcode in the plurality of sequencing adapters.

In some embodiments of the composition described above, the proportion of adenine at any given position of the molecular barcodes is between 0.2 and 0.4 at the corresponding position relative to the shortest molecular barcode in the plurality of sequencing adapters; the proportion of cytosine at any given position of the molecular barcodes is between 0.2 and 0.4 at the corresponding position relative to the shortest molecular barcode in the plurality of sequencing adapters; the proportion of thymine at any given position of the molecular barcodes is between 0.2 and 0.4 at the corresponding position relative to the shortest molecular barcode in the plurality of sequencing adapters; and the proportion of guanine at any given position of the molecular barcodes is between 0.2 and 0.4 at the corresponding position relative to the shortest molecular barcode in the plurality of sequencing adapters.

In some embodiments of the composition described above, the proportion of adenine within any given molecular barcodes is between 0.2 and 0.4; the proportion of cytosine within any given molecular barcodes is between 0.2 and 0.4; the proportion of thymidine within any given molecular barcodes is between 0.2 and 0.4; and the proportion of guanine within any given molecular barcodes is between 0.2 and 0.4.

In some embodiments of the composition described above, the edit distance between each molecular barcode is 2 or more.

In some embodiments of the composition described above, the sequencing adapters in the composition comprise a primer annealing site.

In some embodiments of the composition described above, the sequencing adapters comprise a sample index. In some embodiments, the sample index comprises a first portion and a second portion. In some embodiments, the first portion is within a first nucleic strand; and the second portion is within a second nucleic acid strand. In some embodiments, the sample index is between about 6 and about 20 nucleotides in length. In some embodiments, the first portion and the second portion are each between about 3 and about 10 nucleotides in length. In some embodiments, the first portion and the second portion are of equal length. In some embodiments, the sample index is about 16 nucleotides in length. In some embodiments, the proportion of adenine within the sample index is between 0.2 and 0.4; the proportion of cytosine within the sample index is between 0.2 and 0.4; the proportion of thymine within the sample index is between 0.2 and 0.4; and the proportion of guanine within the sample index is between 0.2 and 0.4.

In some embodiments of the composition described above, the plurality of sequence adapters comprises U-shaped sequencing adapters, Y-shaped sequencing adapters, or a combination thereof.

Also provided herein, there is a nucleic acid sequencing library comprising a plurality of nucleic acid inserts ligated to at least one sequencing adapter randomly selected from a plurality of sequencing adapters comprising a duplex molecular barcode having a nondegenerate sequence. In some embodiments, the plurality of sequencing adapters comprises: a first sequencing adapter comprising a first molecular barcode comprising a nucleic acid duplex n nucleotides in length; and a second sequencing adapter comprising a second molecular barcode comprising a nucleic acid duplex n+x nucleotides in length, wherein x is not zero.

Further provided herein, there is a nucleic acid sequencing library comprising a plurality of nucleic acid inserts ligated to at least one sequencing adapter, wherein the sequencing adapter is randomly selected from a plurality of sequencing adapters; wherein the plurality of sequencing adapters comprises: a first sequencing adapter comprising a first molecular barcode comprising a nucleic acid duplex n nucleotides in length; and a second sequencing adapter comprising a second molecular barcode comprising a nucleic acid duplex n+x nucleotides in length, wherein x is not zero.

In some embodiments of the nucleic acid sequencing library described above, the nucleic acid inserts in the plurality of nucleic acid inserts are ligated to two sequencing adapters from the plurality of sequencing adapters.

In some embodiments of the nucleic acid sequencing library described above, the sequencing adapters comprise a sample index.

In some embodiments of the nucleic acid sequencing library described above, the nucleic acid inserts comprise a cell-free DNA molecule. In some embodiments, the nucleic acid inserts comprise a cell-free tumor DNA molecule or a cell-free fetal DNA molecule.

In some embodiments of the nucleic acid sequencing library described above, the nucleic acid inserts are enriched from a nucleic acid library. In some embodiments, wherein the nucleic acid inserts are enriched using a set of capture probes for a region of interest. In some embodiments, the set of capture probes is balanced to provide a reduced sequencing depth variance relative to a set of capture probes comprising a plurality of approximately equally represented capture probes. In some embodiments, the set of capture probes is prepared by: sequencing a reference sequencing library comprising a plurality of nucleic acid molecules enriched using a first set of capture probes, wherein each capture probe comprises a sequence that is substantially complementary to a portion of or adjacent to a region of interest included in the reference sequencing library, and wherein an initial known amount of each capture probe is used to form the first set of capture probes; determining a sequencing depth attributable to each capture probe; selecting a subsequent known amount of each capture probe based on the initial known amount and the sequencing depth attributable to said capture probe, wherein the subsequent known amount of each capture probe is selected to minimize a difference between a predicted sequencing depth profile and a desired sequencing depth profile; and constructing the balanced set of capture probes by combining at least a fraction of the capture probes at the subsequent known amount of each capture probe in the balanced set of capture probes. In some embodiments, minimization of the difference is constrained by a minimum subsequent amount or a maximum subsequent amount of each capture probe. In some embodiments, the desired sequencing depth profile is uniform. In some embodiments, the desired sequencing depth profile is non-uniform. In some embodiments, the difference between the predicted sequencing depth profile and the desired sequencing depth profile is defined by an objective function. In some embodiments, the desired sequencing depth profile is implied by the objective function.

In some embodiments of the nucleic acid sequencing library described above, the initial known amount is an initial known volume and the subsequent known amount is a subsequent known volume. In some embodiments, the initial known amount is an initial known mass or an initial known number of moles, and the subsequent known amount is a subsequent known mass or a subsequent known number of moles. In some embodiments, the initial known amount is an initial known relative amount and the subsequent known amount is a subsequent known relative amount.

In some embodiments of the nucleic acid sequencing library described above, the sequencing depth is based on a number of sequencing reads that comprise a sequence substantially complementary to a sequence within the capture probe. In some embodiments, the sequencing depth is based on a number of sequencing reads that comprise a sequence substantially complementary to at least half of the capture probe. In some embodiments, the number of sequencing reads is a number of consensus sequencing reads. In some embodiments, the number of sequencing reads is a number of duplex consensus sequencing reads.

In some embodiments of the nucleic acid sequencing library described above, the capture probes are not substantially complementary to overlapping portions of the region of interest. In some embodiments, at least two capture probes in the plurality of capture probes are substantially complementary to overlapping portions of the region of interest.

In some embodiments of the nucleic acid sequencing library described above, the method comprises obtaining for each capture probe a binding fraction based on the sequencing depth attributable to the capture probe; and wherein the subsequent known amount is based on the initial known amount and the binding fraction. In some embodiments, the method comprises obtaining for each capture probe a binding fraction, wherein the binding fraction is determined for the fraction of nucleic acid molecules comprising a segment substantially complementary to at least half of the capture probe that bound to the capture probe during enrichment of the reference sequencing library based on the sequencing depth attributable to the capture probe; and wherein the subsequent known amount is based on the initial known amount and the fraction. In some embodiments, obtaining the binding fraction comprises approximating the sequencing depth for a given capture probe i as a Poisson distribution:

$$d_{is} = \text{Poisson}(N_s \pi_i)$$

wherein $d_{is}$ is the determined sequencing depth attributable to the capture probe i; $N_s$ is the number of nucleic acid molecules in reference sequencing library s; and $\pi_i$ is the binding fraction for capture probe i. In some embodiments, $\pi_i$ is determined by fitting a maximum likelihood model or a Markov chain Monte Carlo model.

In some embodiments of the nucleic acid sequencing library described above, the difference is defined by an objective function of the subsequent amounts of the capture probes in the balanced set of capture probes, according to:

$$f(\vec{v}) = V(\vec{\pi}(\vec{v}))$$

wherein:

$$(\vec{\pi}(\vec{v}))_i = \left(1 + \frac{\gamma_i}{v_i c_i}\right)^{-1}$$

wherein: V( ) is a user-defined objective function for the set of capture probes; $(\vec{\pi}(\vec{v}))_i$ is the binding fraction for capture probe i for the vector $\vec{\pi}(\vec{v})$; $c_i$ is an effective concentration for capture probe i for the vector $\vec{\pi}(\vec{v})$; $v_i$ is the subsequent amount of capture probe i for the vector $\vec{\pi}(\vec{v})$; and $\gamma_i$ is the initial amount of capture probe i for the vector $\vec{\pi}(\vec{v})$.

In some embodiments of the nucleic acid sequencing library described above, the difference is an objective function defined by a coefficient of variation.

In some embodiments of the nucleic acid sequencing library described above, the method further comprises enriching the reference sequencing library using the balanced set of capture probes; sequencing the reference sequencing library enriched using the balanced set of capture probes; determining a sequencing depth attributable to each capture probe in the balanced set of capture probes; selecting a second subsequent known amount of each capture probe based on the subsequent known amount of said capture probe in the balanced set of capture probes and the sequencing depth attributable to said capture probe, wherein the second subsequent known amount of each capture probe is selected to minimize a difference between a second predicted sequencing depth profile and the desired sequencing depth profile; and constructing a re-balanced set of capture probes by combining at least a fraction of the capture probes at the second subsequent known amount of each capture probe in the re-balanced set of capture probes. In some embodiments, minimization of the difference is constrained by a minimum second subsequent amount or a maximum second subsequent amount of each capture probe.

In some embodiments of the nucleic acid sequencing library described above, constructing the balanced set of capture probes comprises combining each capture probe in the first set of capture probes at the subsequent known amount of each capture probe in the balanced set capture probe.

Also provided herein, there is a pooled nucleic acid sequencing library comprising a first nucleic acid sequencing library and a second nucleic acid sequencing library, wherein the first nucleic acid sequencing library comprises a first plurality of nucleic acid inserts bound to at least one sequencing adapter from a first plurality of sequencing adapters comprising: a first duplex molecular barcode having a nondegenerate sequence; and a first sample index; wherein the second nucleic acid sequencing library comprises a second plurality of nucleic acid inserts bound to at least one sequencing adapter from a second plurality of sequencing adapters comprising: a second duplex molecular barcode having a nondegenerate sequence; and a second sample index; and wherein the first sample index and the second sample index are different. In some embodiments, the first molecular barcode and the second molecular barcode have the same sequence. In some embodiments, the first molecular barcode and the second molecular barcode have different sequences.

Further provided herein, there is a pooled nucleic acid sequencing library comprising a first nucleic acid sequencing library and a second nucleic acid sequencing library, wherein the first nucleic acid sequencing library comprises a first plurality of nucleic acid inserts bound to at least one sequencing adapter from a first plurality of sequencing adapters comprising: a first sequencing adapter comprising a first molecular barcode comprising a nucleic acid duplex n nucleotides in length; and a second sequencing adapter comprising a second molecular barcode comprising a nucleic acid duplex n+x nucleotides in length, wherein x is not zero; wherein the second nucleic acid sequencing library comprises a second plurality of polynucleotides bound to at least one sequencing adapter from a second plurality of sequencing adapters comprising: a third sequencing adapter comprising a third molecular barcode comprising a nucleic acid duplex m nucleotides in length; and a fourth sequencing adapter comprising a fourth molecular barcode comprising a nucleic acid duplex m+a nucleotides in length, wherein a is not zero; wherein the first sample index sequence and the second sample sequence index are different. In some embodiments, the first molecular barcode and the third molecular barcode are the same. In some embodiments, the second molecular barcode and the fourth molecular barcode are the same.

In some embodiments of the pooled nucleic acid sequencing library described above, the nucleic acid inserts comprise a cell-free DNA molecule. In some embodiments, the nucleic acid inserts comprise a cell-free tumor DNA molecule or a cell-free fetal DNA molecule.

In some embodiments of the pooled nucleic acid sequencing library described above, the nucleic acid inserts are enriched from a nucleic acid library. In some embodiments, nucleic acid inserts are enriched using a set of capture probes for a region of interest. In some embodiments, the set of capture probes is balanced to provide a reduced sequencing depth variance relative to a set of capture probes comprising a plurality of approximately equally represented capture probes. In some embodiments, the set of capture probes is prepared by: sequencing a reference sequencing library comprising a plurality of nucleic acid molecules enriched using a first set of capture probes, wherein each capture probe comprises a sequence that is substantially complementary to a portion of or adjacent to a region of interest included in the reference sequencing library, and wherein an initial known amount of each capture probe is used to form the first set of capture probes; determining a sequencing depth attributable to each capture probe; selecting a subsequent known amount of each capture probe based on the initial known amount and the sequencing depth attributable to said capture probe, wherein the subsequent known amount of each capture probe is selected to minimize a difference between a predicted sequencing depth profile and a desired sequencing depth profile; and constructing the balanced set of capture probes by combining at least a fraction of the capture probes at the subsequent known amount of each capture probe in the balanced set of capture probes. In some embodiments, minimization of the difference is constrained by a minimum subsequent amount or a maximum subsequent amount of each capture probe. In some embodiments, the desired sequencing depth profile is uniform. In some embodiments, the desired sequencing depth profile is non-uniform. In some embodiments, the difference between the predicted sequencing depth profile and the desired sequencing depth profile is defined by an objective function. In some embodiments, the desired sequencing depth profile is implied by the objective function.

In some embodiments of the nucleic acid sequencing library described above, the initial known amount is an initial known volume and the subsequent known amount is a subsequent known volume. In some embodiments, the initial known amount is an initial known mass or an initial known number of moles, and the subsequent known amount is a subsequent known mass or a subsequent known number of moles. In some embodiments, the initial known amount is an initial known relative amount and the subsequent known amount is a subsequent known relative amount.

In some embodiments of the pooled nucleic acid sequencing library described above, the sequencing depth is based on a number of sequencing reads that comprise a sequence substantially complementary to a sequence within the capture probe. In some embodiments, the sequencing depth is based on a number of sequencing reads that comprise a sequence substantially complementary to at least half of the capture probe. In some embodiments, the number of sequencing reads is a number of consensus sequencing reads. In some embodiments, the number of sequencing reads is a number of duplex consensus sequencing reads.

In some embodiments of the nucleic acid sequencing library described above, the capture probes are not substantially complementary to overlapping portions of the region of interest. In some embodiments, at least two capture probes in the plurality of capture probes are substantially complementary to overlapping portions of the region of interest.

In some embodiments of the pooled nucleic acid sequencing library described above, the method comprises obtaining for each capture probe a binding fraction based on the sequencing depth attributable to the capture probe; and wherein the subsequent known amount is based on the initial known amount and the binding fraction. In some embodiments, the method comprises obtaining for each capture probe a binding fraction, wherein the binding fraction is determined for the fraction of nucleic acid molecules comprising a segment substantially complementary to at least half of the capture probe that bound to the capture probe during enrichment of the reference sequencing library based on the sequencing depth attributable to the capture probe; and wherein the subsequent known amount is based on the initial known amount and the fraction. In some embodiments, obtaining the binding fraction comprises approximating the sequencing depth for a given capture probe i as a Poisson distribution:

$$d_{is} = \text{Poisson}(N_s \pi_i)$$

wherein $d_{is}$ is the determined sequencing depth attributable to the capture probe i; $N_s$ is the number of nucleic acid molecules in reference sequencing library s; and $\pi_i$ is the binding fraction for capture probe i. In some embodiments, $\pi_i$ is determined by fitting a maximum likelihood model or a Markov chain Monte Carlo model.

In some embodiments of the pooled nucleic acid sequencing library described above, the difference is defined by an objective function of the subsequent amounts of the capture probes in the balanced set of capture probes, according to:

$$f(\vec{v}) = V(\vec{\pi}(\vec{v}))$$

wherein:

$$(\vec{\pi}(\vec{v}))_i = \left(1 + \frac{\gamma_i}{v_i c_i}\right)^{-1}$$

wherein: V( ) is a user-defined objective function for the set of capture probes; $(\vec{\pi}(\vec{v}))_i$ is the binding fraction for capture probe i for the vector $\vec{\pi}(\vec{v})$; $c_i$ is an effective concentration for capture probe i for the vector $\vec{\pi}(\vec{v})$; $v_i$ is the subsequent amount of capture probe i for the vector $\vec{\pi}(\vec{v})$; and $\gamma_i$ is the initial amount of capture probe i for the vector $\vec{\pi}(\vec{v})$.

In some embodiments of the pooled nucleic acid sequencing library described above, the difference is an objective function defined by a coefficient of variation.

In some embodiments of the pooled nucleic acid sequencing library described above, the method further comprises enriching the reference sequencing library using the balanced set of capture probes; sequencing the reference sequencing library enriched using the balanced set of capture probes; determining a sequencing depth attributable to each capture probe in the balanced set of capture probes; selecting a second subsequent known amount of each capture probe based on the subsequent known amount of said capture probe in the balanced set of capture probes and the sequencing depth attributable to said capture probe, wherein the second subsequent known amount of each capture probe is selected to minimize a difference between a second predicted sequencing depth profile and the desired sequencing depth profile; and constructing a re-balanced set of capture probes by combining at least a fraction of the capture probes at the second subsequent known amount of each capture probe in the re-balanced set of capture probes. In some embodiments, minimization of the difference is constrained by a minimum second subsequent amount or a maximum second subsequent amount of each capture probe.

In some embodiments of the nucleic acid sequencing library described above, constructing the balanced set of capture probes comprises combining each capture probe in the first set of capture probes at the subsequent known amount of each capture probe in the balanced set capture probe.

In some embodiments of the nucleic acid sequencing library described above, the nucleic acid inserts are ligated to two sequencing adapters. In some embodiments of the pooled nucleic acid sequencing library described above, the nucleic acid inserts are ligated to two sequencing adapters.

Further provided herein, there is a method of determining the number of unique nucleic acid molecules in a nucleic acid library, comprising: sequencing a set of amplified first strands formed from a first strand of a duplex nucleic acid molecule, resulting in a set of first strand reads; compiling the set of first strand reads; and counting the number of sets of nucleic acid molecule reads; wherein the duplex nucleic acid molecule is ligated to a sequencing adapter prior to being amplified; and the sequencing adapter is randomly selected from a plurality of sequencing adapters comprising a duplex molecular barcode with a predetermined sequence.

Also provided herein, there is a method of determining the number of unique nucleic acid molecules in a sequencing library, comprising: sequencing a set of amplified first strands formed from a first strand of a duplex nucleic acid molecule, resulting in a set of first strand reads; compiling the set of first strand reads; and counting the number of sets of nucleic acid molecule reads; wherein the duplex nucleic acid molecule is ligated to a sequencing adapter prior to being amplified; and the sequencing adapter is randomly selected from a plurality of sequencing adapters comprising: a first sequencing adapter comprising a first duplex molecular barcode n nucleotides in length; and a second sequencing adapter comprising a second duplex molecular barcode n+x nucleotides in length, wherein x is not zero.

Additionally, there is provided here in a method of determining the number of unique nucleic acid molecules in a sequencing library, comprising: sequencing a set of amplified first strands formed from a first strand of a duplex nucleic acid molecule, resulting in a set of first strand reads; sequencing a set of amplified second strands formed from a second strand of a duplex nucleic acid molecule, resulting in a set of second strand reads; compiling the set of first strand reads; compiling the set of second strand reads; matching the set of first strand reads to the set of second strand reads; and counting the number of matched sets; wherein the duplex nucleic acid molecule is ligated to a sequencing adapter prior to being amplified; and the sequencing adapter is randomly selected from a plurality of sequencing adapters comprising a duplex molecular barcode with a predetermined sequence.

Also provided herein, there is a method of determining the number of unique nucleic acid molecules in a sequencing library, comprising: sequencing a set of amplified first strands formed from a first strand of a duplex nucleic acid molecule, resulting in a set of first strand reads; sequencing a set of amplified second strands formed from a second strand of a duplex nucleic acid molecule, resulting in a set of second strand reads; compiling the set of first strand reads; compiling the set of second strand reads; matching the set of first strand reads to the set of second strand reads; and counting the number of matched sets; wherein the duplex nucleic acid molecule is ligated to a sequencing adapter prior to being amplified; and the sequencing adapter is randomly selected from a plurality of sequencing adapters comprising: a first sequencing adapter comprising a first duplex molecular barcode n nucleotides in length; and a second sequencing adapter comprising a second duplex molecular barcode n+x nucleotides in length, wherein x is not zero.

BRIEF DESCRIPTION OF THE DRAWINGS

FIGS. 17A-E illustrate four different modes of sequencing a duplex nucleic acid molecules. FIG. 17A illustrates the duplex nucleic acid molecule with a first strand ("+") and a second strand ("−"). FIG. 17B illustrates sequencing the first strand and the second strand of the duplex nucleic acid molecule, with both strands being sequenced in the forward and reverse directions. FIG. 17C illustrates sequencing the first strand or the second strand of the duplex nucleic acid molecule, with the sequenced strand being sequenced in the forward and reverse directions. FIG. 17D illustrates sequencing the first strand and the second strand of the duplex nucleic acid molecule, with each strand being sequenced in a single direction. FIG. 17E illustrates sequencing the first strand or the second strand of the duplex nucleic acid molecule, with the sequencing strand being sequenced in a single direction.

DETAILED DESCRIPTION OF THE EMBODIMENTS

Figure 1A:
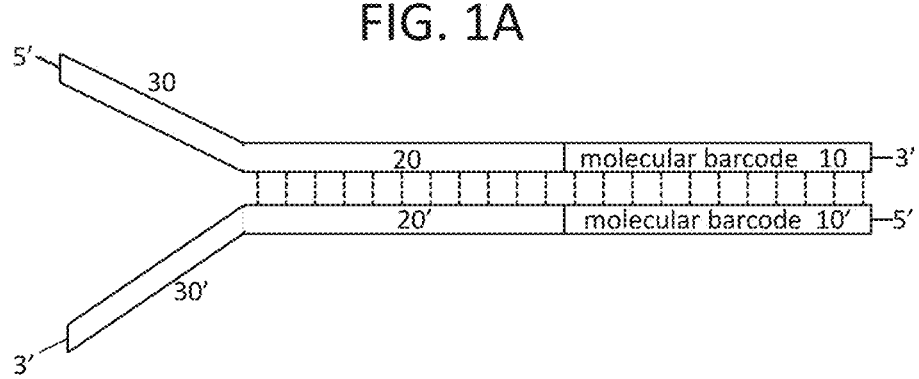
FIG. 1A illustrates one example of a Y-shaped sequencing adapter comprising a duplex molecular barcode.

The methods and sequencing adapters described herein are useful for identifying strand specific nucleic acid chemical damage or sequencing errors that may arise during sample preparation or sequencing. By maximizing duplex nucleic acid recovery (that is, recovering the sequence of both strands of a duplex nucleic acid molecule), a larger portion of errors can be identified and removed during post-sequencing analysis.

Described herein are methods of sequencing a nucleic acid molecule, methods of sequencing a nucleic acid library, sequencing adapters and compositions comprising sequencing adapters, nucleic acid sequencing libraries comprising nucleic acid inserts and the sequencing adapters, and methods of determining the number of unique nucleic acid molecules in a sequencing library.

The methods and compositions described herein can be used to sequence nucleic acids. The methods and compositions described herein can also be used to identify errors introduced during sequencing or amplification, identify locations of chemical damage to original nucleic acid molecules, and determine the number of unique nucleic acid molecules in a nucleic acid molecule library (such as a sequencing library). In some embodiments, there is provided a method of sequencing a nucleic acid sequence from a nucleic acid library using the sequencing adapters described herein. In some embodiments, there is a method of sequencing a nucleic acid sequencing using the sequencing adapters described herein. In some embodiments, there is provided a method of deep sequencing nucleic acids using the sequencing adapters described herein. In some embodiments, there is provided a method of next generation sequencing comprising ligating the sequencing adapters described herein to nucleic acid molecules; and sequencing the nucleic acid molecules.

In contrast to previously used degenerate or semi-degenerate molecular barcodes, in some aspects described herein, the molecular barcodes have predetermined (i.e., known) sequences or nondegenerate sequences. Nondegenerate or predetermined molecular barcodes are better than degenerate or semi-degenerate sequences for quality control when producing the sequencing adapters, improves the quality of sequencing data, limit the possibility of mis-assigning sequence reads to an incorrect set of nucleic acid reads, and allow for faster assignment of sequencing reads to sets of nucleic acid reads.

In one aspect, there is provided a method of sequencing a nucleic acid molecule. In some embodiments, the method comprises sequencing a first strand of a duplex nucleic acid molecule, resulting in a first strand read; wherein the duplex nucleic acid molecule is ligated to a sequencing adapter prior to being amplified; and the sequencing adapter is randomly selected from a plurality of sequencing adapters comprising a duplex molecular barcode with a predetermined sequence. The plurality of sequencing adapters includes a diversity of duplex molecular barcodes, with each molecular barcode having a predetermined sequence. In some embodiments, the method comprises sequencing a set of amplified first strands formed from a first strand of a duplex nucleic acid molecule, resulting in a set of first strand reads; and constructing a first strand consensus sequence using the set of first strand reads; wherein the duplex nucleic acid molecule is ligated to a sequencing adapter prior to being amplified; and the sequencing adapter is randomly selected from a plurality of sequencing adapters comprising a duplex molecular barcode with a predetermined sequence. In some embodiments, the method comprises sequencing a first strand of a duplex nucleic acid molecule, resulting in a first strand read; wherein the duplex nucleic acid molecule is ligated to a sequencing adapter; and the sequencing adapter is randomly selected from a plurality of sequencing adapters comprising a first sequencing adapter comprising a first duplex molecular barcode n nucleotides in length; and a second sequencing adapter comprising a second duplex molecular barcode n+x nucleotides in length, wherein x is not zero. In some embodiments, the method comprises sequencing a set of amplified first strands formed from a first strand of a duplex nucleic acid molecule, resulting in a set of first strand reads; and constructing a first strand consensus sequence using the set of first strand reads; wherein the duplex nucleic acid molecule is ligated to a sequencing adapter prior to being amplified; and the sequencing adapter is randomly selected from a plurality of sequencing adapters comprising first sequencing adapter comprising a first duplex molecular barcode n nucleotides in length; and a second sequencing adapter comprising a second duplex molecular barcode n+x nucleotides in length, wherein x is not zero.

In another aspect, there is provided a method of identifying an error in a nucleic acid sequence. In some embodiments, the method comprises sequencing a first strand of a duplex nucleic acid molecule, resulting in a first strand read; sequencing a second strand of the duplex nucleic acid molecule, resulting in a second strand read; and comparing the first strand read to the second strand read; wherein the duplex nucleic acid molecule is ligated to a sequencing adapter; and the sequencing adapter is randomly selected from a plurality of sequencing adapters comprising a duplex molecular barcode with a predetermined sequence. In some embodiments, the method comprises sequencing a set of amplified first strands formed from a first strand of a duplex nucleic acid molecule, resulting in a set of first strand reads; sequencing a set of amplified second strands formed from a second strand of the duplex nucleic acid molecule, resulting in a set of second strand reads; constructing a first strand consensus sequence using the set of first strand reads; constructing a second strand consensus sequence using the set of second strand reads; and comparing the first strand consensus sequence to the second strand consensus sequence; wherein the duplex nucleic acid molecule is ligated to a sequencing adapter prior to being amplified; and the sequencing adapter is randomly selected from a plurality of sequencing adapters comprising a duplex molecular barcode with a predetermined sequence. In some embodiments, the method comprises sequencing a first strand of a duplex nucleic acid molecule, resulting in a first strand read; sequencing a second strand of the duplex nucleic acid molecule, resulting in a second strand read; and comparing the first strand read to the second strand read; wherein the duplex nucleic acid molecule is ligated to a sequencing adapter; and the sequencing adapter is randomly selected from a plurality of sequencing adapters comprising a first sequencing adapter comprising a first duplex molecular barcode n nucleotides in length; and a second sequencing adapter comprising a second duplex molecular barcode n+x nucleotides in length, wherein x is not zero. In some embodiments, the method comprises sequencing a set of amplified first strands formed from a first strand of a duplex nucleic acid molecule, resulting in a set of first strand reads; sequencing a set of amplified second strands formed from a second strand of the duplex nucleic acid molecule, resulting in a set of second strand reads; constructing a first strand consensus sequence using the set of first strand reads; constructing a second strand consensus sequence using the set of second strand reads; and comparing the first strand consensus sequence to the second strand consensus sequence; wherein the duplex nucleic acid molecule is ligated to a sequencing adapter prior to being amplified; and the sequencing adapter is randomly selected from a plurality of sequencing adapters comprising a first sequencing adapter comprising a first duplex molecular barcode n nucleotides in length; and a second sequencing adapter comprising a second duplex molecular barcode n+x nucleotides in length, wherein x is not zero.

In a further aspect, there is provided a method of determining the number of unique nucleic acid molecules in a nucleic acid library. In some embodiments, the method comprises sequencing a set of amplified first strands formed from a first strand of a duplex nucleic acid molecule, resulting in a set of first strand reads; compiling the set of first strand reads; and; counting the number of sets of nucleic acid molecule reads; wherein the duplex nucleic acid molecule is ligated to a sequencing adapter prior to being amplified; and the sequencing adapter is randomly selected from a plurality of sequencing adapters comprising a duplex molecular barcode with a predetermined sequence. In some embodiments, the method comprises sequencing a set of amplified first strands formed from a first strand of a duplex nucleic acid molecule, resulting in a set of first strand reads; compiling the set of first strand reads; and counting the number of sets of nucleic acid molecule reads; wherein the duplex nucleic acid molecule is ligated to a sequencing adapter prior to being amplified; and the sequencing adapter is randomly selected from a plurality of sequencing adapters comprising a first sequencing adapter comprising a first duplex molecular barcode n nucleotides in length; and a second sequencing adapter comprising a second duplex molecular barcode n+x nucleotides in length, wherein x is not zero. In some embodiments, the method comprises sequencing a set of amplified first strands formed from a first strand of a duplex nucleic acid molecule, resulting in a set of first strand reads; sequencing a set of amplified second strands formed from a second strand of a duplex nucleic acid molecule, resulting in a set of second strand reads; compiling the set of first strand reads; compiling the set of second strand reads; matching the set of first strand reads to the set of second strand reads; and counting the number of matched sets; wherein the duplex nucleic acid molecule is ligated to a sequencing adapter prior to being amplified; and the sequencing adapter is randomly selected from a plurality of sequencing adapters comprising a duplex molecular barcode with a predetermined sequence. In some embodiments, the method comprises sequencing a set of amplified first strands formed from a first strand of a duplex nucleic acid molecule, resulting in a set of first strand reads; sequencing a set of amplified second strands formed from a second strand of a duplex nucleic acid molecule, resulting in a set of second strand reads; compiling the set of first strand reads; compiling the set of second strand reads; matching the set of first strand reads to the set of second strand reads; and counting the number of matched sets; wherein the duplex nucleic acid molecule is ligated to a sequencing adapter prior to being amplified; and the sequencing adapter is randomly selected from a plurality of sequencing adapters comprising a first sequencing adapter comprising a first duplex molecular barcode n nucleotides in length; and a second sequencing adapter comprising a second duplex molecular barcode n+x nucleotides in length, wherein x is not zero.

In another aspect, there is provided a composition comprising a plurality of sequencing adapters. In some embodiments, the composition comprises a plurality of sequencing adapters comprising a duplex molecular barcode having a nondegenerate sequence. In some embodiments, the composition comprises a first sequencing adapter comprising a first duplex molecular barcode n nucleotides in length; and a second sequencing adapter comprising a second duplex molecular barcode n+x nucleotides in length, wherein x is not zero.

In another aspect, there is provided a nucleic acid sequencing library. In some embodiments, the nucleic acid sequencing library comprises a plurality of polynucleotides ligated to at least one sequencing adapter from a plurality of sequencing adapters comprising a duplex molecular barcode having a nondegenerate sequence. In some embodiments, the nucleic acid sequencing library comprises a plurality of polynucleotides ligated to at least one sequencing adapter, wherein the sequencing adapter is randomly selected from a plurality of sequencing adapters; wherein the plurality of sequencing adapters comprises a first sequencing adapter comprising a first molecular barcode comprising a nucleic acid duplex n nucleotides in length; and a second sequencing adapter comprising a second molecular barcode comprising a nucleic acid duplex n+x nucleotides in length, wherein x is not zero.

In another aspect, there is provided a pooled nucleic acid sequencing library. In some embodiments, the pooled nucleic acid sequencing library comprises a first nucleic acid sequencing library and a second nucleic acid sequencing library, wherein the first nucleic acid sequencing library comprises a first plurality of polynucleotides bound to at least one sequencing adapter from a first plurality of sequencing adapters comprising a first molecular barcode having a nucleic acid duplex with a nondegenerate sequence; and a first sample index sequence; wherein the second nucleic acid sequencing library comprises a second plurality of polynucleotides bound to at least one sequencing adapter from a second plurality of sequencing adapters comprising a second molecular barcode having a nucleic acid duplex with a nondegenerate sequence; and a second sample index sequence; and wherein the first sample index sequence and the second sample sequence index are different. In some embodiments, the pooled nucleic acid sequencing library comprises a first nucleic acid sequencing library and a second nucleic acid sequencing library, wherein the first nucleic acid sequencing library comprises a first plurality of polynucleotides bound to at least one sequencing adapter from a first plurality of sequencing adapters comprising a first sequencing adapter comprising a first molecular barcode comprising a nucleic acid duplex n nucleotides in length; and a second sequencing adapter comprising a second molecular barcode comprising a nucleic acid duplex n+x nucleotides in length, wherein x is not zero; wherein the second nucleic acid sequencing library comprises a second plurality of polynucleotides bound to at least one sequencing adapter from a second plurality of sequencing adapters comprising a third sequencing adapter comprising a third molecular barcode comprising a nucleic acid duplex m nucleotides in length; and a fourth sequencing adapter comprising a fourth molecular barcode comprising a nucleic acid duplex m+a nucleotides in length, wherein a is not zero; wherein the first sample index sequence and the second sample sequence index are different.

Definitions

As used herein, the singular forms "a," "an," and "the" include the plural reference unless the context clearly dictates otherwise.

Reference to "about" a value or parameter herein includes (and describes) variations that are directed to that value or parameter per se. For example, description referring to "about X" includes description of "X". Additionally, use of "about" preceding any series of numbers includes "about" each of the recited numbers in that series. For example, description referring to "about X, Y, or Z" is intended to describe "about X, about Y, or about Z."

The term "average" as used herein refers to either a mean or a median, or any value used to approximate the mean or the median, unless the context clearly indicates otherwise.

It is understood that aspects and variations of the invention described herein include "consisting" and/or "consisting essentially of" aspects and variations.

A "portion adjacent to a region of interest" includes a portion adjacent to a sub-region of the region of interest (for example, when the region of interest includes a plurality of non-contiguous sub-regions). Reference to a "portion of or adjacent to a region of interest" refers to a sequence that 1) is entirely within the region of interest, 2) is entirely outside but adjacent to the region of interest, or 3) includes a contiguous sequence from within and adjacent to the region of interest. Reference to a "sequence that is substantially complementary to a portion of or adjacent to a region of interest" refers to 1) a sequence that is substantially complementary to a sequence entirely within the region of interest, 2) a sequence substantially complementary to a sequence entirely outside but adjacent to the region of interest, or 3) a sequence that is substantially complementary to a contiguous sequence from with and adjacent to the region of interest.

A "set" of reads refers to all sequencing reads with a common parent nucleic acid strand, which may or may not have had errors introduced during sequencing or amplification of the parent nucleic acid strand.

The term "substantially complementary" is used to refer to two nucleic acid sequences (X and Y) on opposite strands for which both are at least 12 bases in length and the complementarity fraction between them is at least 0.75. The complementarity fraction is calculated as follows. First, the optimal alignment between X and the reverse complement of Y is calculated with the Needleman-Wunsch algorithm (Needleman et al., *A general method applicable to the search for similarities in the amino acid sequence of two proteins*. Journal of Molecular Biology, vol. 48 (3), pp. 443-453 (1970)) using default parameters (i.e., match=+1, mismatch=−1, and gap=−1). Then, the number of matches is counted for the optimal alignment. Finally, the complementarity fraction is defined as the number of matches divided by the smaller of the lengths of either sequence, i.e., the fraction of the length that is complementary. The term "substantially complementary" includes completely complementary nucleic acid strands.

Where a range of values is provided, it is to be understood that each intervening value between the upper and lower limit of that range, and any other stated or intervening value in that stated range, is encompassed within the scope of the present disclosure. Where the stated range includes upper or lower limits, ranges excluding either of those included limits are also included in the present disclosure.

It is to be understood that one, some or all of the properties of the various embodiments described herein may be combined to form other embodiments of the present invention.

The section headings used herein are for organizational purposes only and are not to be construed as limiting the subject matter described.

Sequencing Adapters and Sequencing Adapter Compositions

In some embodiments, the sequencing adapters described herein comprise a molecular barcode having a nucleic acid duplex with a predetermined or nondegenerate sequence. In some embodiments, a plurality of sequencing adapters described herein comprise molecular barcodes of two or more different lengths (i.e., variable length barcodes). In some embodiments, the sequencing adapter comprises a constant 3'-overhang. In some embodiments, the sequencing adapter comprises a sample index. In some embodiments, the sequencing adapter comprises a primer annealing site. The sequencing adapters described herein can be used, for example, in any of the methods described herein.

In some embodiments, the sequencing adapters are Y-shaped sequencing adapters. In some embodiments, the sequencing adapters are U-shaped sequencing adapters. In some embodiments, a composition comprising a plurality of sequencing adapters comprises only Y-shaped adapters or both Y-shaped adapters and U-shaped adapters.

FIG. 1A illustrates one embodiment of a Y-shaped sequencing adapter comprising a molecular barcode 10 and 10'. As illustrated, the molecular barcode 10 in the top strand is complementary to the molecular barcode 10' on the bottom strand. In some embodiments, the sequencing adapter further comprises a second duplex region 20 and 20' adjacent to the molecular barcode 10 and 10'. In some embodiments, the sequencing adapter comprises a non-complementary region 30 and 30' adjacent to the molecular barcode 10 and 10' or the second duplex region 20 and 20'. In some embodiments, the non-complementary region 30 and/or 30' comprises a primer annealing site. Optionally, the primer annealing site extends into the second duplex region 20 and/or 20' The primer annealing site can be used, for example, to anneal a sequencing primer or amplification primer to the sequencing adapter such that the nucleic acid molecule can be amplified and/or sequenced.

Figure 1B:
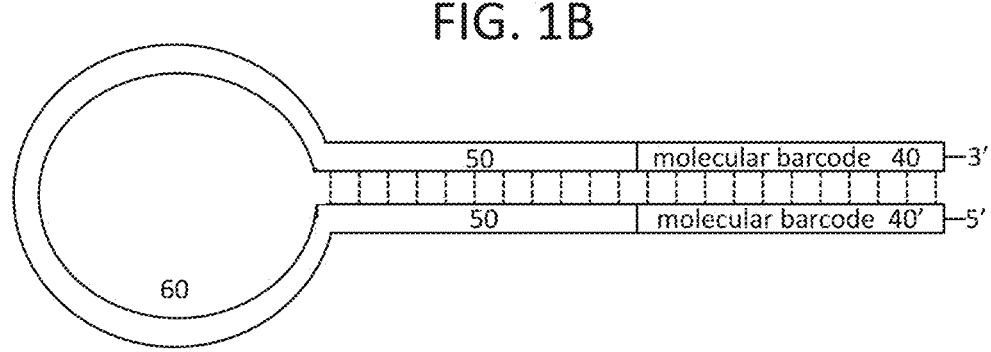
FIG. 1B illustrates one example of a U-shaped sequencing adapter comprising a duplex molecular barcode.

FIG. 1B illustrates one embodiment of a U-shaped sequencing adapter comprising a molecular barcode 40. The U-shaped sequencing adapter can include the same features as a Y-shaped sequencing adapter, however is a stem-loop structure wherein the non-complementary region is tethered together in a single nucleic acid strand. As illustrated, the molecular barcode 40 in the top strand is complementary to the molecular barcode 40' on the bottom strand. In some embodiments, the sequencing adapter further comprises a second duplex region 50 and 50' adjacent to the molecular barcode 40 and 40'. The U-shaped sequencing adapter also comprises a non-complementary loop region 60 adjacent to the molecular barcode 40 and 40' or the second duplex region 50 and 50'. In some embodiments, the non-complementary loop region 60 comprises a primer annealing site. The primer annealing site can be used, for example, to anneal a sequencing primer or amplification primer to the sequencing adapter such that the nucleic acid molecule can be amplified and/or sequenced.

Sequencing adapter compositions comprise a plurality of sequencing adapters, as described herein. The molecular barcodes in a plurality of sequencing adapters are diverse, although multiple copies of the same molecular barcode may be present in a composition comprising the plurality of sequencing adapters. For example, in some embodiments, the number of unique molecular barcodes in the plurality of sequencing adapters is between 2 and about 500, such as between about 10 and about 400, between about 20 and about 300, between about 50 and about 200, between about 10 and about 50, between about 50 and about 100, between about 75 and about 150, between about 100 and about 200, between about 200 and about 300, between about 300 and about 400, between about 400 and about 500, or about 24, about 48, about 96, about 192, or about 384.

In some embodiments, a molecular barcode in the plurality of sequencing adapters have an edit distance of 2 or more, 3 or more, 4 or more, 5 or more, 6 or more, 7 or more, or 8 or more from any other unique molecular barcode. Edit distance refers to the minimum number of single-base substitutions, single-base insertions, and/or single-base deletions that a pair of sequences must undergo to result in complete identity between the two sequences. For example, if the edit distance between a first molecular barcode and a second molecular barcode is 2, either the first molecular barcode must be mutated at least twice, the second molecular barcode must be mutated at least twice, or the first molecular barcode and the second molecular barcode must be mutated at least once each to result in identical sequences.

Figure 2:
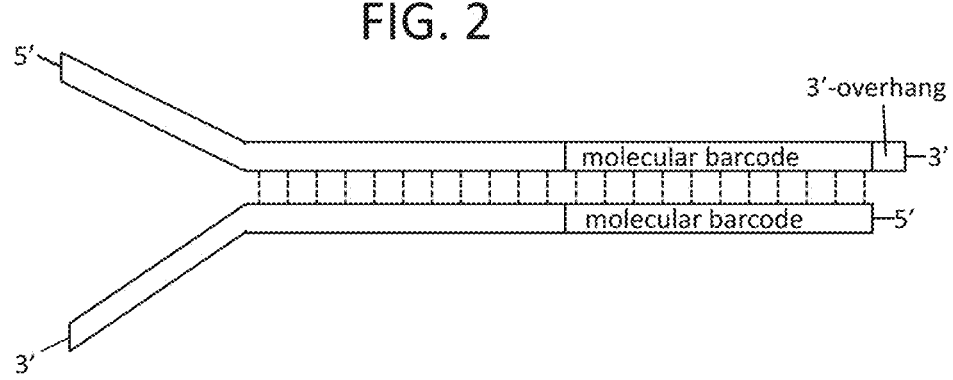
FIG. 2 illustrates one example of a sequencing adapter comprising a duplex molecular barcode and a constant 3'-overhang.

In some embodiments, the sequencing adapter further comprises a constant 3'-overhang, which can be adjacent to the molecular barcode in the sequencing adapter. The constant 3'-overhang is referred to as "constant" because the same 3'-overhang is used for each of the sequencing adapters in a composition. In some embodiments, the constant 3'-overhang can comprise adenine (A), thymine (T), guanine (G), cytosine (C), uracil (U), inosine (I), or any other natural or synthetic base. In some embodiments, the 3'-overhang comprises a dinucleotide, such as a guanine-cytosine (GC) dinucleotide. The constant 3'-overhang can be ligated to the nucleic acid molecule to be sequenced. FIG. 2 illustrates one exemplary embodiment of a sequencing adapter comprising a constant 3'-overhang. The molecular barcode is ligated adjacent to the nucleic acid molecule to be sequenced, except that it may be separated by the constant 3'-overhang (and/or its complementary base(s) that may be included in the complementary strand after ligation).

The molecular barcodes can be of any length, for example between about 2 and about 24 bases length. In some embodiments, the molecular barcodes are about 2, 3, 4, 5, 6, 7, 8, 9, 10, 11, 12, 13, 14, 15, 16, 17, 18, 19, 20, 21, 22, 23, or 24 bases in length. In some embodiments, a composition comprises a plurality of sequencing adapters, and the sequencing adapters comprise molecular barcodes of at least two different lengths, at least three different lengths, or at least four different lengths. For example, in some embodiments, a plurality of sequencing adapters comprises a first sequencing adapter comprising a first molecular barcode comprising a nucleic acid duplex n nucleotides in length; and a second sequencing adapter comprising a second molecular barcode comprising a nucleic acid duplex n+x nucleotides, wherein x is not zero. In some embodiments, the plurality of sequencing adapters further comprises a third sequencing adapter comprising a third molecular barcode comprising a nucleic acid duplex n+y nucleotides in length, wherein y is not zero or x.

Variable lengths of the molecular barcodes in the plurality of sequencing adapters are particularly useful, for example, when the sequencing adapters comprise a constant 3'-overhang. For example, if all molecular barcodes were of the same length, the constant 3'-overhang would be read in the same sequencing cycle, resulting in a large, non-diverse signal. Such non-diverse (or low diverse) signals can be problematic for many sequencing systems, as it can create a high level of noise that overwhelms the true signal at that position. Thus, by using variable length molecular barcodes, it ensures that no single sequencing cycle is presented with only a single base, thereby preventing loss of sequencing quality.

In some embodiments, the molecular barcodes are laser-color balanced. Similar to the variable lengths of the molecular barcodes, laser-color balancing can help ensure that no single sequencing cycle is presented with only a single base when sequencing the molecular barcode. For example, some sequencing systems employ colored lasers to sequence nucleic acid molecules (for example, in some sequencing systems, a green laser is used to sequence G or T nucleotides, and a red laser is used to sequence A or C nucleotides). To avoid oversaturation of signal, resulting in sequencing quality loss, the molecular barcodes can be color balanced. In some embodiments, the molecular barcodes are laser-color balanced amongst the plurality of sequence adapters. For example, in some embodiments, the ratio of A/C to G/T nucleotides at any given position of the molecular barcode in the plurality of sequence adapters is between about 2:1 and about 1:2 (such as about 1:1) at the corresponding position relative to the shortest molecular barcode in the plurality of sequencing adapters. In some embodiments, the molecular barcodes are laser-color balanced within any given molecular barcode. For example, in some embodiments, the ratio of A/C to G/T nucleotides within any given molecular barcode is between about 2:1 and about 1:2 (such as about 1:1).

In some embodiments, the molecular barcodes are base-composition balanced. In some embodiments, the molecular barcodes are base-composition balanced amongst the plurality of sequence adapters. For example, in some embodiments, the proportion of adenine at any given position of the molecular barcode amongst the plurality of sequence adapters is between about 0.2 and about 0.4 (such as between about 0.2 and about 0.3, or about 0.25) at the corresponding position relative to the shortest molecular barcode in the plurality of sequencing adapters; the proportion of cytosine at any given position of the molecular barcodes is between about 0.2 and about 0.4 (such as between about 0.2 and about 0.3, or about 0.25) at the corresponding position relative to the shortest molecular barcode in the plurality of sequencing adapters; the proportion of thymine at any given position of the molecular barcodes is between about 0.2 and about 0.4 (such as between about 0.2 and about 0.3, or about 0.25) at the corresponding position relative to the shortest molecular barcode in the plurality of sequencing adapters; and the proportion of guanine at any given position of the molecular barcodes is between about 0.2 and about 0.4 (such as between about 0.2 and about 0.3, or about 0.25) at the corresponding position relative to the shortest molecular barcode in the plurality of sequencing adapters. In some embodiments, the molecular barcodes are base-composition balanced within the molecular barcode. For example, in some embodiments, the proportion of adenine within any given molecular barcodes is between about 0.2 and about 0.4 (such as between about 0.2 and about 0.3, or about 0.25); the proportion of cytosine within any given molecular barcodes is between about 0.2 and about 0.4 (such as between about 0.2 and about 0.3, or about 0.25); the proportion of thymidine within any given molecular barcodes is between about 0.2 and about 0.4 (such as between about 0.2 and about 0.3, or about 0.25); and the proportion of guanine within any given molecular barcodes is between about 0.2 and about 0.4 (such as between about 0.2 and about 0.3, or about 0.25).

Figure 3:
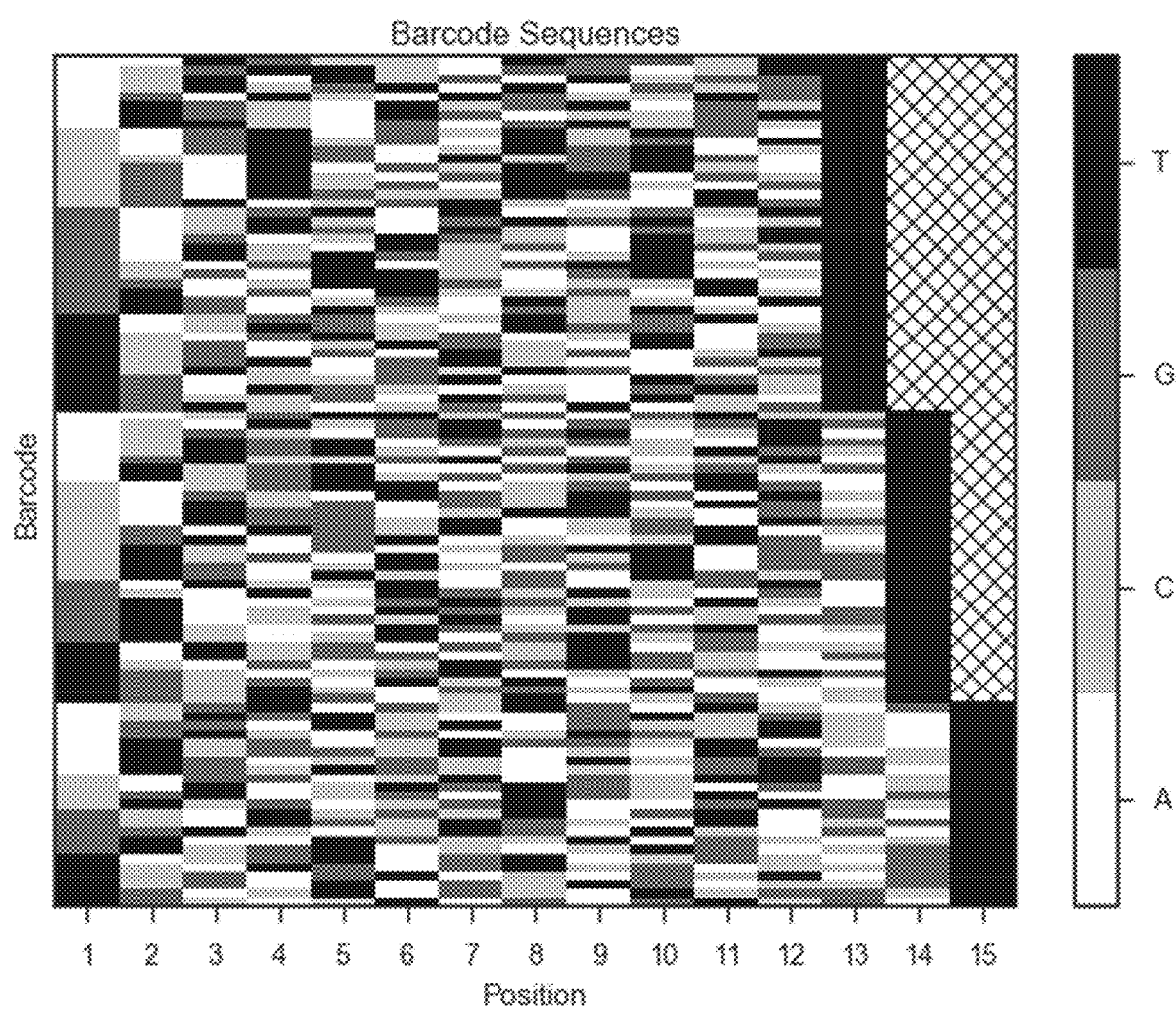
FIG. 3 presents a heatmap showing 96 base-composition balanced molecular barcodes of 12, 13, or 14 nucleotides in length, which precedes a constant 3'-overhang thymine nucleotide. All 96 molecular barcodes are base-composition balanced at positions 1-12. At position 13 and 14, the molecular barcodes longer than the shortest molecular barcode omit thymine to avoid signal oversaturation due to the constant 3'-overhang thymine nucleotide.

Laser-color balancing and base-composition balancing at any given position of the molecular barcode amongst the plurality of sequence adapters is preferably measured against the length of the shortest molecular barcode. This is because, in some embodiments, a constant 3'-overhang is adjacent to the molecular barcode in the sequencing adapter, which can cause a strong signal for that particular nucleotide. Including the same nucleotide at the position of a longer molecular barcode that overlaps the 3'-overhang following a shorter barcode, would add to the signal of the nucleotide in the 3'-overhang. Thus, in some embodiments, the molecular barcodes do not comprise the nucleotide present in the 3'-overhang at any position that would be co-sequenced with the 3'-overhang. FIG. 3 presents a heatmap of 96 molecular barcodes of 12, 13, or 14 nucleotides long, wherein each molecular barcode is followed by a 3'-overhang thymine (T). The shortest molecular barcodes are 12 nucleotides in length. Thus, all 96 molecular barcodes are base-composition balanced through the first 12 nucleotides. At position 13, sequencing adapters with the shortest (12 nucleotide) molecular barcodes will exhibit a signal for the 3'-overhang (T). To avoid an overwhelming T signal, molecular barcodes 13 or 14 nucleotides in length do not have a thymine at position 13. Similarly, at position 14, molecular barcodes 13 nucleotides in length with exhibit a signal for the constant 3'-overhang (T). Thus, to avoid an overwhelming T signal, molecular barcodes 14 nucleotides in length do not have a thymine at position 14.

Figure 4:
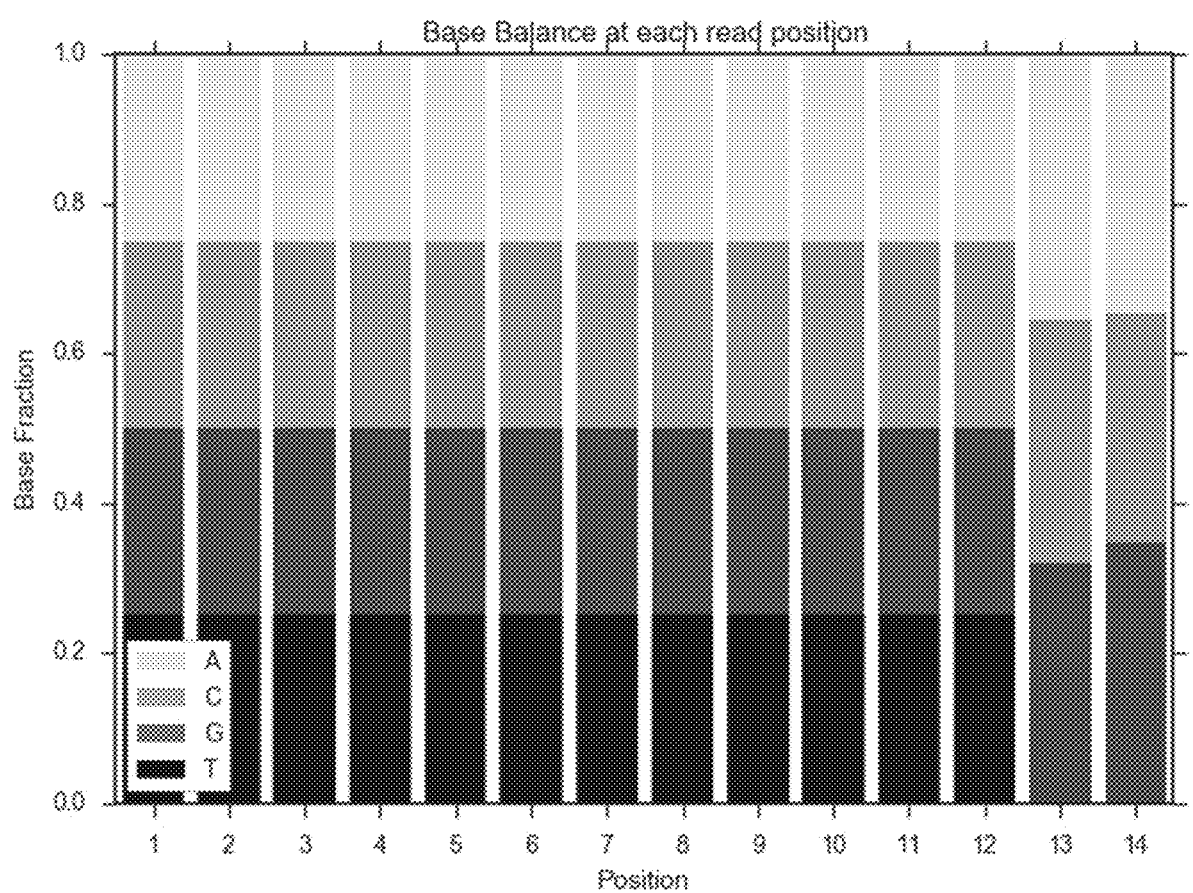
FIG. 4 provides one example of 96 base-composition balanced molecular barcodes of 12, 13, or 14 nucleotides in length, with a constant 3'-overhang thymine nucleotide adjacent to the molecular barcode. Due to the constant 3'-overhang thymine following each of the molecular barcodes, thymine is omitted at positions 13 and 14.

In some embodiments, the proportion of any given nucleotide (e.g., A, T, C, or G) at any given position of the molecular barcode amongst the plurality of sequence adapters is between about 0.2 and about 0.3 (such as about 0.25) at the corresponding position relative to the shortest molecular barcode in the plurality of sequencing adapters, and between about 0.25 and about 0.4 (such as about 0.33) for any given nucleotide other than the constant 3'-overhang nucleotide at any position beyond the length of the shortest molecular barcode. FIG. 4 provides one example of 96 base-composition balanced molecular barcodes of 12, 13, or 14 nucleotides in length, with a constant 3'-overhang thymine nucleotide adjacent to the molecular barcode (i.e., at the 13th position for a molecular barcode of 12 nucleotides in length, at the 14th position for a molecular barcode of 13 nucleotides in length, and at the 15th position for a molecular barcode 14 nucleotides in length). As can be seen in FIG. 4, the proportion (i.e., base fraction) for each of T, G, C, and A is about 0.25 for each of positions 1-12. Starting at position 13, a thymine nucleotide signal is given for each nucleic acid molecule having a molecular barcode 12 nucleotides in length. Thus, thymine is omitted for the longer molecular barcodes, and the proportion for each of G, C, and A is about 0.33 for each of position 13 or 14.

Figure 5:
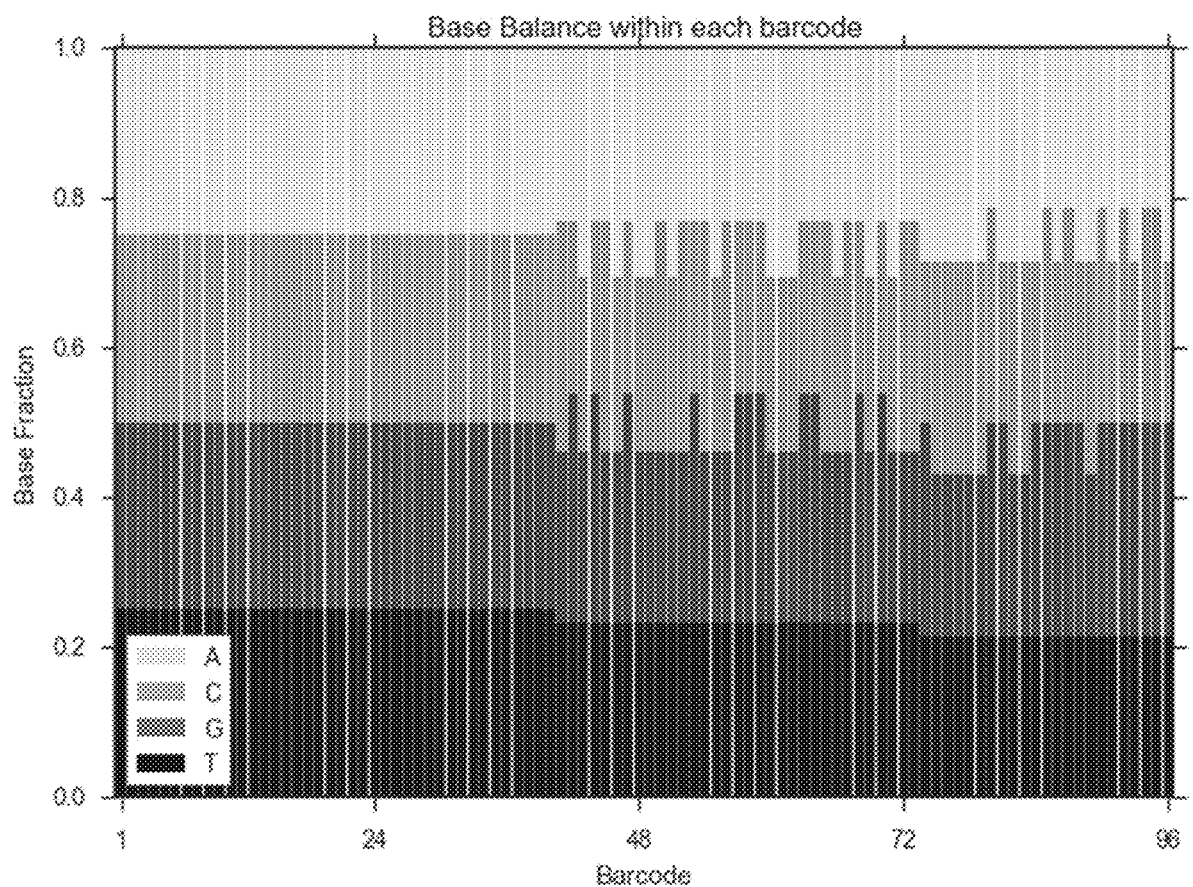
FIG. 5 illustrates the base fraction within a given molecular barcode for an exemplary set of 96 molecular barcodes.

Laser-color balancing and base-composition balancing within any given molecular barcode can be determined by counting the fraction of different nucleotide types within any molecular barcode. Base-composition balance need not be precisely balanced. For example, in molecular barcodes with a length not divisible by 4, an imperfect balance is inevitable. FIG. 5 illustrates the base fraction within a given molecular barcode for an exemplary set of 96 molecular barcodes.

In some embodiments, the molecular barcodes include additional engineering features to enhance the sequencing quality. For example, in some embodiments, the molecular barcodes do not comprise homopolymer sequences (such as three or more consecutive, identical nucleotides; three or more consecutive, identical nucleotides; four or more consecutive, identical nucleotides; five or more consecutive, identical nucleotides; or six or more consecutive, identical nucleotides). In some embodiments, the molecular barcodes are non-self-complementary (i.e., a single strand of the molecular barcode is not complementary to itself, for example a hairpin structure).

The sequencing adapter optionally further comprises a sample index. The sample index can be used to identify the sample of origin of each read, and allows pooling of multiple samples during the same sequencing run. Thus, the sample index is the same for each sequencing adapter when the sequencing adapter is ligated to the nucleic acid molecules, and different samples can be pooled together after ligation. Pooling of samples can occur, for example, prior to any amplification or sequencing of the nucleic acids.

Figure 6:
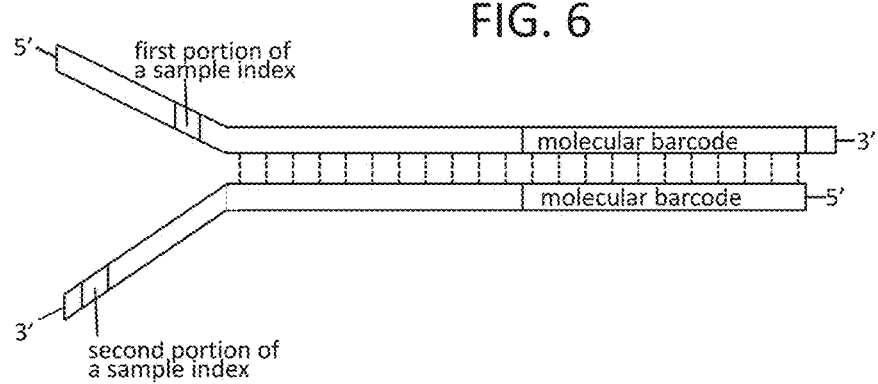
FIG. 6 illustrates an exemplary sequencing adapter comprising a sample index, wherein the sample index comprises a first portion on a first strand, and a second portion on a second strand.

The sample index can be of any length, for example between about 6 nucleotides and about 24 nucleotides in length (such as between about 6 nucleotides and about 12 nucleotides, between about 8 nucleotides and about 16 nucleotides, between about 12 nucleotides and about 26 nucleotides, or about 16 nucleotides and about 24 nucleotides in length). In some embodiments, the sample index comprises a first portion and a second portion, which may be on the same strand or on differing strands of the sequencing adapter. In some embodiments, the first portion of the sample index or the second portion of the sample index is between about 3 nucleotides and about 12 nucleotides in length (such as between about 3 nucleotides and about 6 nucleotides, between about 6 nucleotides and about 8 nucleotides, between about 8 nucleotides and about 10 nucleotides, or about 10 nucleotides and about 12 nucleotides in length). In some embodiments, the first portion of the sample index and the second portion of the sample index are of equal length. FIG. 6 illustrates an exemplary sequencing adapter comprising a sample index, wherein the sample index comprises a first portion on a first strand, and a second portion on a second strand.

In some embodiments, the sample index is laser-color balanced with the sample index. For example, in some embodiments, the ratio of A/C to G/T nucleotides within any given sample index is between about 2:1 and about 1:2 (such as about 1:1). In some embodiments, the sample index is base composition balanced within the sample index. For example, in some embodiments, the proportion of adenine within the sample index is between about 0.2 and about 0.4 (such as between about 0.2 and about 0.3, or about 0.25); the proportion of cytosine within the sample index is between about 0.2 and about 0.4 (such as between about 0.2 and about 0.3, or about 0.25); the proportion of thymine within the sample index is between about 0.2 and about 0.4 (such as between about 0.2 and about 0.3, or about 0.25); and the proportion of guanine within the sample index is between about 0.2 and about 0.4 (such as between about 0.2 and about 0.3, or about 0.25).

In some embodiments, the sample index includes additional engineering features to enhance the sequencing quality. For example, in some embodiments, the sample index does not comprise homopolymer sequences (such as two or more consecutive, identical nucleotides; three or more consecutive, identical nucleotides; four or more consecutive, identical nucleotides; five or more consecutive, identical nucleotides; or six or more consecutive, identical nucleotides). In some embodiments, the sample index is non-self-complementary (i.e., the sample index is not complementary to itself, for example the sample index is not a hairpin structure).

In some embodiments, two or more sequencing libraries are pooled, wherein the nucleic acid molecules are ligated to a sequencing adapter and wherein the individual sequencing libraries are identifiable by a unique sample index. In some embodiments, the sample indices an edit distance of 2 or more, 3 or more, 4 or more, 5 or more, 6 or more, 7 or more, or 8 or more from any other unique sample index.

Figure 7A:
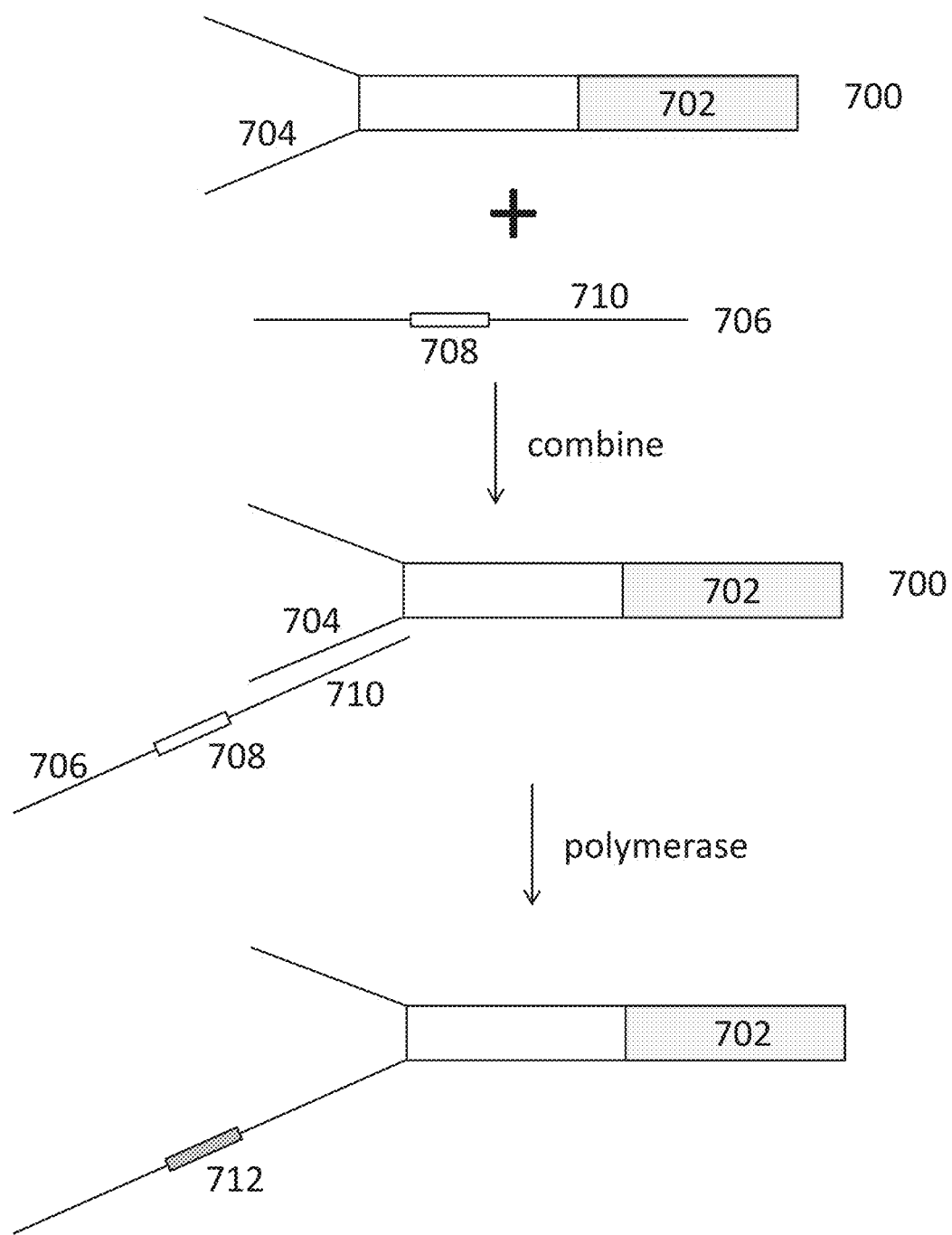
FIG. 7A illustrates one exemplary method of inserting a sample index into a sequencing adapter.

In some embodiments, the sample index is incorporated into a plurality of sequencing adapters by combining the sequencing adapters comprising a molecular barcode with an oligonucleotide comprising the complement sequence of a sample index. The oligonucleotide further comprises a complementation region, which is complementary to a portion of a non-complementary region of the sequencing adapter. Thus, once combined, the oligonucleotide pairs with the adapter sequence, and the sample index can be incorporated using a DNA polymerase. FIG. 7A illustrates one exemplary method of inserting a sample index into a sequencing adapter. A sequencing adapter 700 comprises a duplex molecular barcode 702 and a non-duplexed region 704. The sequencing adapter 700 is combined with an oligonucleotide 706, which comprises a sequence complementary to the sample index 708 and a complementation region 710. The complementation region 710 is complementary to the non-duplexed region 704. By employing a DNA polymerase (for example, by using polymerase chain reaction), the non-duplex region 704 is extended and complementary to the non-paired portion of the oligonucleotide 706, to yield the sample index 712. The sequencing adapter can then be combined with nucleic acid molecules, ligated, and sequenced.

Figure 7B:
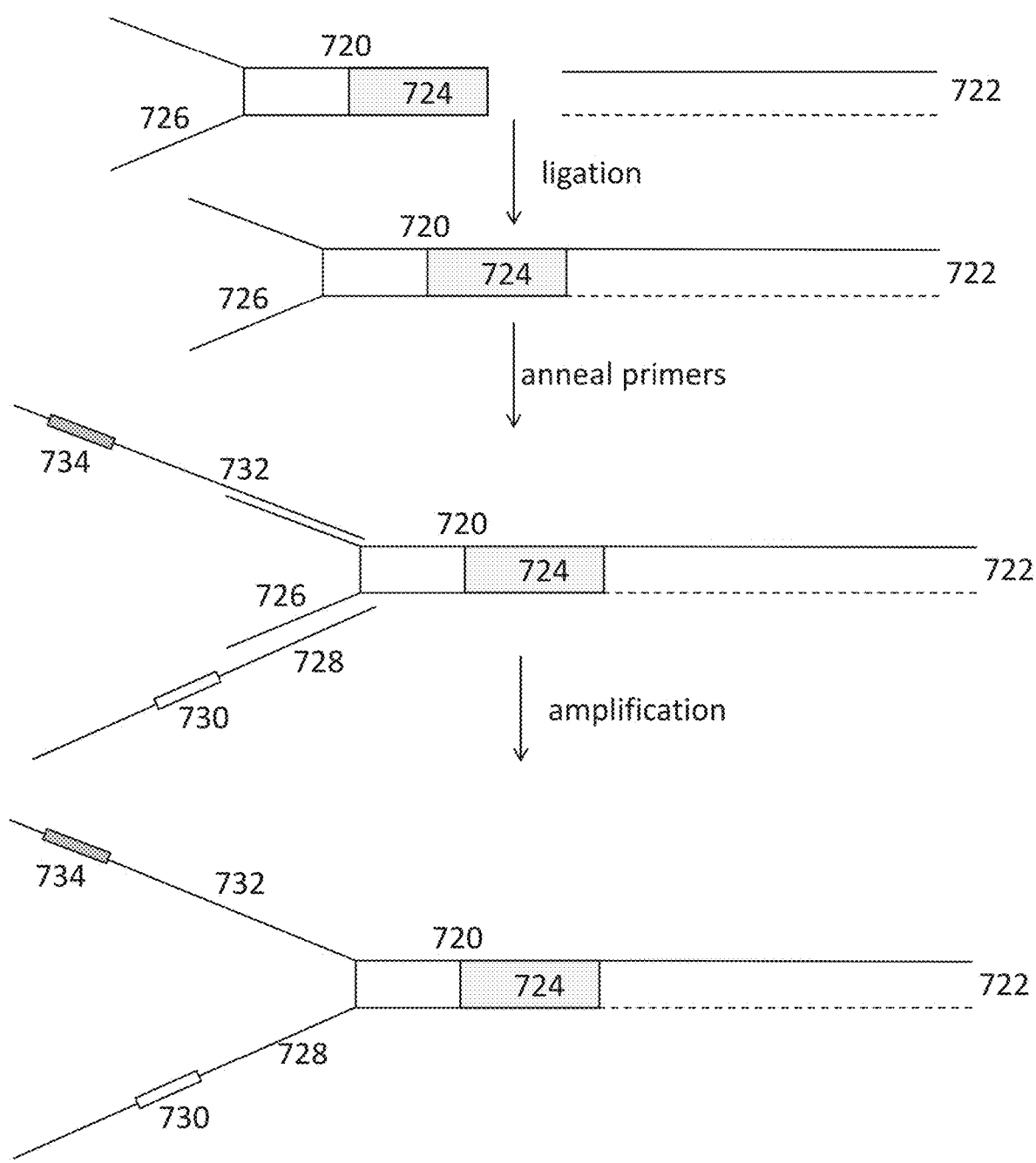
FIG. 7B illustrates another exemplary method of inserting a sample index into a sequencing adapter, wherein the sample index comprises a first portion and a second portion.

FIG. 7B illustrates another exemplary method of inserting a sample index in a sequencing adapter. In this exemplary method, the sequencing adapter 720 without the sample index is ligated to a nucleic acid molecule 722. The sequencing adapter 720 includes a duplex molecular barcode 724 and a primer annealing site 726. An amplification primer 728 comprising a sample index (or first portion thereof) 730 is then combined with the nucleic acid molecule 722 ligated to the sequencing adapter 720. A reverse amplification primer 732 comprising a complement sample index (or a second portion of a sample index) 734 is also combined with the nucleic acid molecule 722 ligated to the sequencing adapter 720. The amplification primer is complementary to a primer annealing on the adapter. Upon amplification, the sample index is included in the sequencing adapter.

In some embodiments, there is provided a composition comprising a plurality of sequencing adapters comprising a duplex molecular barcode having a nondegenerate sequence. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof.

In some embodiments, there is provided a composition comprising a plurality of sequencing adapters comprising a duplex molecular barcode having a nondegenerate sequence, wherein the plurality of sequencing adapters comprises a first sequencing adapter comprising a first duplex molecular barcode n nucleotides in length; and a second sequencing adapter comprising a second duplex molecular barcode n+x nucleotides in length, wherein x is not zero. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof.

In some embodiments, there is provided a composition comprising a plurality of sequencing adapters comprising a duplex molecular barcode having a nondegenerate sequence and a constant 3'-overhang (such as a thymine nucleotide), wherein the plurality of sequencing adapters comprises a first sequencing adapter comprising a first duplex molecular barcode n nucleotides in length; and a second sequencing adapter comprising a second duplex molecular barcode n+x nucleotides in length, wherein x is not zero. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof.

In some embodiments, there is provided a composition comprising a plurality of sequencing adapters comprising a duplex molecular barcode having a nondegenerate sequence and a constant 3'-overhang (such as a thymine nucleotide), wherein the plurality of sequencing adapters comprises a first sequencing adapter comprising a first duplex molecular barcode n nucleotides in length; and a second sequencing adapter comprising a second duplex molecular barcode n+x nucleotides in length, wherein x is not zero; and wherein the number of unique molecular barcodes in the plurality of sequencing adapters is between 2 and about 500 (such as between about 10 and about 400, between about 40 and about 200, between about 80 and 120, or about 96). In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof.

In some embodiments, there is provided a composition comprising a plurality of sequencing adapters comprising a duplex molecular barcode having a nondegenerate sequence and a constant 3'-overhang (such as a thymine nucleotide), wherein the plurality of sequencing adapters comprises a first sequencing adapter comprising a first duplex molecular barcode n nucleotides in length; and a second sequencing adapter comprising a second duplex molecular barcode n+x nucleotides in length, wherein x is not zero; wherein the number of unique molecular barcodes in the plurality of sequencing adapters is between 2 and about 500 (such as between about 10 and about 400, between about 40 and about 200, between about 80 and 120, or about 96); and wherein the molecular barcodes are color balanced at the corresponding position relative to the shortest molecular barcode in the plurality of sequencing adapters. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof.

In some embodiments, there is provided a composition comprising a plurality of sequencing adapters comprising a duplex molecular barcode having a nondegenerate sequence and a constant 3'-overhang (such as a thymine nucleotide), wherein the plurality of sequencing adapters comprises a first sequencing adapter comprising a first duplex molecular barcode n nucleotides in length; and a second sequencing adapter comprising a second duplex molecular barcode n+x nucleotides in length, wherein x is not zero; wherein the number of unique molecular barcodes in the plurality of sequencing adapters is between 2 and about 500 (such as between about 10 and about 400, between about 40 and about 200, between about 80 and 120, or about 96); and wherein the molecular barcodes are base-composition balanced at the corresponding position relative to the shortest molecular barcode in the plurality of sequencing adapters. In some embodiments, the edit distance between each molecular barcode is 2 or more. In some embodiments, the sequencing adapters comprise a sample index. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof.

In some embodiments, there is provided a composition comprising a first sequencing adapter comprising a first duplex molecular barcode n nucleotides in length; and a second sequencing adapter comprising a second duplex molecular barcode n+x nucleotides in length, wherein x is not zero. In some embodiments, the edit distance between each molecular barcode is 2 or more. In some embodiments, the sequencing adapters comprise a sample index (which may be included in the sequencing adapter before ligation or incorporated into the sequencing adapter during amplifica-tion). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof.

In some embodiments, there is provided a composition comprising a first sequencing adapter comprising a first duplex molecular barcode n nucleotides in length and a constant 3'-overhang (such as a thymine nucleotide); and a second sequencing adapter comprising a second duplex molecular barcode n+x nucleotides in length and the constant 3'-overhang, wherein x is not zero. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof.

In some embodiments, there is provided a composition comprising a first sequencing adapter comprising a first duplex molecular barcode n nucleotides in length and a constant 3'-overhang (such as a thymine nucleotide); and a second sequencing adapter comprising a second duplex molecular barcode n+x nucleotides in length and the constant 3'-overhang, wherein x is not zero; and wherein the number of unique molecular barcodes in the plurality of sequencing adapters is between 2 and about 500 (such as between about 10 and about 400, between about 40 and about 200, between about 80 and 120, or about 96). In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof.

In some embodiments, there is provided a composition comprising a first sequencing adapter comprising a first duplex molecular barcode n nucleotides in length and a constant 3'-overhang (such as a thymine nucleotide); and a second sequencing adapter comprising a second duplex molecular barcode n+x nucleotides in length and the constant 3'-overhang, wherein x is not zero; wherein the number of unique molecular barcodes in the plurality of sequencing adapters is between 2 and about 500 (such as between about 10 and about 400, between about 40 and about 200, between about 80 and 120, or about 96); and wherein the molecular barcodes are color balanced at the corresponding position relative to the shortest molecular barcode in the plurality of sequencing adapters. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof.

In some embodiments, there is provided a composition comprising a first sequencing adapter comprising a first duplex molecular barcode n nucleotides in length and a constant 3'-overhang (such as a thymine nucleotide); and a second sequencing adapter comprising a second duplex molecular barcode n+x nucleotides in length and the constant 3'-overhang, wherein x is not zero; wherein the number of unique molecular barcodes in the plurality of sequencing adapters is between 2 and about 500 (such as between about 10 and about 400, between about 40 and about 200, between about 80 and 120, or about 96); and wherein the molecular barcodes are base-composition balanced at the corresponding position relative to the shortest molecular barcode in the plurality of sequencing adapters. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof.

In some embodiments, there is provided a nucleic acid sequencing library comprising a plurality of nucleic acid inserts ligated to at least one (such as two) sequencing adapter randomly selected from a plurality of sequencing adapters comprising a duplex molecular barcode having a nondegenerate sequence. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof.

In some embodiments, there is provided a nucleic acid sequencing library comprising a plurality of nucleic acid inserts ligated to at least one (such as two) sequencing adapter randomly selected from a plurality of sequencing adapters comprising a duplex molecular barcode having a nondegenerate sequence, wherein the plurality of sequencing adapters comprises a first sequencing adapter comprising a first duplex molecular barcode n nucleotides in length; and a second sequencing adapter comprising a second duplex molecular barcode n+x nucleotides in length, wherein x is not zero. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof.

In some embodiments, there is provided a nucleic acid sequencing library comprising a plurality of nucleic acid inserts ligated to at least one (such as two) sequencing adapter randomly selected from a plurality of sequencing adapters comprising a duplex molecular barcode having a nondegenerate sequence and a constant 3'-overhang (such as a thymine nucleotide), wherein the plurality of sequencing adapters comprises a first sequencing adapter comprising a first duplex molecular barcode n nucleotides in length; and a second sequencing adapter comprising a second duplex molecular barcode n+x nucleotides in length, wherein x is not zero. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof.

In some embodiments, there is provided a nucleic acid sequencing library comprising a plurality of nucleic acid inserts ligated to at least one (such as two) sequencing adapter randomly selected from a plurality of sequencing adapters comprising a duplex molecular barcode having a nondegenerate sequence and a constant 3'-overhang (such as a thymine nucleotide), wherein the plurality of sequencing adapters comprises a first sequencing adapter comprising a first duplex molecular barcode n nucleotides in length; and a second sequencing adapter comprising a second duplex molecular barcode n+x nucleotides in length, wherein x is not zero; and wherein the number of unique molecular barcodes in the plurality of sequencing adapters is between 2 and about 500 (such as between about 10 and about 400, between about 40 and about 200, between about 80 and 120, or about 96). In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof.

In some embodiments, there is provided a nucleic acid sequencing library comprising a plurality of nucleic acid inserts ligated to at least one (such as two) sequencing adapter randomly selected from a plurality of sequencing adapters comprising a duplex molecular barcode having a nondegenerate sequence and a constant 3'-overhang (such as a thymine nucleotide), wherein the plurality of sequencing adapters comprises a first sequencing adapter comprising a first duplex molecular barcode n nucleotides in length; and a second sequencing adapter comprising a second duplex molecular barcode n+x nucleotides in length, wherein x is not zero; wherein the number of unique molecular barcodes in the plurality of sequencing adapters is between 2 and about 500 (such as between about 10 and about 400, between about 40 and about 200, between about 80 and 120, or about 96); and wherein the molecular barcodes are color balanced at the corresponding position relative to the shortest molecular barcode in the plurality of sequencing adapters. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof.

In some embodiments, there is provided a nucleic acid sequencing library comprising a plurality of nucleic acid inserts ligated to at least one (such as two) sequencing adapter randomly selected from a plurality of sequencing adapters comprising a duplex molecular barcode having a nondegenerate sequence and a constant 3'-overhang (such as a thymine nucleotide), wherein the plurality of sequencing adapters comprises a first sequencing adapter comprising a first duplex molecular barcode n nucleotides in length; and a second sequencing adapter comprising a second duplex molecular barcode n+x nucleotides in length, wherein x is not zero; wherein the number of unique molecular barcodes in the plurality of sequencing adapters is between 2 and about 500 (such as between about 10 and about 400, between about 40 and about 200, between about 80 and 120, or about 96); and wherein the molecular barcodes are base-composition balanced at the corresponding position relative to the shortest molecular barcode in the plurality of sequencing adapters. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof.

In some embodiments, there is provided a nucleic acid sequencing library comprising a plurality of nucleic acid inserts ligated to at least one (such as two) sequencing adapter randomly selected from a plurality of sequencing adapters comprising a first sequencing adapter comprising a first duplex molecular barcode n nucleotides in length; and a second sequencing adapter comprising a second duplex molecular barcode n+x nucleotides in length, wherein x is not zero. In some embodiments, the edit distance between each molecular barcode is 2 or more. In some embodiments, the sequencing adapters comprise a sample index. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof.

In some embodiments, there is provided a nucleic acid sequencing library comprising a plurality of nucleic acid inserts ligated to at least one (such as two) sequencing adapter randomly selected from a plurality of sequencing adapters comprising a first duplex molecular barcode n nucleotides in length and a constant 3'-overhang (such as a thymine nucleotide); and a second sequencing adapter comprising a second duplex molecular barcode n+x nucleotides in length and the constant 3'-overhang, wherein x is not zero. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof.

In some embodiments, there is provided a nucleic acid sequencing library comprising a plurality of nucleic acid inserts ligated to at least one (such as two) sequencing adapter randomly selected from a plurality of sequencing adapters comprising a first sequencing adapter comprising a first duplex molecular barcode n nucleotides in length and a constant 3'-overhang (such as a thymine nucleotide); and a second sequencing adapter comprising a second duplex molecular barcode n+x nucleotides in length and the constant 3'-overhang, wherein x is not zero; and wherein the number of unique molecular barcodes in the plurality of sequencing adapters is between 2 and about 500 (such as between about 10 and about 400, between about 40 and about 200, between about 80 and 120, or about 96). In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof.

In some embodiments, there is provided a nucleic acid sequencing library comprising a plurality of nucleic acid inserts ligated to at least one (such as two) sequencing adapter randomly selected from a plurality of sequencing adapters comprising a first sequencing adapter comprising a first duplex molecular barcode n nucleotides in length and a constant 3'-overhang (such as a thymine nucleotide); and a second sequencing adapter comprising a second duplex molecular barcode n+x nucleotides in length and the constant 3'-overhang, wherein x is not zero; wherein the number of unique molecular barcodes in the plurality of sequencing adapters is between 2 and about 500 (such as between about 10 and about 400, between about 40 and about 200, between about 80 and 120, or about 96); and wherein the molecular barcodes are color balanced at the corresponding position relative to the shortest molecular barcode in the plurality of sequencing adapters. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof.

In some embodiments, there is provided a nucleic acid sequencing library comprising a plurality of nucleic acid inserts ligated to at least one (such as two) sequencing adapter randomly selected from a plurality of sequencing adapters comprising a first sequencing adapter comprising a first duplex molecular barcode n nucleotides in length and a constant 3'-overhang (such as a thymine nucleotide); and a second sequencing adapter comprising a second duplex molecular barcode n+x nucleotides in length and the constant 3'-overhang, wherein x is not zero; wherein the number of unique molecular barcodes in the plurality of sequencing adapters is between 2 and about 500 (such as between about 10 and about 400, between about 40 and about 200, between about 80 and 120, or about 96); and wherein the molecular barcodes are base-composition balanced at the corresponding position relative to the shortest molecular barcode in the plurality of sequencing adapters. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof.

Methods of Sequencing Nucleic Acid Molecules and Identifying Errors in Nucleic Acid Sequences The sequencing adapters described herein are useful in sequencing nucleic acid molecules in a sequencing library. A sequencing library can be prepared, for example, by forming fragments of DNA (for example, by shearing the DNA), and attaching the sequencing adapters to the DNA fragments. In some embodiments, the nucleic acid molecules in the sequencing library is cell-free DNA, such as cell-free fetal DNA (also referred to as "cfDNA") or circulating tumor DNA (also referred to as "cell-free tumor DNA," or "ctDNA"). ctDNA circulates in the blood of a cancer patient, and is generally pre-fragmented. cfDNA circulates in the blood of a pregnant mother, and represents the fetal genome. The fragments (for example, the ctDNA or fragments formed by fragmenting longer DNA strands) can be referred to as "inserts," as they can be "inserted" or ligated adjacent to a sequencing adapter. In some embodiments, the inserts are inserted between two sequencing adapters. RNA molecules can also be sequenced, for example by reverse transcribing the RNA molecules to form DNA molecules, which are attached to sequencing adapters.

Sequenced nucleic acid molecules can be used to identify variants in an allele relative to a wild-type or consensus sequence. Such variants can be, for example, a single nucleotide polymorphism (SNP), an insertion or deletion (indel), a copy-number variant, or protein fusion variant. Identification of such variants allows for the diagnosis of genetic disease, a tumor (for example, when sequencing ctDNA), or a fetal abnormality (for example, when sequencing cfDNA).

The sequencing library comprising the inserts can be combined with a composition comprising a plurality of sequencing adapters. The molecular barcodes in the sequencing adapters can be used to identify nucleic acid molecules in the sequencing library. In some embodiments, the sequence of the molecular barcode is predetermined (i.e., known) prior to combining the sequencing adapters with the nucleic acid molecules. In some embodiments, the sequence of the molecular barcode is nondegenerate.

The sequencing adapters are ligated to the nucleic acid molecules (i.e., "inserts") in the sequencing library, thereby forming a plurality of inserts bound to one or two sequencing adapters (that is, the each nucleic acid molecule can be ligated to a sequencing adapter at one end of the nucleic acid molecule or at both ends of the nucleic acid molecule). When the inserts in the sequencing library are amplified (for example, prior to sequencing), the molecular barcode is amplified with the insert in a full-length nucleic acid molecule.

In one aspect, there is provided a method of sequencing a duplex nucleic acid molecule, comprising sequencing a set of amplified first strands formed from a first strand of the duplex nucleic acid molecule, resulting in a set of first strand reads; constructing a nucleic acid molecule consensus sequence using the set of first strand reads; wherein the duplex nucleic acid molecule is randomly ligated to a sequencing adapter from a plurality of sequencing adapters comprising a molecular barcode having a nucleic acid duplex with a predetermined sequence.

In some embodiments, the plurality of sequencing adapters are combined with the duplex nucleic acid molecule and randomly ligated. Either one or two sequencing adapters can be ligated to the duplex nucleic acid molecule. In some embodiment, the sequencing adapter comprises a first constant 3'-overhang, and the duplex nucleic acid molecule comprises a second constant 3'-overhang complementary to the first constant 3'-overhang, as further described herein. The 3'-overhangs promote efficient ligation and limit ligation errors (such as self-ligation of sequencing adapters), although blunt end ligation is also contemplated.

In some embodiments, the duplex nucleic acid molecules ligated to the sequencing adapters are amplified, for example using polymerase chain reaction (PCR). In some embodiments, an amplification primer is combined with the duplex nucleic acids, which can bind to a primer annealing site (for example, a primer annealing site located in the non-complementary region of the sequencing adapter). In some embodiments, a high-fidelity DNA polymerase is used to amplify the nucleic acid molecules, for example a DNA polymerase with an error rate of about 1 error per 500,000 base pairs or less, or about 1 error per 1 million base pairs or less. In some embodiments, a low-fidelity DNA polymerase is used.

Nucleic acid molecules in the sequencing library can be enriched for those nucleic acid molecules comprising a portion of one or more regions of interest. The region of interest can be, for example, a non-coding region (such as a 5'-untranslated region, a 3'-untranslated region, or one or more introns), or one or more exons of a gene. In some embodiments, sequencing the region of interest includes generating a plurality of strand reads at various points along the region of interest. The strand reads can be aligned, for example by using a reference sequence, to build a consensus sequence for the region of interest. A set of capture probes (also referred to as a capture probe library) can be used to enrich a plurality of nucleic acid molecules (for example, in a sequencing library (which may or may not be amplified, for example using PCR). The capture probes comprise a nucleic acid sequence complementary to various portions within the region of interest. In some embodiments, a set of capture probes includes, for example, between about 2 and about 20,000 capture probes (such as between about 2 and about 50 capture probes, between about 50 and about 100 capture probes, between about 100 to about 250 capture probes, between about 250 and about 500 capture probes, between about 500 and about 1,000 capture probes, between about 1,000 and about 5,000 capture probes, between about 5,000 and about 10,000 capture probes, or between about 10,000 and about 20,000 capture probes) that can hybridize to different portions of the region of interest. A sequencing library can include nucleic acid molecules comprising a portion of the region of interest (for example, genomic DNA containing the region of interest can be fragmented into a plurality of nucleic acid molecules, with each nucleic acid molecule originating from the region of interest comprising a portion of the region of interest). A plurality of nucleic acid molecules (such as a sequencing library) can be combined with the capture probes, and nucleic acid molecules comprising a portion of the region of interest complementary to a capture probe can hybridize to the capture probe. A plurality of different capture probes within the set of capture probes can be used to enrich nucleic acid molecules from throughout the region of interest. The nucleic acid molecules binding the capture probes can then be separated from the remaining nucleic acid molecules (for example, nucleic acid molecules in the sequencing library other than those comprising a portion of the region of interest). For example, the capture probes can be conjugated to a molecular tag (such as biotin) and attached to a surface (such as a bead, for example a magnetic bead), which allows for separation of the nucleic acid molecules comprising a portion of the region of interest from those nucleic acid molecules that do not comprise a portion of the region of interest.

In some embodiments, the amplified nucleic acid molecules are enriched for a region of interest (such as a gene of interest). In some embodiments, the nucleic acid sequencing library is enriched for nucleic acid molecules comprising portions of one or more regions of interest, and the enriched nucleic acid molecules are then amplified. For example, in some embodiments, one or more capture probes are combined with the sequencing library or amplified nucleic acid molecules, and those nucleic acid molecules that hybridize to the capture probes can be selectively separated from those nucleic acid molecules that do not hybridize to the capture probes. By PCR amplifying after enriching for nucleic acid molecules having portions of the one or more regions of interest, amplified nucleic acid molecules will have the same sequencing adapter, including molecular barcode, as the parent nucleic acid molecule.

In some embodiments, the sequences of the capture probes are complementary to different portions of the target nucleic acid molecule containing the region of interest, thereby allowing the full region of interest to be enriched. The capture probes can be used to enrich a nucleic acid sequencing library which may or may not have been PCR amplified. For example, in some embodiments the nucleic acid sequencing library is enriched with a plurality of capture probes, and the enriched nucleic acid molecules (that is, those nucleic acid molecules that hybridized to the capture probes) are then PCR amplified. In some embodiments, the nucleic acid sequencing library is PCR amplified and then enriched using the plurality of capture probes.

An equal number of each capture probe in the set of capture probes can result in sequencing depth variation because some capture probes may more efficiently bind a particular fragment of a sequence of interest than another capture probe. This may be due, for example, to a variance in the concentration of the capture probe, variance in the concentration of the target nucleic acid molecule containing the region of interest, variations in the length of the capture probe and/or target nucleic acid molecule, or melting temperature of the capture probe (for example, due to variation in GC content within a region of interest). Large variance in sequencing depth can decrease overall sequence quality by limiting sensitivity and specificity in low sequencing depth sub-regions of a region of interest. Additionally, very deep sequencing of sub-regions is unlikely to result in any substantial increase in sequencing quality, but can add significant cost.

Sequencing can be performed using any known sequencing method, such as single-molecule real-time sequencing, ion semiconductor sequencing, pyrosequencing, massively parallel signature sequencing, or sequencing-by-synthesis chemistry. An exemplary method of sequencing-by-synthesis chemistry is performed using an Illumina HiSeq 2500® sequencer or an Illumina HiSeq 4000® sequencer. In some embodiments, sequencing is performed using an Illumina HiSeq3000® sequencer, and Illumina HiSeqX® sequencer, Roche 454® sequencer, or Life Technologies Ion Proton® sequencing systems. Other methods of sequencing are known in the art.

In some embodiments, the first strand of the duplex nucleic acid molecule is sequenced, resulting in a set of first strand reads. In some embodiments, the first strand of the duplex nucleic acid molecule is sequenced, resulting in a set of first strand reads, and the second strand of the duplex nucleic acid molecule is sequencing, resulting in a set of second strand reads. The nucleic acid strands can be read in a single direction or in both directions (also referred to as "pair-wise sequencing" or "bothdirs"). Thus, a duplex nucleic acid molecule can be sequenced in one of at least four modes: (1) a first strand of the duplex nucleic acid molecule is sequenced in a single direction; (2) a first strand of the duplex nucleic acid molecule is sequenced in both directions (i.e., a "bothdir" or "paired-end sequencing"); (3) a first strand of the duplex nucleic acid molecule is sequenced in a single direction, and a second strand of the duplex nucleic acid molecule is sequenced in a single direction; or (4) a first strand of the duplex nucleic acid molecule is sequenced in both directions, and the second strand of the duplex nucleic acid molecule is sequenced in both directions. Sequencing in both directions allows a given sequence to be sequenced twice. The duplicative sequencing is facilitated by shorter nucleic acid inserts. For example, cell-free DNA can be comprised of fragments smaller than the maximum length of a sequencing read, thereby allowing duplicative coverage. Long nucleic acid fragments, however, may not be able to obtain duplicative coverage, as sequencing in both directions will not result in substantial overlap. The number of sequencing observations for a strand of duplex nucleic acid molecule depends, in part, on the design of the experiment, the level of PCR amplification, and the depth of sequencing.

Four different modes of sequencing are illustrated in FIG. 17A-E. FIG. 17A illustrates a duplex nucleic acid molecule, for example from a nucleic acid sequencing library. The duplex nucleic acid molecule includes a first strand ("+") and a second strand ("−"). As shown in FIG. 17B, both the first strand and the second strand are sequenced in both directions, using forward and reverse sequencing primers for each strand. Sequencing of both directions of a given nucleic acid strand is possible, for example, by amplifying the strand to form a complement (that is, a complement not arising from the original duplex nucleic acid molecule). Thus, both strands of the duplex nucleic acid molecule are sequenced in both directions. FIG. 17C shows sequencing in both directions using a forward and reverse sequencing primer for either the first strand ("+") or the second strand ("−"). This allows a single strand of a duplex nucleic acid molecule to be sequenced, but it does not sequence both strands of the duplex nucleic acid molecule. FIG. 17D shows sequencing in a single direction for both the first strand ("+") and the second strand ("−"). For example, sequencing could be performed using forward sequencing primers for the first strand and the second strand, or reverse sequencing primers for the first strand and the second strand. This allows both strands of the duplex nucleic acid molecule to be sequenced, but each strand is sequenced in a single direction. FIG. 17E shows a single strand (either the first strand ("+") or the second strand ("−")) of the duplex nucleic acid molecule being sequenced in a single direction. Sequencing both strands of a duplex nucleic acid molecule allows for detection of both chemical damage errors and sequencing errors. Sequencing in both directions of a given strand provides an additional layer of sequencing error detection, as the strand is sequenced in both directions and the resulting reads from both directions can be compared.

Once the sets of strand reads are generated, a consensus sequence can be generated using the set of strand reads. In some embodiments, the sets are compiled (that is, a strand read can be assigned to a set of strand reads). The sets can be compiled, for example, based on the similarity of the molecular barcodes in the strand reads, or both. The similarity can be determined, for example, using a sequence distance, an alignment to a reference genome, or a combination thereof.

Because a nucleic acid molecule can be ligated to up to two different sequencing adapters, the number of different molecular barcode combinations is $X^2$, where X is the number of unique molecular barcodes in the plurality of sequence adapters. In some embodiments, compiling the sets of strand reads on the basis of the molecular barcodes alone is insufficient, and the sequence of the nucleic acid molecule is also used to compile the sets (i.e., the full strand read). The probability that two different parent nucleic acid molecules having an identical or very high sequence identity will ligate to two identical molecular barcodes is extremely low. Further, the probability that two identical insert sequences bind to the same pair of molecular barcodes can be made lower by increasing the number of unique molecular barcodes. Thus, in some embodiments, both the sequence of the molecular barcodes and the sequence of the nucleic acid molecule inserts are used to compile the sets.

In some embodiments, sequence distance is used as a basis for compiling the sets of strand reads. For example, in some embodiments, sequence identity is used as a basis for compiling the sets of strand reads. Sequence identity can be used as a basis for compiling the sets of strand reads by requiring a first sequence to have a sequence identity to a second sequence above a predetermined threshold. For example, in some embodiments, the molecular barcodes must be an exact match (i.e., 100% identity), about 95% identity or higher, about 90% identity or higher, or about 85% or identity or higher to be compiled into the same set. In some embodiments, the strand reads must be about 99.9% identity or higher, about 99.8% identity or higher, about 99.5% identity or higher, about 99% identity or higher, about 95% identity or higher, or about 90% identity or higher to be compiled into the same set. In another example, edit distance can be used as a basis for compiling the sets of strand reads. For example, in some embodiments, the strand reads (or molecular barcode) must have an edit distance of 1 or less, 2 or less, 3 or less, 4 or less, 5 or less, 6 or less, 7 or less, 8 or less, 9 or less, 10 or less, 11 or less, 12 or less, 13 or less, 14 or less, or 15 or less to be compiled into the same set of strand reads. Other metrics that distinguish on the basis of sequence distance can also be used, such as Hamming distance, K-mer lookup tables, or probability models for sequencer errors. The sets can be identified using any grouping method, for example by using a cutoff threshold, clustering, hierarchical clustering, K-means clustering, or using a mixture model.

In some embodiments, alignment to a reference sequence is used to compile the sets of strand. For example, the sequence of strand read (which optionally excludes the molecular barcode), can be aligned to a known reference sequence. Based on the alignment location, the set of strand reads is compiled.

In some embodiments, a consensus sequence is constructed using the set of strand reads. In some embodiments, strand reads comprising variants are removed from the set before the consensus sequence is constructed. In some embodiments, a consensus sequence is constructed and compared to the strand reads, and strand reads that are inconsistent with the consensus sequence are removed from the set of strand reads. To sequence a nucleic acid library, a consensus sequence is constructed for each (or a subset of) the sets of strand reads.

In some embodiments, the consensus sequence is compared to the strand reads in the set of strand reads. Variants between the strand reads and the consensus sequence can be identified as errors that arose through laboratory manipulation (e.g., amplification or sequencing) or through chemical damage of the original nucleic acid molecules.

In some embodiments, a first strand consensus sequence is constructed for a first strand of a duplex nucleic acid molecule from a set of first strand reads, and a second strand consensus sequence is constructed for a second strand of the duplex nucleic acid molecule, wherein the first strand and the second strand are complementary. Chemical damage to a duplex nucleic acid molecule can result in a variant in one strand of a duplex nucleic acid molecule, but not the complementary strand of the duplex nucleic acid molecule. By comparing a consensus sequence for a nucleic acid strand to the consensus sequence for its complement, variants between the strands can be identified as chemical damage.

Figure 8:
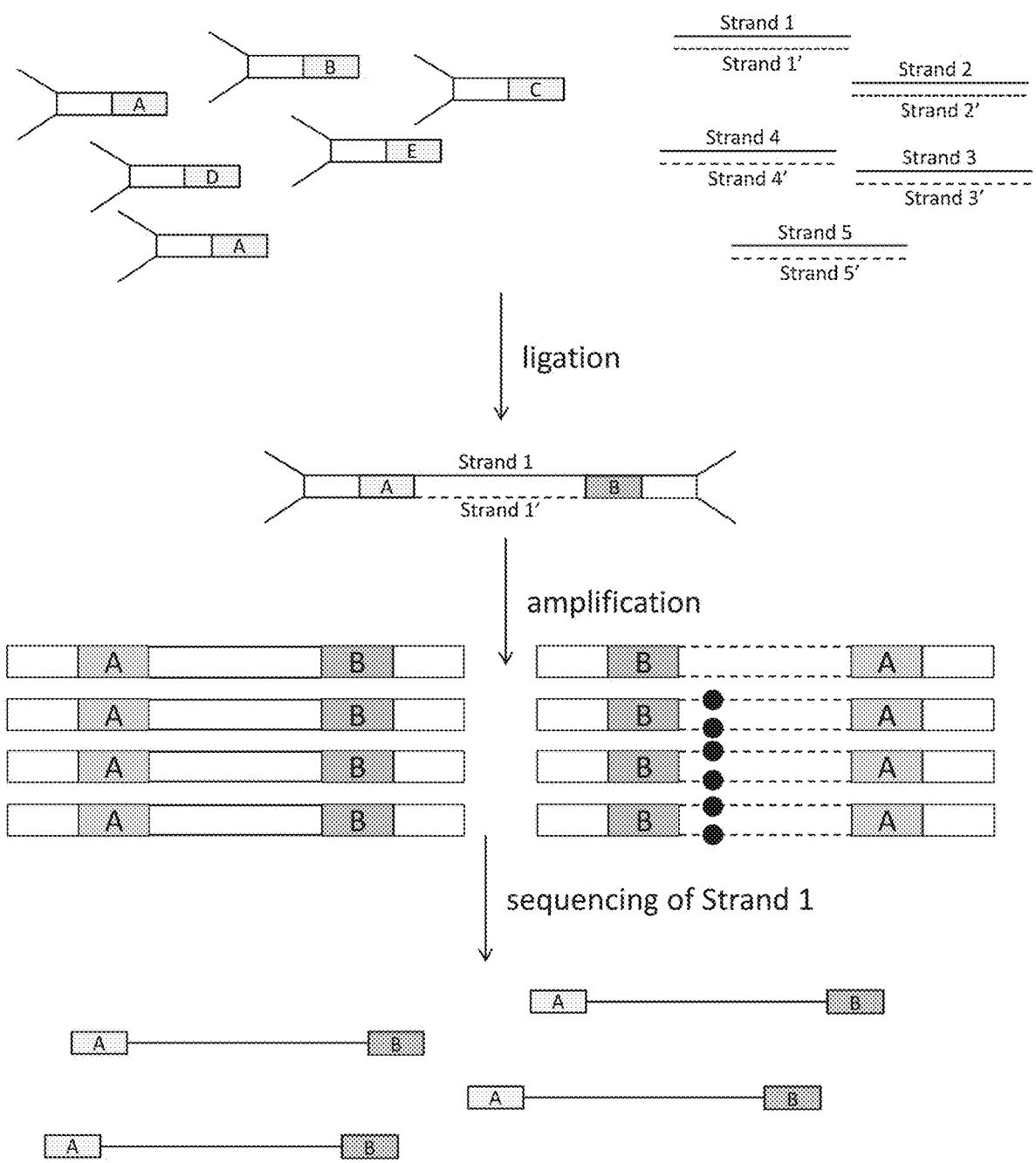
FIG. 8 illustrates one embodiment of a method of sequencing a duplex nucleic acid molecule.

FIG. 8 illustrates one embodiment of a method of sequencing a duplex nucleic acid molecule. A composition comprising a plurality of sequencing adapters is combined with a duplex nucleic acid molecule. The duplex nucleic acid molecule can be in a sequencing library comprising a plurality of duplex nucleic acid molecules. The sequencing adapters comprise the molecular barcode (marked by letters (A, B, C, etc.) to denote different sequences). The duplex nucleic acid molecule comprises a first strand (Strand 1, solid line) and a second strand (Strand 1', dashed line). As illustrated, the duplex nucleic acid molecules is in a sequencing library with a plurality of duplex nucleic acid molecules with a first strand (e.g., Strand 1, Strand 2, Strand 3, etc.) and a complementary second strand (e.g., Strand 1', Strand 2', Strand 3', etc.). The sequencing adapters are randomly ligated to the duplex nucleic acid. In the illustrated example, a sequencing adapter with a molecular barcode labeled "A" and "B" are ligated to the duplex nucleic acid with Strand 1 and Strand 1'. The duplex nucleic acid is then amplified to produce multiple copies of the duplex nucleic acid. Solely by way of example, a single-base mutation was introduced into the second set of strands Strand 1' during amplification (noted by a back circle). During amplification, the error is propagated. Thus, amplification yields Strand 1 and its complement, and Strand 1' and its complement (including errors that were incorporated during amplification). After amplification, the first strand (or both the first strand and the second strand) is sequenced, thereby generating a set of sequencing reads. A consensus sequence from the reads can then be generated using the set of Strand 1 reads, as shown in FIG. 9A.

Figure 9A:
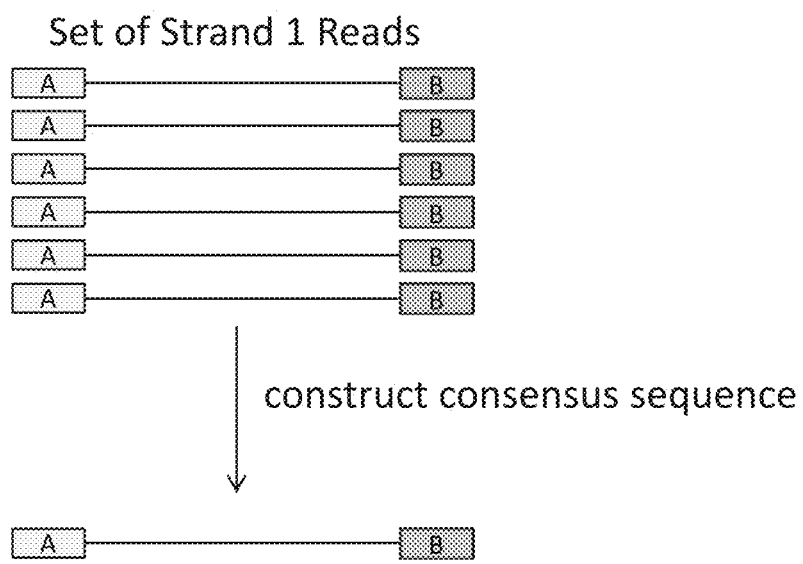
FIG. 9A illustrates an exemplary construction of a consensus sequence with a set of first strand reads from a duplex nucleic acid. Each strand read includes identical molecular barcodes, as each read arose from the same parent nucleic acid molecule.

Referring now to FIG. 9A, a consensus sequence is generated using the set of strand reads illustrated in FIG. 8. The molecular barcodes are identified, and the set of strand reads is compiled based on identity between the molecular barcodes, and a consensus sequence is constructed. Since the mutation occurs in the minority of strand reads, it is removed from the consensus sequence. Optionally, the consensus sequence is then compared to the set of strand reads, and variant strand reads are removed. Also optionally, an error-corrected consensus sequence can be constructed using the set of strand reads with the variant strand reads removed.

Figure 9B:
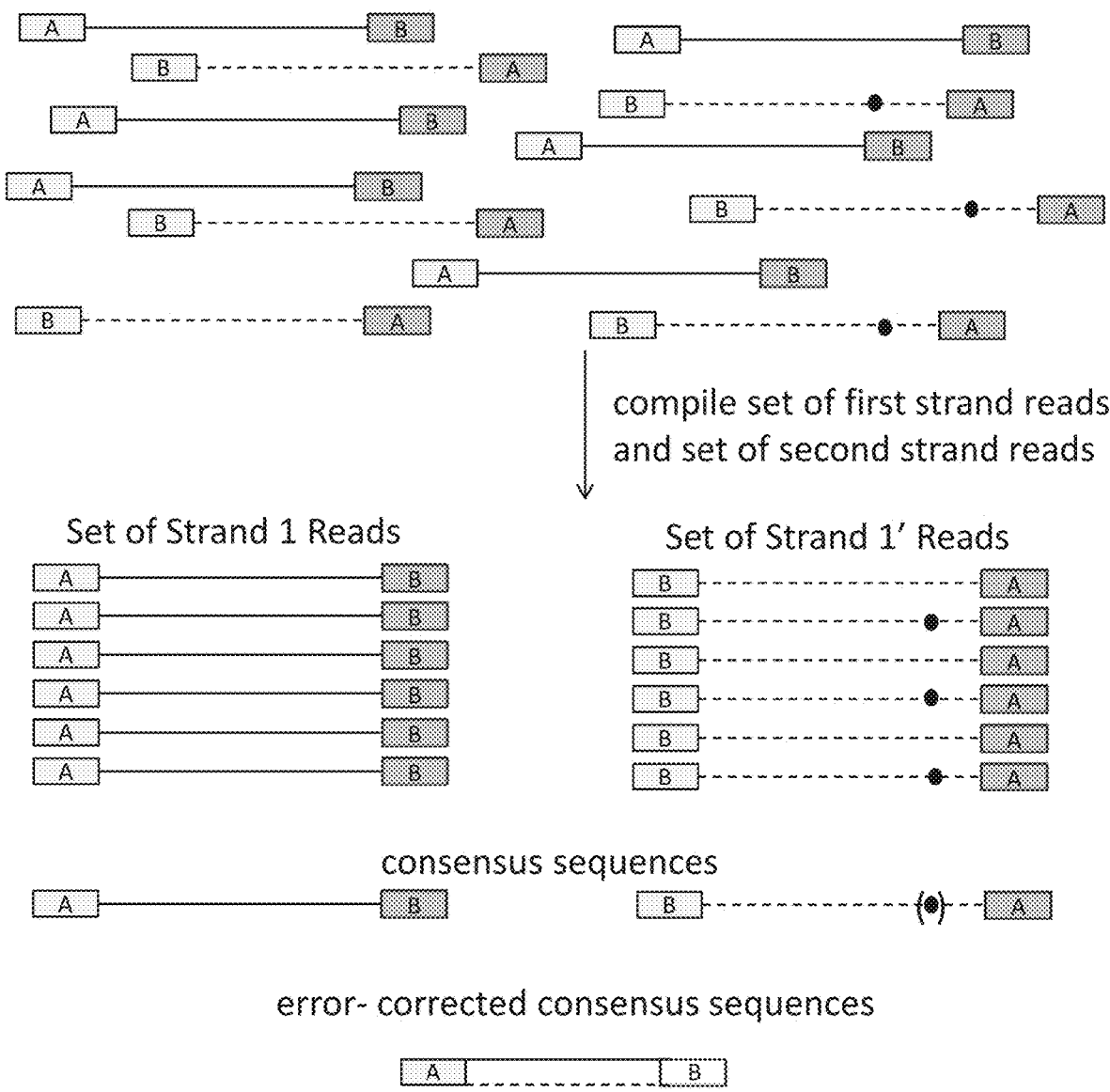
FIG. 9B illustrates an exemplary method of compiling of set of first strand reads and a set of second strand reads, wherein the first strand and the second strand are complementary strands from the same parent duplex nucleic acid molecule. Errors could have arisen in Strand 1', for example, during amplification.

Referring now to FIG. 9B, a set of first strand (Strand 1) reads and a set of second strand (Strand 1') reads are generated by sequencing both the first strand and the second strand, as generated using the process shown in FIG. 8. Solely by way of example, an error arose in Strand 1' during amplification, which was further propagated in both Strand 1' and its complement. Thus, when the consensus sequence for Strand 1' is constructed, it is not possible to determine the correct sequence at that location (indicated by the black dot surrounded by parenthesis). However, because there is variance in the sets of reads, it is possible to identify the location of an error. The consensus sequence from the set of first strand (Strand 1) reads can be compared to the consensus sequence from the set of second strand (Strand 1') reads or to the second strand reads in the set of second strand (Strand 1') reads to identify the error. The consensus sequence can also be compared to a reference sequence to identify the error. Optionally, consensus sequence can be aligned with a reference sequence to identify the error. Once the error is removed, an error corrected consensus sequence can be constructed, thereby generating an error corrected consensus sequence for the duplex nucleic acid.

Figure 9C:
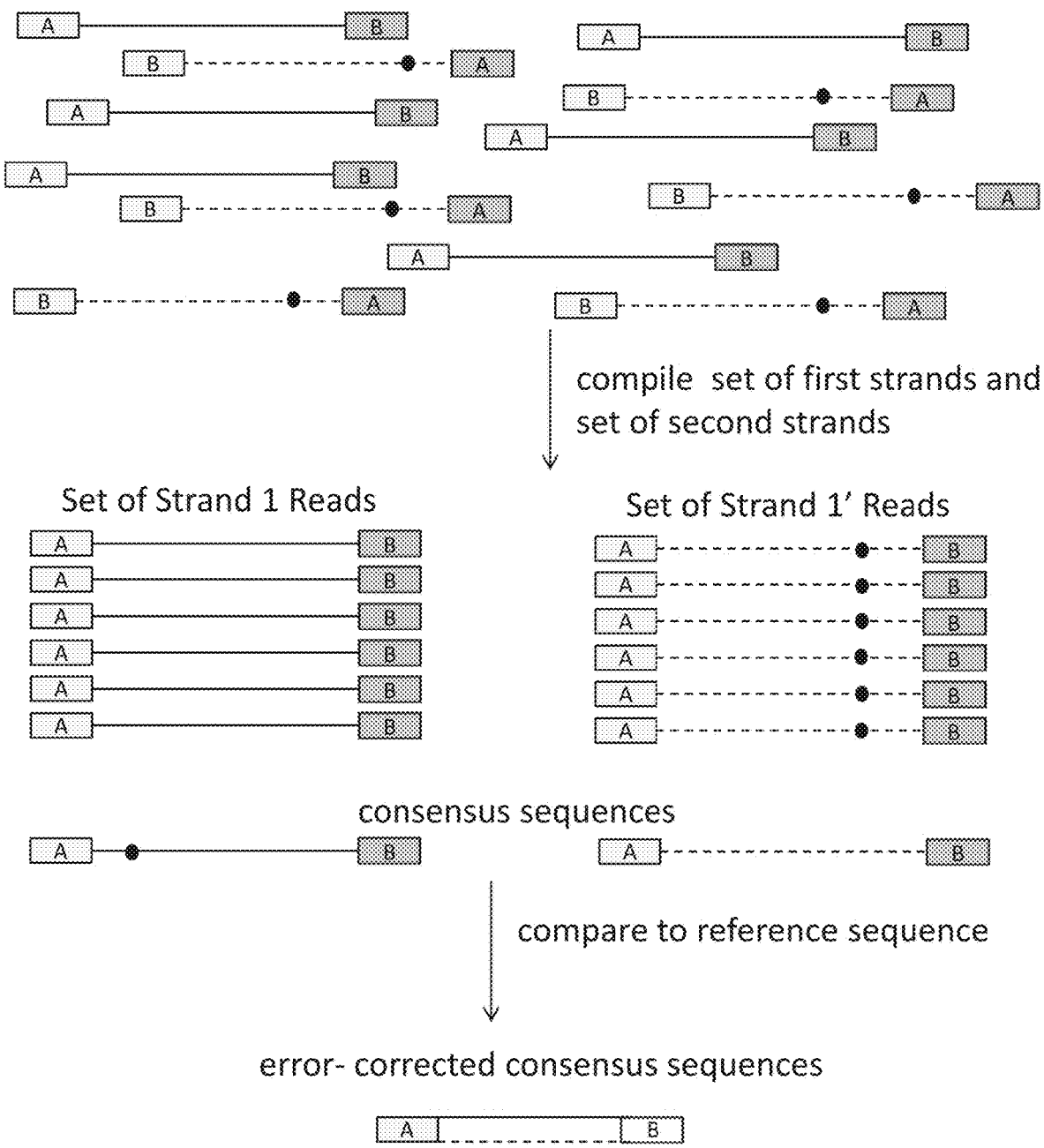
FIG. 9C illustrates another exemplary method of compiling of set of first strand reads and a set of second strand reads, wherein the first strand and the second strand are complementary strands from the same parent duplex nucleic acid molecule. Errors could have arisen in Strand 1', for example, prior to amplification, such as by chemical damage to the nucleic acid strand.

In FIG. 9C, Strand 1 includes an error at a base that arose prior to amplification, for example a chemical error in the parent nucleic acid molecule. Thus, the error was propagated when the nucleic acid molecule was amplified and sequenced. Thus all of the Strand 1' reads include this error. The complement strand, Strand 1, did not have this chemical error, and thus the base was correct when the parent nucleic acid molecule was amplified and the amplicons sequenced. Thus, the consensus sequence for Strand 1' includes the error, whereas the consensus sequence for Strand 1 does not include the error. If the error was a true variant in the original duplex nucleic acid, then both Strand 1 and Strand 1' would include the variant. Comparing the consensus sequence for Strand 1 with the consensus sequence for Strand 1' allows for identification of an error at that position, as only one of the consensus sequences include the error. The consensus sequences can be compared to a reference sequence to determine whether the consensus sequence for Strand 1 or the consensus sequence for Strand 1' gives the correct sequence.

The methods described herein can be useful for sequencing DNA sample from a subject. For example, blood sample can be taken from a subject, the DNA isolated from the blood, a sequence library formed by fragmenting the isolated DNA, and the DNA fragments sequenced using the molecular barcodes described herein. In some embodiments, the DNA sequencing library comprises cell-free DNA, such as ctDNA or cfDNA. In some embodiments, the fraction of cell-free DNA (such as ctDNA or cfDNA) relative to the total amount of DNA in the sample is about 0.001 to about 0.02 (such as about 0.001 to about 0.002, about 0.002 to about 0.003, about 0.003 to about 0.004, about 0.004 to about 0.005, about 0.005 to about 0.006, about 0.006 to about 0.008, about 0.008 to about 0.01, about 0.01 to about 0.012, about 0.012 to about 0.014, about 0.014 to about 0.016, or about 0.016 to about 0.02). In some embodiments, the fraction of ctDNA relative to the total amount of cell-free DNA in the sample is about 0.001 to about 0.02 (such as about 0.001 to about 0.002, about 0.002 to about 0.003, about 0.003 to about 0.004, about 0.004 to about 0.005, about 0.005 to about 0.006, about 0.006 to about 0.008, about 0.008 to about 0.01, about 0.01 to about 0.012, about 0.012 to about 0.014, about 0.014 to about 0.016, or about 0.016 to about 0.02). Because the fraction of cell-free DNA in a blood sample is generally small relative to the total amount of DNA in the blood sample, sensitive detection of sequence variants is often difficult using previous techniques. However, using the sequencing adapters and methods described herein, a sensitivity about 0.8 or higher can be obtained when the cell-free DNA fraction is about 0.0035 for higher for de novo mutations (that is, unknown sequence variants), and a sensitivity of about 0.8 or higher can be obtained when the cell-free DNA fraction is about 0.002 or higher for known mutations (that is, known sequence variants). In some embodiments, a sensitivity about 0.9 or higher can be obtained when the cell-free DNA fraction is about 0.005 for higher for de novo mutations, and a sensitivity of about 0.9 or higher can be obtained when the cell-free DNA fraction is about 0.003 or higher for known mutations. In some embodiments, a sensitivity about 0.95 or higher can be obtained when the cell-free DNA fraction is about 0.006 for higher for de novo mutations, and a sensitivity of about 0.95 or higher can be obtained when the cell-free DNA fraction is about 0.004 or higher for known mutations.

In some embodiments, there is provided a method of sequencing a nucleic acid molecule, comprising sequencing a set of amplified first strands formed from a first strand of a duplex nucleic acid molecule, resulting in a set of first strand reads; and constructing a first strand consensus sequence using the set of first strand reads; wherein the duplex nucleic acid molecule is ligated to a sequencing adapter prior to being amplified; and the sequencing adapter is randomly selected from a plurality of sequencing adapters comprising a duplex molecular barcode with a predetermined sequence. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecule is a cell-free DNA molecule, such as a ctDNA molecule or a cfDNA molecule.

In some embodiments, there is provided a method of sequencing a nucleic acid molecule, comprising sequencing a set of amplified first strands formed from a first strand of a duplex nucleic acid molecule, resulting in a set of first strand reads; compiling the set of first strand reads (for example, based on sequence distance or alignment to a reference sequence); and constructing a first strand consensus sequence using the set of first strand reads; wherein the duplex nucleic acid molecule is ligated to a sequencing adapter prior to being amplified; and the sequencing adapter is randomly selected from a plurality of sequencing adapters comprising a duplex molecular barcode with a predetermined sequence. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecule is a cell-free DNA molecule, such as a ctDNA molecule or a cfDNA molecule.

In some embodiments, there is provided a method of sequencing a nucleic acid molecule, comprising sequencing a set of amplified first strands formed from a first strand of a duplex nucleic acid molecule, resulting in a set of first strand reads; compiling the set of first strand reads (for example, based on sequence distance or alignment to a reference sequence); comparing the first strand reads in the set of first strand reads; identifying and removing errors in the set of first strand reads; and constructing an error-corrected first-strand consensus sequence; wherein the duplex nucleic acid molecule is ligated to a sequencing adapter prior to being amplified; and the sequencing adapter is randomly selected from a plurality of sequencing adapters comprising a duplex molecular barcode with a predetermined sequence. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecule is a cell-free DNA molecule, such as a ctDNA molecule or a cfDNA molecule.

In some embodiments, there is provided a method of sequencing a nucleic acid molecule, comprising sequencing a set of amplified first strands formed from a first strand of a duplex nucleic acid molecule, resulting in a set of first strand reads; compiling the set of first strand reads (for example, based on sequence distance or alignment to a reference sequence); constructing a first strand consensus sequence from the set of first strand reads; comparing the first strand consensus sequence to the set of first strand reads; identifying and removing errors in the set of first strand reads; and constructing an error-corrected first strand consensus sequence; wherein the duplex nucleic acid molecule is ligated to a sequencing adapter prior to being amplified; and the sequencing adapter is randomly selected from a plurality of sequencing adapters comprising a duplex molecular barcode with a predetermined sequence. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecule is a cell-free DNA molecule, such as a ctDNA molecule or a cfDNA molecule.

In some embodiments, there is provided a method of sequencing a nucleic acid molecule, comprising sequencing a set of amplified first strands formed from a first strand of a duplex nucleic acid molecule, resulting in a set of first strand reads; sequencing a set of amplified second strands formed from a second strand of the duplex nucleic acid molecule, resulting in a set of second strand reads; constructing a first strand consensus sequence using the set of first strand reads; and constructing a second strand consensus sequence using the set of second strand reads; wherein the duplex nucleic acid molecule is ligated to a sequencing adapter prior to being amplified; and the sequencing adapter is randomly selected from a plurality of sequencing adapters comprising a duplex molecular barcode with a predetermined sequence. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecule is a cell-free DNA molecule, such as a ctDNA molecule or a cfDNA molecule.

In some embodiments, there is provided a method of sequencing a nucleic acid molecule, comprising sequencing a set of amplified first strands formed from a first strand of a duplex nucleic acid molecule, resulting in a set of first strand reads; compiling the set of first strand reads (for example, based on sequence distance or alignment to a reference sequence); constructing a first strand consensus sequence using the set of first strand reads; sequencing a set of amplified second strands formed from a second strand of the duplex nucleic acid molecule, resulting in a set of second strand reads; compiling the set of second strand reads (for example, based on sequence distance or alignment to a reference sequence); and constructing a second strand consensus sequence using the set of first strand reads; wherein the duplex nucleic acid molecule is ligated to a sequencing adapter prior to being amplified; and the sequencing adapter is randomly selected from a plurality of sequencing adapters comprising a duplex molecular barcode with a predetermined sequence. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecule is a cell-free DNA molecule, such as a ctDNA molecule or a cfDNA molecule.

In some embodiments, there is provided a method of sequencing a nucleic acid molecule, comprising sequencing a set of amplified first strands formed from a first strand of a duplex nucleic acid molecule, resulting in a set of first strand reads; compiling the set of first strand reads (for example, based on sequence distance or alignment to a reference sequence); constructing a first strand consensus sequence using the set of first strand reads; sequencing a set of amplified second strands formed from a second strand of the duplex nucleic acid molecule, resulting in a set of second strand reads; compiling the set of second strand reads (for example, based on sequence distance or alignment to a reference sequence); constructing a second strand consensus sequence using the set of first strand reads; comparing the first strand consensus sequence and the second strand consensus sequence; identifying and removing errors in the set of first strand reads and the set of second strand reads; and constructing an error-corrected duplex consensus sequence; wherein the duplex nucleic acid molecule is ligated to a sequencing adapter prior to being amplified; and the sequencing adapter is randomly selected from a plurality of sequencing adapters comprising a duplex molecular barcode with a predetermined sequence. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecule is a cell-free DNA molecule, such as a ctDNA molecule or a cfDNA molecule.

In some embodiments, there is provided a method of sequencing a nucleic acid molecule, comprising sequencing a set of amplified first strands formed from a first strand of a duplex nucleic acid molecule, resulting in a set of first strand reads; and constructing a first strand consensus sequence using the set of first strand reads; wherein the duplex nucleic acid molecule is ligated to a sequencing adapter prior to being amplified; and the sequencing adapter is randomly selected from a plurality of sequencing adapters comprising a first sequencing adapter comprising a first duplex molecular barcode n nucleotides in length; and a second sequencing adapter comprising a second duplex molecular barcode n+x nucleotides in length, wherein x is not zero. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecule is a cell-free DNA molecule, such as a ctDNA molecule or a cfDNA molecule.

In some embodiments, there is provided a method of sequencing a nucleic acid molecule, comprising sequencing a set of amplified first strands formed from a first strand of a duplex nucleic acid molecule, resulting in a set of first strand reads; compiling the set of first strand reads (for example, based on sequence distance or alignment to a reference sequence); and constructing a first strand consensus sequence using the set of first strand reads; wherein the duplex nucleic acid molecule is ligated to a sequencing adapter prior to being amplified; and the sequencing adapter is randomly selected from a plurality of sequencing adapters comprising a first sequencing adapter comprising a first duplex molecular barcode n nucleotides in length; and a second sequencing adapter comprising a second duplex molecular barcode n+x nucleotides in length, wherein x is not zero. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecule is a cell-free DNA molecule, such as a ctDNA molecule or a cfDNA molecule.

In some embodiments, there is provided a method of sequencing a nucleic acid molecule, comprising sequencing a set of amplified first strands formed from a first strand of a duplex nucleic acid molecule, resulting in a set of first strand reads; compiling the set of first strand reads (for example, based on sequence distance or alignment to a reference sequence); comparing the first strand reads in the set of first strand reads; identifying and removing errors in the set of first strand reads; and constructing an error-corrected first-strand consensus sequence; wherein the duplex nucleic acid molecule is ligated to a sequencing adapter prior to being amplified; and the sequencing adapter is randomly selected from a plurality of sequencing adapters comprising a first sequencing adapter comprising a first duplex molecular barcode n nucleotides in length; and a second sequencing adapter comprising a second duplex molecular barcode n+x nucleotides in length, wherein x is not zero. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecule is a cell-free DNA molecule, such as a ctDNA molecule or a cfDNA molecule.

In some embodiments, there is provided a method of sequencing a nucleic acid molecule, comprising sequencing a set of amplified first strands formed from a first strand of a duplex nucleic acid molecule, resulting in a set of first strand reads; compiling the set of first strand reads (for example, based on sequence distance or alignment to a reference sequence; constructing a first strand consensus sequence from the set of first strand reads; comparing the first strand consensus sequence to the set of first strand reads; identifying and removing errors in the set of first strand reads; and constructing an error-corrected first strand consensus sequence; wherein the duplex nucleic acid molecule is ligated to a sequencing adapter prior to being amplified; and the sequencing adapter is randomly selected from a plurality of sequencing adapters comprising a first sequencing adapter comprising a first duplex molecular barcode n nucleotides in length; and a second sequencing adapter comprising a second duplex molecular barcode n+x nucleotides in length, wherein x is not zero. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecule is a cell-free DNA molecule, such as a ctDNA molecule or a cfDNA molecule.

In some embodiments, there is provided a method of sequencing a nucleic acid molecule, comprising sequencing a set of amplified first strands formed from a first strand of a duplex nucleic acid molecule, resulting in a set of first strand reads; sequencing a set of amplified second strands formed from a second strand of the duplex nucleic acid molecule, resulting in a set of second strand reads; constructing a first strand consensus sequence using the set of first strand reads; and constructing a second strand consensus sequence using the set of second strand reads; wherein the duplex nucleic acid molecule is ligated to a sequencing adapter prior to being amplified; and the sequencing adapter is randomly selected from a plurality of sequencing adapters comprising a first sequencing adapter comprising a first duplex molecular barcode n nucleotides in length; and a second sequencing adapter comprising a second duplex molecular barcode n+x nucleotides in length, wherein x is not zero. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecule is a cell-free DNA molecule, such as a ctDNA molecule or a cfDNA molecule.

In some embodiments, there is provided a method of sequencing a nucleic acid molecule, comprising sequencing a set of amplified first strands formed from a first strand of a duplex nucleic acid molecule, resulting in a set of first strand reads; compiling the set of first strand reads (for example, based on sequence distance or alignment to a reference sequence); constructing a first strand consensus sequence using the set of first strand reads; sequencing a set of amplified second strands formed from a second strand of the duplex nucleic acid molecule, resulting in a set of second strand reads; compiling the set of second strand reads (for example, based on sequence distance or alignment to a reference sequence); and constructing a second strand consensus sequence using the set of first strand reads; wherein the duplex nucleic acid molecule is ligated to a sequencing adapter prior to being amplified; and the sequencing adapter is randomly selected from a plurality of sequencing adapters comprising a first sequencing adapter comprising a first duplex molecular barcode n nucleotides in length; and a second sequencing adapter comprising a second duplex molecular barcode n+x nucleotides in length, wherein x is not zero. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecule is a cell-free DNA molecule, such as a ctDNA molecule or a cfDNA molecule.

In some embodiments, there is provided a method of sequencing a nucleic acid molecule, comprising sequencing a set of amplified first strands formed from a first strand of a duplex nucleic acid molecule, resulting in a set of first strand reads; compiling the set of first strand reads (for example, based on sequence distance or alignment to a reference sequence); constructing a first strand consensus sequence using the set of first strand reads; sequencing a set of amplified second strands formed from a second strand of the duplex nucleic acid molecule, resulting in a set of second strand reads; compiling the set of second strand reads (for example, based on sequence distance or alignment to a reference sequence); constructing a second strand consensus sequence using the set of first strand reads; comparing the first strand consensus sequence and the second strand consensus sequence; identifying and removing errors in the set of first strand reads and the set of second strand reads; and constructing an error-corrected duplex consensus sequence; wherein the duplex nucleic acid molecule is ligated to a sequencing adapter prior to being amplified; and the sequencing adapter is randomly selected from a plurality of sequencing adapters comprising a first sequencing adapter comprising a first duplex molecular barcode n nucleotides in length; and a second sequencing adapter comprising a second duplex molecular barcode n+x nucleotides in length, wherein x is not zero. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecule is a cell-free DNA molecule, such as a ctDNA molecule or a cfDNA molecule.

In some embodiments, there is provided a method of identifying an error in a nucleic acid sequence, comprising sequencing a first strand of a duplex nucleic acid molecule, resulting in a first strand read; sequencing a second strand of the duplex nucleic acid molecule, resulting in a second strand read; and comparing the first strand read to the second strand read; wherein the duplex nucleic acid molecule is ligated to a sequencing adapter; and the sequencing adapter is randomly selected from a plurality of sequencing adapters comprising a duplex molecular barcode with a predetermined sequence. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecule is a cell-free DNA molecule, such as a ctDNA molecule or a cfDNA molecule.

In some embodiments, there is provided a method of identifying an error in a nucleic acid sequence, comprising sequencing a set of amplified first strands formed from a first strand of a duplex nucleic acid molecule, resulting in a set of first strand reads; sequencing a set of amplified second strands formed from a second strand of the duplex nucleic acid molecule, resulting in a set of second strand reads; constructing a first strand consensus sequence using the set of first strand reads; constructing a second strand consensus sequence using the set of second strand reads; and comparing the first strand consensus sequence to the second strand consensus sequence; wherein the duplex nucleic acid molecule is ligated to a sequencing adapter prior to being amplified; and the sequencing adapter is randomly selected from a plurality of sequencing adapters comprising a duplex molecular barcode with a predetermined sequence. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecule is a cell-free DNA molecule, such as a ctDNA molecule or a cfDNA molecule.

In some embodiments, there is provided a method of identifying an error in a nucleic acid sequence, comprising sequencing a first strand of a duplex nucleic acid molecule, resulting in a first strand read; sequencing a second strand of the duplex nucleic acid molecule, resulting in a second strand read; comparing the first strand read to the second strand read; wherein the duplex nucleic acid molecule is ligated to a sequencing adapter; and the sequencing adapter is randomly selected from a plurality of sequencing adapters comprising a first sequencing adapter comprising a first duplex molecular barcode n nucleotides in length; and a second sequencing adapter comprising a second duplex molecular barcode n+x nucleotides in length, wherein x is not zero. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecule is a cell-free DNA molecule, such as a ctDNA molecule or a cfDNA molecule.

In some embodiments, there is provided a method of identifying an error in a nucleic acid sequence, comprising sequencing a set of amplified first strands formed from a first strand of a duplex nucleic acid molecule, resulting in a set of first strand reads; sequencing a set of amplified second strands formed from a second strand of the duplex nucleic acid molecule, resulting in a set of second strand reads; constructing a first strand consensus sequence using the set of first strand reads; constructing a second strand consensus sequence using the set of second strand reads; and comparing the first strand consensus sequence to the second strand consensus sequence; wherein the duplex nucleic acid molecule is ligated to a sequencing adapter prior to being amplified; and the sequencing adapter is randomly selected from a plurality of sequencing adapters comprising a first sequencing adapter comprising a first duplex molecular barcode n nucleotides in length; and a second sequencing adapter comprising a second duplex molecular barcode n+x nucleotides in length, wherein x is not zero. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecule is a cell-free DNA molecule, such as a ctDNA molecule or a cfDNA molecule.

Methods of Determining the Number of Unique Nucleic Acid Molecules in a Library

In another aspect, there is provided a method of determining the number of unique nucleic acid molecules in a library. Sets of strand reads can be compiled as described above. Because the sets of strand reads are compilations of strand reads from a common parent strand of nucleic acid, the number of sets of strand reads represents the number of unique single-strand nucleic acid molecules in the original nucleic acid library. As a complement set of strand read will be present for each strand read, the number of duplex nucleic acid molecules is represented by the number of sets of strand reads with its complement set of strand reads.

In some embodiments, the sequences for the unique nucleic acid molecules are mapped to a reference genome. By mapping the sequences for the unique nucleic acid molecules to the genome, it is possible to determine how deep a particular portion of the genome is being read.

This method can also be used to determine the number of unique nucleic acid molecules in a library when a plurality of nucleic acid molecule libraries is pooled. Sample indices in the sequence adapters can be used to separate different nucleic acid molecule libraries after the pooled nucleic acid molecule libraries are sequenced. Once the library has been separated based on its sample index, sets of strand reads can be compiled as previously described.

In some embodiments, there is provided a method of determining the number of unique nucleic acid molecules in a nucleic acid library, comprising sequencing a set of amplified first strands formed from a first strand of a duplex nucleic acid molecule, resulting in a set of first strand reads; compiling the set of first strand reads; and counting the number of sets of nucleic acid molecule reads; wherein the duplex nucleic acid molecule is ligated to a sequencing adapter prior to being amplified; and the sequencing adapter is randomly selected from a plurality of sequencing adapters comprising a duplex molecular barcode with a predetermined sequence. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecules comprise cell-free DNA molecules, such as ctDNA molecules or cfDNA molecules.

In some embodiments, there is provided a method of determining the number of unique nucleic acid molecules in a sequencing library, comprising sequencing a set of amplified first strands formed from a first strand of a duplex nucleic acid molecule, resulting in a set of first strand reads; compiling the set of first strand reads; and counting the number of sets of nucleic acid molecule reads; wherein the duplex nucleic acid molecule is ligated to a sequencing adapter prior to being amplified; and the sequencing adapter is randomly selected from a plurality of sequencing adapters comprising a first sequencing adapter comprising a first duplex molecular barcode n nucleotides in length; and a second sequencing adapter comprising a second duplex molecular barcode n+x nucleotides in length, wherein x is not zero. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecules comprise cell-free DNA molecules, such as ctDNA molecules or cfDNA molecules.

In some embodiments, there is provided a method of determining the number of unique nucleic acid molecules in a sequencing library, comprising sequencing a set of amplified first strands formed from a first strand of a duplex nucleic acid molecule, resulting in a set of first strand reads; sequencing a set of amplified second strands formed from a second strand of a duplex nucleic acid molecule, resulting in a set of second strand reads; compiling the set of first strand reads; compiling the set of second strand reads; matching the set of first strand reads to the set of second strand reads; and counting the number of matched sets; wherein the duplex nucleic acid molecule is ligated to a sequencing adapter prior to being amplified; and the sequencing adapter is randomly selected from a plurality of sequencing adapters comprising a duplex molecular barcode with a predetermined sequence. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecules comprise cell-free DNA molecules, such as ctDNA molecules or cfDNA molecules.

In some embodiments, there is provided a method of determining the number of unique nucleic acid molecules in a sequencing library, comprising sequencing a set of amplified first strands formed from a first strand of a duplex nucleic acid molecule, resulting in a set of first strand reads; sequencing a set of amplified second strands formed from a second strand of a duplex nucleic acid molecule, resulting in a set of second strand reads; compiling the set of first strand reads; compiling the set of second strand reads; matching the set of first strand reads to the set of second strand reads; and counting the number of matched sets; wherein the duplex nucleic acid molecule is ligated to a sequencing adapter prior to being amplified; and the sequencing adapter is randomly selected from a plurality of sequencing adapters comprising a first sequencing adapter comprising a first duplex molecular barcode n nucleotides in length; and a second sequencing adapter comprising a second duplex molecular barcode n+x nucleotides in length, wherein x is not zero. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecules comprise cell-free DNA molecules, such as ctDNA molecules or cfDNA molecules.

Balanced Capture Probe Libraries

The nucleic acid library (or nucleic acid sequencing library) or pooled nucleic acid library (or pooled nucleic acid sequencing library) can be enriched for those nucleic acid molecules comprising a portion of one or more regions of interest prior to sequencing using a set of capture probes (also referred to as a capture probe library). The capture probes can hybridize to nucleic acid molecules, and the hybridized duplexes can be separated from nucleic acid molecules that do not hybridize with a capture probe. The capture probes in the set of capture probes are nucleic acid oligonucleotides that can be used to enrich the region of interest. The capture probes are designed to hybridize to nucleic acid molecules containing a portion of the region of interest. The capture probes are therefore substantially complementary to a portion of the region of interest or substantially complementary to a portion adjacent to the region of interest. Some of the nucleic acid molecules in the sequencing library include a portion of the region of interest, and can hybridize to the capture probes. Some of the nucleic acid molecules may also include portions of the genome that are adjacent to the region of interest, which may hybridize to capture probes that are substantially complementary to those portions.

In some embodiments, hybrid capture methods are used to enrich the region of interest by combining capture probes that are substantially complementary to a portion of the region of interest with the nucleic acid library (or nucleic acid sequencing library), thereby hybridizing the capture probes to nucleic acid molecules comprising the portion of the region of interest. The nucleic acid molecules that hybridize to the capture probes can be isolated from non-hybridized nucleic acid molecules (for example, by pull-down methods). The hybridized complex can be denatured and the enriched nucleic acid molecules from the nucleic acid library (or nucleic acid sequencing library) can be sequenced. In some embodiments, the enriched nucleic acid molecules are re-enriched in a second (or more) round of hybridization to the capture probes, isolation and denaturation before being sequenced. Optionally, the nucleic acid molecules in the sequencing library can be amplified (for example, by PCR) either before or after enrichment.

In some embodiments, one or more of the capture probes are attached to an additional oligonucleotide (such as a primer binding site or other specialized nucleic acid segment). In some embodiments, the capture probes in the set of capture probes are DNA oligonucleotides, RNA oligonucleotides, or a mixture of DNA oligonucleotides and RNA oligonucleotides. In some embodiments, the capture probes are about 12 to about 300 bases in length (such as about 12 bases to about 20 bases, 20 bases to about 60 bases in length, about 60 bases to about 100 bases in length, or about 100 bases to about 160 bases, about 160 bases to about 220 bases, or about 220 bases to about 300 bases in length).

In some embodiments two or more capture probes in the set of capture probes are substantially complementary to an overlapping segment of the region of interest. That is, in some embodiments, a given segment of the region of interest can hybridize to two or more capture probes. In some embodiments, the two or more capture probes hybridize to the same strand of the nucleic acid molecule. In some embodiments, the two or more capture probes hybridize to different strands of the nucleic acid molecule. In some embodiments, none of the capture probes in the set of capture probes are substantially complementary to an overlapping segment of the region of interest.

Sequencing depth variation (for example, after sequencing a nucleic acid sequencing library described herein) can be improve by balancing the different capture probes in the set of capture probes. Balanced capture probes are a set of capture probes for a sequence of interest, wherein the amount of each capture probe in the set is predetermined to account for varying efficiency of capture for each probe. Thus, the balanced capture probes provide a reduction in enrichment variance for fragments in the region of interest relative to unbalanced capture probes, which therefore allows for more even sequencing depth across the region of interest. Roak et al., *Multiplex Targeted Sequencing Identifiers Recurrently Mutated Genes in Autism Spectrum Disorders*, Science, vol. 338, pp. 1619-1622 (2012), provides examples of balanced capture probes.

In some embodiments, a balanced set of capture probes is constructed to enrich a nucleic acid library (or nucleic acid sequencing library) to minimize the difference between a predicted sequencing depth profile and a desired sequencing depth profile. The desired sequencing depth profile can be uniform or non-uniform, and the desired sequencing depth profile can be implied by an objective function used to minimize the difference between the predicted and desired sequencing depth profiles. In some embodiments, construction of the balanced set of capture probes is constrained by a minimum amount or a maximum amount of the capture probes in the balanced set of capture probes. The desired sequencing depth profile is made in reference to a reference sequencing library, which is a nucleic acid library used to prepare the balanced set of capture probes. Thus, when a set of capture probes is balanced using a reference sequencing library, the sequencing depth profile obtained after sequencing a test sequencing library may be different from the desired sequencing depth profile due to differences between the reference sequencing library and the test sequencing library.

In some embodiments, preparing a balanced set of capture probes comprises sequencing a reference sequencing library (or a plurality of reference sequencing libraries) comprising a plurality of nucleic acid molecules enriched using a first set of capture probes, wherein each capture probe comprises a sequence that is substantially complementary to a portion of or adjacent to a region of interest included in the reference sequencing library, and wherein an initial known amount of each capture probe is used to form the first set of capture probes; determining a sequencing depth attributable to each capture probe; selecting a subsequent known amount of each capture probe based on the initial known amount and the sequencing depth attributable to said capture probe, wherein the subsequent known amount of each capture probe is selected to minimize a difference between a predicted sequencing depth profile and a desired sequencing depth profile; and constructing the balanced set of capture probes by combining at least a fraction of the capture probes at the subsequent known amount for each capture probe in the balanced set of capture probes. In some embodiments, minimization of the difference is constrained by a minimum subsequent amount or a maximum subsequent amount of each capture probe. In some embodiments, the desired sequencing depth profile is non-uniform.

The reference sequencing library can be enriched by combining the set of capture probes with the reference sequencing library and isolating the nucleic acid molecules in the reference sequencing library that hybridize to any one or more of the capture probes in the set of capture probes. For example, in some embodiments, capture probes are bound by a purification moiety (such as biotin), and the nucleic acid molecules from the reference sequencing library that include a segment of the region of interest can be isolated by hybrid capture methods. Nucleic acid molecules from the reference sequencing library that hybridize to the capture probe can be isolated by pulling down the capture probe bound to the purification moiety, thereby simultaneously pulling down nucleic acid molecules from the reference sequencing library that comprise a segment that is substantially complementary to the capture probe. In some embodiments, the capture probes are biotinylated. Nucleic acid molecules that hybridize to the biotinylated capture probes can be isolated by pulling down the biotinylated capture probes, for example by using a streptavidin conjugated surface (such as streptavidin beads, which can be magnetic).

In some embodiments, the initial known amount of each capture probe is an initial known volume of the capture probe, an initial known mass of the capture probe, or an initial known number of moles of the capture probe. The initial known amount can also be an initial known relative amount (i.e., fraction or percentage) of each capture probe in the set of capture probes. The relative amount can be a relative known volume, mass, or number of moles. The set of capture probes is generally formed by combining the capture probes in a solution. In some embodiments, each capture probe is provided in a stock solution, and the stock solution is combined to form the set of capture probes. The exact concentration of the stock solution is often not known, or the concentration is known within a significant error. However, the concentration of the stock solution need not be known to form the balanced set of capture probes, for example when the same stock solution is used to form the first set of capture probes and any subsequent, balanced set of capture probes. Instead, the relative amount (e.g., volume) of each capture probe can be adjusted to construct the balanced set of capture probes. The subsequent known amount of each capture probe in the balanced capture probe depends, in part, on the initial known amount of each capture probe, and can be determined in the same amount type (i.e., volume, number of moles, grams, concentration, etc.).

Sequencing the enriched reference sequencing library generates a plurality of sequencing reads. In some embodiments, the sequencing reads are aligned to a reference sequence (such as a reference genome or a reference region of interest). In some embodiments, the sequencing depth of a particular locus is based on the number of sequencing reads that align at that locus. In some embodiments, the sequencing reads are aligned to the capture probes. In some embodiments, the sequencing depth is based on the number of sequencing reads that align to the capture probe. In some embodiments, the sequencing depth is adjusted to correct for GC bias. In some embodiments, the sequencing depth is adjusted to correct for mappability. In some embodiments, the sequencing reads are adjusted to account for PCR duplicates that arise from PCR amplification of a sequencing library prior to ligating the nucleic acid molecules to sequencing adapters by eliminating duplicate reads.

In some embodiments, the sequencing depth is a raw number of sequencing reads (which may be adjusted to correct for GC bias, mappability, PCR duplicates, or other sequencing artifacts). In some embodiments, the sequencing depth is based on a number of consensus sequences. A sequencing depth calculated using a consensus sequencing depth is the number of consensus sequences (and thus, the number of represented parent nucleic acid molecules) at any locus. In some embodiments, the sequencing depth is based on a number of duplexed consensus sequences. Duplexed consensus sequences are pairs of consensus sequences which include both strands of the parent nucleic acid molecule.

When preparing the balanced set of balanced capture probes, the sequencing depth attributable to each capture probe is based on the number of sequencing reads that align to at least a portion of the capture probe. In some embodiments, the sequencing reads are consensus sequences formed by collapsing all sequencing reads originating from a parent nucleic acid molecule, which can be identified through a molecular barcode. In some embodiments, the sequencing reads are duplex consensus sequences. In some embodiments, the sequencing reads are error corrected. In some embodiments, the sequencing reads are aligned using a reference sequence, and sequencing reads are attributed to a capture probe that uniquely aligns with at least a portion of the sequencing read. In some embodiments, the sequencing reads are directly aligned with the capture probes, and a sequencing read that uniquely aligns with the capture probe is attributed to that capture probe. The number of sequencing reads comprising a segment that is substantially complementary to at least a portion of the capture probe can then be designated as the sequencing depth attributable to that capture probe. In some embodiments, the sequencing depth is based on a number of sequencing reads that comprises a segment that is substantially complementary to at least 20%, at least 30%, at least 40%, at least 50%, at least 60%, at least 70%, at least 80%, or at least 90% of the capture probe. That is, in some embodiments, sequencing reads that are not substantially complementary for at least 20%, at least 30%, at least 40%, at least 50%, at least 60%, at least 70%, at least 80%, or at least 90% of the capture probe are excluded from the sequencing depth.

Once the sequencing depth attributable to a given capture probe is determined, it is possible to use the sequencing depth to obtain a binding fraction (that is, a determined fraction of the nucleic acid molecules in the reference sequencing library that comprise a segment substantially complementary to a sequence within the capture probe that bound to (i.e., hybridized to) the capture probe during the enrichment of the reference sequencing library) for the capture probe. In some embodiments, the segment substantially complementary to the sequence within the capture probe comprises at least 20%, at least 30%, at least 40%, at least 50%, at least 60%, at least 70%, at least 80%, or at least 90% of the capture probe. Preferably, the number of capture probe molecules is in excess relative to the number of nucleic acid molecules comprising a segment corresponding to at least a portion of the capture probe.

It is assumed that the nucleic acid molecules in the reference sequencing library are in binding equilibrium with the capture probes during the enrichment step. Therefore, a given capture probe ($P_i$) and the set of nucleic acid molecules ($F_i$) comprising a segment substantially complementary to a sequence within the capture probe are in a binding equilibrium with a complex ($P_iF_i$) of both the binding probe and the capture probe.

$$P_i + F_i \rightleftharpoons P_iF_i$$

The binding constant ($K_i$) for each capture probe is defined by:

$$K_i = \frac{[P_iF_i]}{[P_i][F_i]}$$

The total concentration of nucleic acid molecules ($F_i^{total}$) in the reference sequencing library comprising a segment substantially complementary to the sequence within the capture probe (regardless of whether it is bound to the capture probe or not) is determined by.

$$[F_i^{total}] = [F_i] + [P_iF_i]$$

Therefore, the free unbound nucleic acid molecule is:

$$[F_i] = [F_i^{total}] - [P_iF_i]$$

The equation used to determine the total concentration of the nucleic acid molecule ($F_i^{total}$) can be combined with the equation used to determine the binding constant ($K_i$) as follows:

$$[P_iF_i] = K_i[P_i]([F_i^{total}] - [P_iF_i])$$

This equation can be arranged as:

$$[P_iF_i] = [F_i^{total}]\left(1 + \frac{1}{K_i[P_i]}\right)^{-1}$$

Although the product of $K_i$ [$P_i$] cannot be directly observed, the product can be defined as the effective concentration ($c_i$) of the capture probe ($P_i$):

$$c_i = K_i[P_i]$$

The binding fraction for capture probe i can be defined as $\pi_i$ according to:

$$\pi_i = \frac{[P_iF_i]}{[P_iF_i] + [F_i]} = \left(1 + \frac{1}{K_i[P_i]}\right)^{-1}$$

The sequencing depth attributable to a given capture probe (i) in a given reference sequencing library (indexed by s) can be assumed proportional to the concentration of nucleic acid molecules from the sample comprising a segment substantially complementary to a sequence within the capture probe that are bound (i.e., hybridize) to the capture probe during the enrichment step. This can be demonstrated by the following equation:

$$d_{is} \propto [P_iF_i]_s$$

The assumption that the sequencing depth is proportional to the concentration of nucleic acid molecules that bind to the capture probe is justified because non-bound nucleic acid molecules are not retained during the enrichment step (i.e., they are washed away, not amplified, or otherwise not enriched). Thus, only those nucleic acid molecules that bind to the capture probe during the enrichment step are sequenced during downstream steps of the method.

It is also assumed that the total concentration of nucleic acid molecules in the sample [$F_{is}^{total}$] that are substantially complementary to a sequence within each capture probe is constant and does not depend on the particular probe location within the genome. That is, all portions of the region of interest are assumed to be evenly represented by the nucleic acid molecules in the reference sequencing library. Therefore, the total amount of nucleic acid molecules ($N_s$) from the reference sequencing library is proportional to the total concentration of nucleic acid molecules [$F_{is}^{total}$] that comprises a segment substantially complementary to a sequence within each capture probe:

$$N_s \propto [F_{is}^{total}]$$

Using the equations above, the sequencing depth attributed to each capture probe is related to the binding fraction according to the following equation:

$$d_{is} \propto [P_iF_i]_s \propto N_s\pi_i$$

The proportionality constant in this relationship can be absorbed by the amount of nucleic acid molecules in the reference sequencing library ($N_s$). The binding fraction $\pi_i$ is probe dependent, but independent of the number of nucleic acid molecules in the reference sequencing library when the capture probe is in excess. Additionally, the determined sequencing depth will include some amount of noise, and the proportionality equation of the sequencing depth will be satisfied on average, given a large number of samples. That is:

$$\langle d_i \rangle = N_s\pi_i$$

It is therefore preferable that a plurality of sequencing libraries be used to prepare the balanced set of capture probes. Further, the sequencing depth for a given capture probe can be approximated as a Poisson distribution:

$$d_{is} = \text{Poisson}(N_s\pi_i)$$

Once the sequencing depth attributable to each capture probe is determined (the sequencing depth can be based on the number of sequencing reads that comprise a segment substantially complementary to a sequence within the capture probe), a balanced set of capture probes can be constructed by combining the at least a portion of capture probes at a subsequent known amount (that is, subsequent to the amount used in the first set of capture probes). Not all capture probes in the first set of capture probes need to be used in the balanced set of capture probes as long as, if present, each capture probe is present in the subsequent amount (or relative amount). The subsequent known amount is based on the initial known amount and the sequencing depth attributable to each capture probe at that initial known amount. In some embodiments, the method includes obtaining for each capture probe a binding fraction of the nucleic acid molecules comprising a segment that is substantially complementary to a sequence within the capture probe that bound to the capture probe during enrichment of the reference sequencing library based on the sequencing depth attributable to the capture probe. For example, in some embodiments, the binding fraction $\pi_i$ is obtained as described above. In some embodiments, the subsequent known amount of the capture probe in the balanced set of capture probes is based on the initial known amount and the binding fraction.

The sequencing depth attributable to each capture probe can vary as a function of the effective concentration of the capture probe, which depends on the amount of the capture probe included in the set of capture probes. The effective concentration of a given capture probe in the first set of capture probes (which is based on the initial amount of the capture probe in the set of capture probes) can be multiplied by a coefficient $\mu_i$ to obtain a sequencing depth as a function of the coefficient:

$$d_{is}(\mu_i) = N_s \left(1 + \frac{1}{\mu_i c_i}\right)^{-1}$$

The determined sequencing depth attributable to a given capture probe i using the first set of capture probes can be used to determine the initial effective concentration $c_i$, which can be adjusted according to the coefficient $\mu_i$ to achieve the desired level of balance between the plurality of capture probes in the set of capture probe.

The concentration of the capture probe in the balanced set of capture probes $[P_i']$ can be related to the concentration of the capture probe in the first set of capture probes $[P_i]$ through the initial known amount of the capture probe $\gamma_i$ and the subsequent known amount of the capture probe $v_i$. The initial and subsequent known amounts of the capture probe can be a volume, a mass, or a number of moles, or an initial and subsequent known relative amount. The relationship between the concentration of the capture probe in the balanced set of capture probes and the concentration of the capture probe in the first set of capture probes is related according to:

$$[P_i'] = \frac{v_i}{\gamma_i}[P_i]$$

The relationship between the capture probe concentration and the initial and subsequent amounts of the capture probe can be used to relate the binding fraction $\pi_i$ of the nucleic acid molecules in the reference sequencing library comprising a segment substantially complementary to at least a portion of the capture probe that bound to the capture probe according to:

$$\pi_i(v_i) = \left(1 + \frac{\gamma_i}{v_i c_i}\right)^{-1}$$

Sequencing depth attributable to the capture probe in a balanced set of capture probes can then be predicted as a function of the subsequent known amount of the capture probe in the balanced set of capture probes based on the initial known amount of the capture probe in the first set of capture probes and the binding fraction of the nucleic acid molecules comprising a segment substantially complementary to at least a portion of the capture probe that bound to the capture probe during the enrichment of the reference sequencing library (which can be obtained from the sequencing depth attributable to the capture probe in the first set of capture probes) according to:

$$d_{is}(v_i) = N_s \pi_i(v_i) = N_s \left(1 + \frac{\gamma_i}{v_i c_i}\right)^{-1}$$

The subsequent amount $v_i$ for each capture probe in the balanced set of capture probes can be selected to minimize the difference between a predicted sequencing depth profile and a desired sequencing depth profile, which is optionally non-uniform. A uniform desired sequencing depth profile would require the sequencing depth attributable to each capture probe in the balanced set of capture probes to be the same. Thus, a non-uniform desired sequencing depth profile requires the sequencing depth attributable to at least one capture probe in the balanced set of capture probes to be different from the sequencing depth attributable to at least one other capture probe in the set of capture probes. For example, the difference may be a two-fold or more, three-fold or more, four-fold or more, or five-fold or more increase or decrease in sequencing depth. In some embodiments, the desired sequencing depth profile is uniform.

The difference between the predicted sequencing depth profile and the desired sequencing depth profile can be minimized based on any objective function, such as a coefficient of variation (i.e., the ratio of a measure of variation (such as a standard deviation) to an average (such as a mean)), using the predicted sequencing depth $d_{is}(v_i)$ or binding fraction $\pi_i$. The difference between the predicted sequencing depth profile and the desired sequencing depth profile can also be minimized based on an objective function using the effective concentration ($c_i$), for example by defining the objective function as an implicit function of the effective concentration.

Since the number of nucleic acid molecules in the reference sequencing library is independent of the capture probe, minimizing the difference between the predicted sequencing depth profile and the desired depth profile can be accomplished by minimizing the variability of the binding fraction $\pi_i$ between the capture probes in the set of capture probes. Therefore, $N_s$ can be ignored when minimizing the variability. The difference can be defined by an objective function of the subsequent amounts of the capture probes in the balanced set of capture probes, according to:

$$f(\vec{v}) = V(\vec{\pi}(\vec{v}))$$

wherein:

$$(\vec{\pi}(\vec{v}))_i = \left(1 + \frac{\gamma_i}{v_i c_i}\right)^{-1}$$

and wherein V( ) is a user-defined objective function (such as the coefficient of variation) for the set of capture probes; $(\vec{\pi}(\vec{v}))_i$ is the binding fraction of the nucleic acid molecules comprising a segment substantially complementary to at least a portion of the capture probe i that bound to the capture probe i during enrichment of the reference sequencing library for the vector $\vec{\pi}(\vec{v})$, $c_i$ is an effective concentration for capture probe i for the vector $\vec{\pi}(\vec{v})$, $v_i$ is the subsequent amount of capture probe i for the vector $\vec{\pi}(\vec{v})$; and $\gamma_i$ is the initial amount of capture probe i for the vector $\vec{\pi}(\vec{v})$.

Alternatively, minimizing the difference between the predicted sequencing depth profile and the desired sequencing depth profile can comprise minimizing an objective function for the effective concentration $c_i$ instead of $\pi_i$.

The binding fraction $\pi_i$ can be obtained based on the determined sequencing depth attributable to the capture probe by fitting a model, such as a maximum likelihood model or a Markov chain Monte Carlo model. For example, a maximum log-likelihood (LL) model can be fit for a capture probe i in the reference sequencing library s according to:

$$LL = \sum_{is} d_{is} \log(N_s \pi_i) - N_s \pi_i$$

The desired sequencing depth can be implied by the objective function. For example, the objective function can assume the desired sequencing depth to be uniform by applying uniform objective function terms to all capture probes. For example, by minimizing the coefficient of variation of sequencing depth across all capture probes without further adjustment, the desired sequencing profile is implied to be uniform. The desired sequencing depth profile therefore need not be explicitly defined. In some embodiments, the non-uniform sequencing depth profile comprises a first sequencing depth (or relative sequencing depth) attributable to a first capture probe in the set of capture probes and a second sequencing depth (or relative sequencing depth) attributable to a second capture probe in the set of capture probes. The objective function can be a summed statistical difference (such as a sum of squares of the difference) between the predicted sequencing depth and the desired sequencing depth attributable to the capture probes, wherein the desired sequencing depth is defined to be non-uniform. Minimization of the objective function can then provide the subsequent amounts of the capture probes in the set of capture probes.

In some embodiments, minimization of the difference between the predicted sequencing depth profile and the desired sequencing depth profile is constrained by a minimum subsequent amount or a maximum subsequent amount (or both a minimum and a maximum subsequent amount) of each capture probe. This may be done to avoid making very large changes in the amount of each probe in the set of capture probes between the first set of capture probes and the balanced set of capture probes. Further, dispensing very small amounts of the capture probe are subject to precision limits. For example, pipetting nanoliter volumes is impractical without some amount of error. Additionally, there may be finite amounts of the capture probe available, thereby limiting the amount of capture probe that can be used to form the set of capture probes. A very large amount of a single probe could also result in undesirable dilution of the other capture probes in the set of capture probes. By constraining the minimum and/or maximum amounts of each capture probe used to form the library during the minimization determination, dramatic changes can be minimized (which can minimize unaccounted for interactions) and practical amounts of each capture probe can be combined to form the set of capture probes. This optimization can be written as:

$$\underset{\vec{v}}{\text{minimize}} f(\vec{v})$$

$$\text{subject to } m \leq v_i \leq M$$

wherein m is the minimum subsequent amount of the capture probe and M is the maximum subsequent amount of the capture probe. In some embodiments, the minimum subsequent amount is about 10 nanoliters (nL) or more (such as about 20 nL or more, about 30 nL or more, about 40 nL or more, about 50 nL or more, about 75 nL or more, or about 100 nL or more). In some embodiments, the maximum subsequent amount is about 1 mL or less (such as about 750 µL or less, about 500 µL or less, about 400 µL or less, about 300 µL or less, about 200 µL or less, about 100 µL or less, about 75 µL or less, about 50 µL or less, about 25 µL or less, or about 10 µL or less).

Once the subsequent amounts of each capture probe are determined, the second (i.e., "balanced") set of capture probes can be constructed by combining the capture probes (or at least a fraction of the capture probes) at the subsequent known amount (such as volume, mass, or number of moles, as for the initial known amount). In some embodiments, the capture probes are mixed in solution (such as an aqueous buffer). The capture probes can be combined, for example, by a liquid handler or a pipetting system (which may be manual or automatic). In some embodiments, the liquid handler or the pipetting system can handle volumes in a wide range, for example about 50 nL to about 1 mL (or about 100 nL to about 500 µL).

Balancing the set of capture probes can optionally be performed iteratively. That is, the second (balanced) set of capture probes can be re-balanced one or more times, two or more times, three or more times, four or more times, or five or more times. Preferably, the same reference sequencing library used to initially balance the set of capture probes is used to rebalance the balanced set of capture probes. In some embodiments, the method further comprises enriching the reference sequencing library using the balanced set of capture probes; sequencing the reference sequencing library enriched using the balanced set of capture probes; determining a sequencing depth attributable to each capture probe in the balanced set of capture probes; selecting a second subsequent known amount of each capture probe based on the subsequent known amount of said capture probe in the second set of capture probes and the sequencing depth attributable to said capture probe, wherein the second subsequent known amount of each capture probe is selected to minimize a difference between a second predicted sequencing depth profile and the desired sequencing depth profile; and constructing a re-balanced set of capture probes by combining at least a fraction of the capture probes at the second subsequent known amount of each capture probe in the re-balanced set of capture probes. In some embodiments, minimization of the difference is constrained by a minimum second subsequent amount or a maximum second subsequent amount of each capture probe. The minimum subsequent amount or the maximum subsequent amount may be the same as or different from the minimum subsequent amount or the maximum subsequent amount used in the first or any late re-balancing iteration.

Two or more balanced (including rebalanced) capture probe libraries can be combined to form a pooled set of capture probes. In some embodiments, the region of interest for each balanced set of capture probes is distinct.

The balanced set of capture probes can be used in the methods described herein, such as in a method of sequencing a nucleic acid molecule, a method of identifying an error in a nucleic acid sequence, or a method of determining a number of unique nucleic acid molecules in a library.

In some embodiments, there is provided a method of sequencing a nucleic acid molecule, comprising sequencing a set of amplified first strands formed from a first strand of a duplex nucleic acid molecule, resulting in a set of first-strand reads; compiling the set of first strand reads (for example, based on sequence distance or alignment to a reference sequence); and constructing a first strand consensus sequence using the set of first strand reads; wherein the duplex nucleic acid molecule is ligated to a sequencing adapter prior to being amplified; and the sequencing adapter is randomly selected from a plurality of sequencing adapters comprising a duplex molecular barcode with a predetermined sequence; and wherein the duplex nucleic acid molecule is enriched using a set of capture probes for a region of interest, wherein the set of capture probes is prepared by sequencing a reference sequencing library comprising a plurality of nucleic acid molecules enriched using a first set of capture probes, wherein each capture probe comprises a sequence that is substantially complementary to a portion of or adjacent to a region of interest included in the reference sequencing library, and wherein an initial known amount of each capture probe is used to form the first set of capture probes; determining a sequencing depth attributable to each capture probe; selecting a subsequent known amount of each capture probe based on the initial known amount and the sequencing depth attributable to said capture probe, wherein the subsequent known amount of each capture probe is selected to minimize a difference between a predicted sequencing depth profile and a desired sequencing depth profile; and constructing the balanced set of capture probes by combining at least a fraction of the capture probes at the subsequent known amount of each capture probe in the balanced set of capture probes. In some embodiments, minimization of the difference is constrained by a minimum subsequent amount or a maximum subsequent amount of each capture probe. In some embodiments, the desired sequencing depth profile is uniform. In some embodiments, the desired sequencing depth profile is non-uniform. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecule is a cell-free DNA molecule, such as a ctDNA molecule or a cfDNA molecule.

In some embodiments, there is provided a method of sequencing a nucleic acid molecule, comprising sequencing a set of amplified first strands formed from a first strand of a duplex nucleic acid molecule, resulting in a set of first strand reads; compiling the set of first strand reads (for example, based on sequence distance or alignment to a reference sequence); comparing the first strand reads in the set of first strand reads; identifying and removing errors in the set of first strand reads; and constructing an error-corrected first-strand consensus sequence; wherein the duplex nucleic acid molecule is ligated to a sequencing adapter prior to being amplified; and the sequencing adapter is randomly selected from a plurality of sequencing adapters comprising a duplex molecular barcode with a predetermined sequence; and wherein the duplex nucleic acid molecule is enriched using a set of capture probes for a region of interest, wherein the set of capture probes is prepared by sequencing a reference sequencing library comprising a plurality of nucleic acid molecules enriched using a first set of capture probes, wherein each capture probe comprises a sequence that is substantially complementary to a portion of or adjacent to a region of interest included in the reference sequencing library, and wherein an initial known amount of each capture probe is used to form the first set of capture probes; determining a sequencing depth attributable to each capture probe; selecting a subsequent known amount of each capture probe based on the initial known amount and the sequencing depth attributable to said capture probe, wherein the subsequent known amount of each capture probe is selected to minimize a difference between a predicted sequencing depth profile and a desired sequencing depth profile; and constructing the balanced set of capture probes by combining at least a fraction of the capture probes at the subsequent known amount of each capture probe in the balanced set of capture probes. In some embodiments, minimization of the difference is constrained by a minimum subsequent amount or a maximum subsequent amount of each capture probe. In some embodiments, the desired sequencing depth profile is uniform. In some embodiments, the desired sequencing depth profile is non-uniform. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecule is a cell-free DNA molecule, such as a ctDNA molecule or a cfDNA molecule.

In some embodiments, there is provided a method of sequencing a nucleic acid molecule, comprising sequencing a set of amplified first strands formed from a first strand of a duplex nucleic acid molecule, resulting in a set of first strand reads; compiling the set of first strand reads (for example, based on sequence distance or alignment to a reference sequence); constructing a first strand consensus sequence from the set of first strand reads; comparing the first strand consensus sequence to the set of first strand reads; identifying and removing errors in the set of first strand reads; and constructing an error-corrected first strand consensus sequence; wherein the duplex nucleic acid molecule is ligated to a sequencing adapter prior to being amplified; and the sequencing adapter is randomly selected from a plurality of sequencing adapters comprising a duplex molecular barcode with a predetermined sequence; and wherein the duplex nucleic acid molecule is enriched using a set of capture probes for a region of interest, wherein the set of capture probes is prepared by sequencing a reference sequencing library comprising a plurality of nucleic acid molecules enriched using a first set of capture probes, wherein each capture probe comprises a sequence that is substantially complementary to a portion of or adjacent to a region of interest included in the reference sequencing library, and wherein an initial known amount of each capture probe is used to form the first set of capture probes; determining a sequencing depth attributable to each capture probe; selecting a subsequent known amount of each capture probe based on the initial known amount and the sequencing depth attributable to said capture probe, wherein the subsequent known amount of each capture probe is selected to minimize a difference between a predicted sequencing depth profile and a desired sequencing depth profile; and constructing the balanced set of capture probes by combining at least a fraction of the capture probes at the subsequent known amount of each capture probe in the balanced set of capture probes. In some embodiments, minimization of the difference is constrained by a minimum subsequent amount or a maximum subsequent amount of each capture probe. In some embodiments, the desired sequencing depth profile is uniform. In some embodiments, the desired sequencing depth profile is non-uniform. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecule is a cell-free DNA molecule, such as a ctDNA molecule or a cfDNA molecule.

In some embodiments, there is provided a method of sequencing a nucleic acid molecule, comprising sequencing a set of amplified first strands formed from a first strand of a duplex nucleic acid molecule, resulting in a set of first strand reads; sequencing a set of amplified second strands formed from a second strand of the duplex nucleic acid molecule, resulting in a set of second strand reads; constructing a first strand consensus sequence using the set of first strand reads; and constructing a second strand consensus sequence using the set of second strand reads; wherein the duplex nucleic acid molecule is ligated to a sequencing adapter prior to being amplified; and the sequencing adapter is randomly selected from a plurality of sequencing adapters comprising a duplex molecular barcode with a predetermined sequence; and wherein the duplex nucleic acid molecule is enriched using a set of capture probes for a region of interest, wherein the set of capture probes is prepared by sequencing a reference sequencing library comprising a plurality of nucleic acid molecules enriched using a first set of capture probes, wherein each capture probe comprises a sequence that is substantially complementary to a portion of or adjacent to a region of interest included in the reference sequencing library, and wherein an initial known amount of each capture probe is used to form the first set of capture probes; determining a sequencing depth attributable to each capture probe; selecting a subsequent known amount of each capture probe based on the initial known amount and the sequencing depth attributable to said capture probe, wherein the subsequent known amount of each capture probe is selected to minimize a difference between a predicted sequencing depth profile and a desired sequencing depth profile; and constructing the balanced set of capture probes by combining at least a fraction of the capture probes at the subsequent known amount of each capture probe in the balanced set of capture probes. In some embodiments, minimization of the difference is constrained by a minimum subsequent amount or a maximum subsequent amount of each capture probe. In some embodiments, the desired sequencing depth profile is uniform. In some embodiments, the desired sequencing depth profile is non-uniform. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecule is a cell-free DNA molecule, such as a ctDNA molecule or a cfDNA molecule.

In some embodiments, there is provided a method of sequencing a nucleic acid molecule, comprising sequencing a set of amplified first strands formed from a first strand of a duplex nucleic acid molecule, resulting in a set of first strand reads; compiling the set of first strand reads (for example, based on sequence distance or alignment to a reference sequence); constructing a first strand consensus sequence using the set of first strand reads; sequencing a set of amplified second strands formed from a second strand of the duplex nucleic acid molecule, resulting in a set of second strand reads; compiling the set of second strand reads (for example, based on sequence distance or alignment to a reference sequence); and constructing a second strand consensus sequence using the set of first strand reads; wherein the duplex nucleic acid molecule is ligated to a sequencing adapter prior to being amplified; and the sequencing adapter is randomly selected from a plurality of sequencing adapters comprising a duplex molecular barcode with a predetermined sequence; and wherein the duplex nucleic acid molecule is enriched using a set of capture probes for a region of interest, wherein the set of capture probes is prepared by sequencing a reference sequencing library comprising a plurality of nucleic acid molecules enriched using a first set of capture probes, wherein each capture probe comprises a sequence that is substantially complementary to a portion of or adjacent to a region of interest included in the reference sequencing library, and wherein an initial known amount of each capture probe is used to form the first set of capture probes; determining a sequencing depth attributable to each capture probe; selecting a subsequent known amount of each capture probe based on the initial known amount and the sequencing depth attributable to said capture probe, wherein the subsequent known amount of each capture probe is selected to minimize a difference between a predicted sequencing depth profile and a desired sequencing depth profile; and constructing the balanced set of capture probes by combining at least a fraction of the capture probes at the subsequent known amount of each capture probe in the balanced set of capture probes. In some embodiments, minimization of the difference is constrained by a minimum subsequent amount or a maximum subsequent amount of each capture probe. In some embodiments, the desired sequencing depth profile is uniform. In some embodiments, the desired sequencing depth profile is non-uniform. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecule is a cell-free DNA molecule, such as a ctDNA molecule or a cfDNA molecule.

In some embodiments, there is provided a method of sequencing a nucleic acid molecule, comprising sequencing a set of amplified first strands formed from a first strand of a duplex nucleic acid molecule, resulting in a set of first strand reads; compiling the set of first strand reads (for example, based on sequence distance or alignment to a reference sequence); constructing a first strand consensus sequence using the set of first strand reads; sequencing a set of amplified second strands formed from a second strand of the duplex nucleic acid molecule, resulting in a set of second strand reads; compiling the set of second strand reads (for example, based on sequence distance or alignment to a reference sequence); constructing a second strand consensus sequence using the set of first strand reads; comparing the first strand consensus sequence and the second strand consensus sequence; identifying and removing errors in the set of first strand reads and the set of second strand reads; and constructing an error-corrected duplex consensus sequence; wherein the duplex nucleic acid molecule is ligated to a sequencing adapter prior to being amplified; and the sequencing adapter is randomly selected from a plurality of sequencing adapters comprising a duplex molecular barcode with a predetermined sequence; and wherein the duplex nucleic acid molecule is enriched using a set of capture probes for a region of interest, wherein the set of capture probes is prepared by sequencing a reference sequencing library comprising a plurality of nucleic acid molecules enriched using a first set of capture probes, wherein each capture probe comprises a sequence that is substantially complementary to a portion of or adjacent to a region of interest included in the reference sequencing library, and wherein an initial known amount of each capture probe is used to form the first set of capture probes; determining a sequencing depth attributable to each capture probe; selecting a subsequent known amount of each capture probe based on the initial known amount and the sequencing depth attributable to said capture probe, wherein the subsequent known amount of each capture probe is selected to minimize a difference between a predicted sequencing depth profile and a desired sequencing depth profile; and constructing the balanced set of capture probes by combining at least a fraction of the capture probes at the subsequent known amount of each capture probe in the balanced set of capture probes. In some embodiments, minimization of the difference is constrained by a minimum subsequent amount or a maximum subsequent amount of each capture probe. In some embodiments, the desired sequencing depth profile is uniform. In some embodiments, the desired sequencing depth profile is non-uniform. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecule is a cell-free DNA molecule, such as a ctDNA molecule or a cfDNA molecule.

In some embodiments, there is provided a method of sequencing a nucleic acid molecule, comprising sequencing a set of amplified first strands formed from a first strand of a duplex nucleic acid molecule, resulting in a set of first strand reads; and constructing a first strand consensus sequence using the set of first strand reads; wherein the duplex nucleic acid molecule is ligated to a sequencing adapter prior to being amplified; and the sequencing adapter is randomly selected from a plurality of sequencing adapters comprising a first sequencing adapter comprising a first duplex molecular barcode n nucleotides in length; and a second sequencing adapter comprising a second duplex molecular barcode n+x nucleotides in length, wherein x is not zero; and wherein the duplex nucleic acid molecule is enriched using a set of capture probes for a region of interest, wherein the set of capture probes is prepared by sequencing a reference sequencing library comprising a plurality of nucleic acid molecules enriched using a first set of capture probes, wherein each capture probe comprises a sequence that is substantially complementary to a portion of or adjacent to a region of interest included in the reference sequencing library, and wherein an initial known amount of each capture probe is used to form the first set of capture probes; determining a sequencing depth attributable to each capture probe; selecting a subsequent known amount of each capture probe based on the initial known amount and the sequencing depth attributable to said capture probe, wherein the subsequent known amount of each capture probe is selected to minimize a difference between a predicted sequencing depth profile and a desired sequencing depth profile; and constructing the balanced set of capture probes by combining at least a fraction of the capture probes at the subsequent known amount of each capture probe in the balanced set of capture probes. In some embodiments, minimization of the difference is constrained by a minimum subsequent amount or a maximum subsequent amount of each capture probe. In some embodiments, the desired sequencing depth profile is uniform. In some embodiments, the desired sequencing depth profile is non-uniform. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecule is a cell-free DNA molecule, such as a ctDNA molecule or a cfDNA molecule.

In some embodiments, there is provided a method of sequencing a nucleic acid molecule, comprising sequencing a set of amplified first strands formed from a first strand of a duplex nucleic acid molecule, resulting in a set of first strand reads; compiling the set of first strand reads (for example, based on sequence distance or alignment to a reference sequence); and constructing a first strand consensus sequence using the set of first strand reads; wherein the duplex nucleic acid molecule is ligated to a sequencing adapter prior to being amplified; and the sequencing adapter is randomly selected from a plurality of sequencing adapters comprising a first sequencing adapter comprising a first duplex molecular barcode n nucleotides in length; and a second sequencing adapter comprising a second duplex molecular barcode n+x nucleotides in length, wherein x is not zero; and wherein the duplex nucleic acid molecule is enriched using a set of capture probes for a region of interest, wherein the set of capture probes is prepared by sequencing a reference sequencing library comprising a plurality of nucleic acid molecules enriched using a first set of capture probes, wherein each capture probe comprises a sequence that is substantially complementary to a portion of or adjacent to a region of interest included in the reference sequencing library, and wherein an initial known amount of each capture probe is used to form the first set of capture probes; determining a sequencing depth attributable to each capture probe; selecting a subsequent known amount of each capture probe based on the initial known amount and the sequencing depth attributable to said capture probe, wherein the subsequent known amount of each capture probe is selected to minimize a difference between a predicted sequencing depth profile and a desired sequencing depth profile; and constructing the balanced set of capture probes by combining at least a fraction of the capture probes at the subsequent known amount of each capture probe in the balanced set of capture probes. In some embodiments, minimization of the difference is constrained by a minimum subsequent amount or a maximum subsequent amount of each capture probe. In some embodiments, the desired sequencing depth profile is uniform. In some embodiments, the desired sequencing depth profile is non-uniform. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecule is a cell-free DNA molecule, such as a ctDNA molecule or a cfDNA molecule.

In some embodiments, there is provided a method of sequencing a nucleic acid molecule, comprising sequencing a set of amplified first strands formed from a first strand of a duplex nucleic acid molecule, resulting in a set of first strand reads; compiling the set of first strand reads (for example, based on sequence distance or alignment to a reference sequence); comparing the first strand reads in the set of first strand reads; identifying and removing errors in the set of first strand reads; and constructing an error-corrected first-strand consensus sequence; wherein the duplex nucleic acid molecule is ligated to a sequencing adapter prior to being amplified; and the sequencing adapter is randomly selected from a plurality of sequencing adapters comprising a first sequencing adapter comprising a first duplex molecular barcode n nucleotides in length; and a second sequencing adapter comprising a second duplex molecular barcode n+x nucleotides in length, wherein x is not zero; and wherein the duplex nucleic acid molecule is enriched using a set of capture probes for a region of interest, wherein the set of capture probes is prepared by sequencing a reference sequencing library comprising a plurality of nucleic acid molecules enriched using a first set of capture probes, wherein each capture probe comprises a sequence that is substantially complementary to a portion of or adjacent to a region of interest included in the reference sequencing library, and wherein an initial known amount of each capture probe is used to form the first set of capture probes; determining a sequencing depth attributable to each capture probe; selecting a subsequent known amount of each capture probe based on the initial known amount and the sequencing depth attributable to said capture probe, wherein the subsequent known amount of each capture probe is selected to minimize a difference between a predicted sequencing depth profile and a desired sequencing depth profile; and constructing the balanced set of capture probes by combining at least a fraction of the capture probes at the subsequent known amount of each capture probe in the balanced set of capture probes. In some embodiments, minimization of the difference is constrained by a minimum subsequent amount or a maximum subsequent amount of each capture probe. In some embodiments, the desired sequencing depth profile is uniform. In some embodiments, the desired sequencing depth profile is non-uniform. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecule is a cell-free DNA molecule, such as a ctDNA molecule or a cfDNA molecule.

In some embodiments, there is provided a method of sequencing a nucleic acid molecule, comprising sequencing a set of amplified first strands formed from a first strand of a duplex nucleic acid molecule, resulting in a set of first strand reads; compiling the set of first strand reads (for example, based on sequence distance or alignment to a reference sequence); constructing a first strand consensus sequence from the set of first strand reads; comparing the first strand consensus sequence to the set of first strand reads; identifying and removing errors in the set of first strand reads; and constructing an error-corrected first strand consensus sequence; wherein the duplex nucleic acid molecule is ligated to a sequencing adapter prior to being amplified; and the sequencing adapter is randomly selected from a plurality of sequencing adapters comprising a first sequencing adapter comprising a first duplex molecular barcode n nucleotides in length; and a second sequencing adapter comprising a second duplex molecular barcode n+x nucleotides in length, wherein x is not zero; and wherein the duplex nucleic acid molecule is enriched using a set of capture probes for a region of interest, wherein the set of capture probes is prepared by sequencing a reference sequencing library comprising a plurality of nucleic acid molecules enriched using a first set of capture probes, wherein each capture probe comprises a sequence that is substantially complementary to a portion of or adjacent to a region of interest included in the reference sequencing library, and wherein an initial known amount of each capture probe is used to form the first set of capture probes; determining a sequencing depth attributable to each capture probe; selecting a subsequent known amount of each capture probe based on the initial known amount and the sequencing depth attributable to said capture probe, wherein the subsequent known amount of each capture probe is selected to minimize a difference between a predicted sequencing depth profile and a desired sequencing depth profile; and constructing the balanced set of capture probes by combining at least a fraction of the capture probes at the subsequent known amount of each capture probe in the balanced set of capture probes. In some embodiments, minimization of the difference is constrained by a minimum subsequent amount or a maximum subsequent amount of each capture probe. In some embodiments, the desired sequencing depth profile is uniform. In some embodiments, the desired sequencing depth profile is non-uniform. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecule is a cell-free DNA molecule, such as a ctDNA molecule or a cfDNA molecule.

In some embodiments, there is provided a method of sequencing a nucleic acid molecule, comprising sequencing a set of amplified first strands formed from a first strand of a duplex nucleic acid molecule, resulting in a set of first strand reads; sequencing a set of amplified second strands formed from a second strand of the duplex nucleic acid molecule, resulting in a set of second strand reads; constructing a first strand consensus sequence using the set of first strand reads; and constructing a second strand consensus sequence using the set of second strand reads; wherein the duplex nucleic acid molecule is ligated to a sequencing adapter prior to being amplified; and the sequencing adapter is randomly selected from a plurality of sequencing adapters comprising a first sequencing adapter comprising a first duplex molecular barcode n nucleotides in length; and a second sequencing adapter comprising a second duplex molecular barcode n+x nucleotides in length, wherein x is not zero; and wherein the duplex nucleic acid molecule is enriched using a set of capture probes for a region of interest, wherein the set of capture probes is prepared by sequencing a reference sequencing library comprising a plurality of nucleic acid molecules enriched using a first set of capture probes, wherein each capture probe comprises a sequence that is substantially complementary to a portion of or adjacent to a region of interest included in the reference sequencing library, and wherein an initial known amount of each capture probe is used to form the first set of capture probes; determining a sequencing depth attributable to each capture probe; selecting a subsequent known amount of each capture probe based on the initial known amount and the sequencing depth attributable to said capture probe, wherein the subsequent known amount of each capture probe is selected to minimize a difference between a predicted sequencing depth profile and a desired sequencing depth profile; and constructing the balanced set of capture probes by combining at least a fraction of the capture probes at the subsequent known amount of each capture probe in the balanced set of capture probes. In some embodiments, minimization of the difference is constrained by a minimum subsequent amount or a maximum subsequent amount of each capture probe. In some embodiments, the desired sequencing depth profile is uniform. In some embodiments, the desired sequencing depth profile is non-uniform. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecule is a cell-free DNA molecule, such as a ctDNA molecule or a cfDNA molecule.

In some embodiments, there is provided a method of sequencing a nucleic acid molecule, comprising sequencing a set of amplified first strands formed from a first strand of a duplex nucleic acid molecule, resulting in a set of first strand reads; compiling the set of first strand reads (for example, based on sequence distance or alignment to a reference sequence); constructing a first strand consensus sequence using the set of first strand reads; sequencing a set of amplified second strands formed from a second strand of the duplex nucleic acid molecule, resulting in a set of second strand reads; compiling the set of second strand reads (for example, based on sequence distance or alignment to a reference sequence); and constructing a second strand consensus sequence using the set of first strand reads; wherein the duplex nucleic acid molecule is ligated to a sequencing adapter prior to being amplified; and the sequencing adapter is randomly selected from a plurality of sequencing adapters comprising a first sequencing adapter comprising a first duplex molecular barcode n nucleotides in length; and a second sequencing adapter comprising a second duplex molecular barcode n+x nucleotides in length, wherein x is not zero; and wherein the duplex nucleic acid molecule is enriched using a set of capture probes for a region of interest, wherein the set of capture probes is prepared by sequencing a reference sequencing library comprising a plurality of nucleic acid molecules enriched using a first set of capture probes, wherein each capture probe comprises a sequence that is substantially complementary to a portion of or adjacent to a region of interest included in the reference sequencing library, and wherein an initial known amount of each capture probe is used to form the first set of capture probes; determining a sequencing depth attributable to each capture probe; selecting a subsequent known amount of each capture probe based on the initial known amount and the sequencing depth attributable to said capture probe, wherein the subsequent known amount of each capture probe is selected to minimize a difference between a predicted sequencing depth profile and a desired sequencing depth profile; and constructing the balanced set of capture probes by combining at least a fraction of the capture probes at the subsequent known amount of each capture probe in the balanced set of capture probes. In some embodiments, minimization of the difference is constrained by a minimum subsequent amount or a maximum subsequent amount of each capture probe. In some embodiments, the desired sequencing depth profile is uniform. In some embodiments, the desired sequencing depth profile is non-uniform. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecule is a cell-free DNA molecule, such as a ctDNA molecule or a cfDNA molecule.

In some embodiments, there is provided a method of sequencing a nucleic acid molecule, comprising sequencing a set of amplified first strands formed from a first strand of a duplex nucleic acid molecule, resulting in a set of first strand reads; compiling the set of first strand reads (for example, based on sequence distance or alignment to a reference sequence); constructing a first strand consensus sequence using the set of first strand reads; sequencing a set of amplified second strands formed from a second strand of the duplex nucleic acid molecule, resulting in a set of second strand reads; compiling the set of second strand reads (for example, based on sequence distance or alignment to a reference sequence); constructing a second strand consensus sequence using the set of first strand reads; comparing the first strand consensus sequence and the second strand consensus sequence; identifying and removing errors in the set of first strand reads and the set of second strand reads; and constructing an error-corrected duplex consensus sequence; wherein the duplex nucleic acid molecule is ligated to a sequencing adapter prior to being amplified; and the sequencing adapter is randomly selected from a plurality of sequencing adapters comprising a first sequencing adapter comprising a first duplex molecular barcode n nucleotides in length; and a second sequencing adapter comprising a second duplex molecular barcode n+x nucleotides in length, wherein x is not zero; and wherein the duplex nucleic acid molecule is enriched using a set of capture probes for a region of interest, wherein the set of capture probes is prepared by sequencing a reference sequencing library comprising a plurality of nucleic acid molecules enriched using a first set of capture probes, wherein each capture probe comprises a sequence that is substantially complementary to a portion of or adjacent to a region of interest included in the reference sequencing library, and wherein an initial known amount of each capture probe is used to form the first set of capture probes; determining a sequencing depth attributable to each capture probe; selecting a subsequent known amount of each capture probe based on the initial known amount and the sequencing depth attributable to said capture probe, wherein the subsequent known amount of each capture probe is selected to minimize a difference between a predicted sequencing depth profile and a desired sequencing depth profile; and constructing the balanced set of capture probes by combining at least a fraction of the capture probes at the subsequent known amount of each capture probe in the balanced set of capture probes. In some embodiments, minimization of the difference is constrained by a minimum subsequent amount or a maximum subsequent amount of each capture probe. In some embodiments, the desired sequencing depth profile is uniform. In some embodiments, the desired sequencing depth profile is non-uniform. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecule is a cell-free DNA molecule, such as a ctDNA molecule or a cfDNA molecule.

In some embodiments, there is provided a method of identifying an error in a nucleic acid sequence, comprising sequencing a first strand of a duplex nucleic acid molecule, resulting in a first strand read; sequencing a second strand of the duplex nucleic acid molecule, resulting in a second strand read; and comparing the first strand read to the second strand read; wherein the duplex nucleic acid molecule is ligated to a sequencing adapter; and the sequencing adapter is randomly selected from a plurality of sequencing adapters comprising a duplex molecular barcode with a predetermined sequence; and wherein the duplex nucleic acid molecule is enriched using a set of capture probes for a region of interest, wherein the set of capture probes is prepared by sequencing a reference sequencing library comprising a plurality of nucleic acid molecules enriched using a first set of capture probes, wherein each capture probe comprises a sequence that is substantially complementary to a portion of or adjacent to a region of interest included in the reference sequencing library, and wherein an initial known amount of each capture probe is used to form the first set of capture probes; determining a sequencing depth attributable to each capture probe; selecting a subsequent known amount of each capture probe based on the initial known amount and the sequencing depth attributable to said capture probe, wherein the subsequent known amount of each capture probe is selected to minimize a difference between a predicted sequencing depth profile and a desired sequencing depth profile; and constructing the balanced set of capture probes by combining at least a fraction of the capture probes at the subsequent known amount of each capture probe in the balanced set of capture probes. In some embodiments, minimization of the difference is constrained by a minimum subsequent amount or a maximum subsequent amount of each capture probe. In some embodiments, the desired sequencing depth profile is uniform. In some embodiments, the desired sequencing depth profile is non-uniform. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecule is a cell-free DNA molecule, such as a ctDNA molecule or a cfDNA molecule.

In some embodiments, there is provided a method of identifying an error in a nucleic acid sequence, comprising sequencing a set of amplified first strands formed from a first strand of a duplex nucleic acid molecule, resulting in a set of first strand reads; sequencing a set of amplified second strands formed from a second strand of the duplex nucleic acid molecule, resulting in a set of second strand reads; constructing a first strand consensus sequence using the set of first strand reads; constructing a second strand consensus sequence using the set of second strand reads; and comparing the first strand consensus sequence to the second strand consensus sequence; wherein the duplex nucleic acid molecule is ligated to a sequencing adapter prior to being amplified; and the sequencing adapter is randomly selected from a plurality of sequencing adapters comprising a duplex molecular barcode with a predetermined sequence; and wherein the duplex nucleic acid molecule is enriched using a set of capture probes for a region of interest, wherein the set of capture probes is prepared by sequencing a reference sequencing library comprising a plurality of nucleic acid molecules enriched using a first set of capture probes, wherein each capture probe comprises a sequence that is substantially complementary to a portion of or adjacent to a region of interest included in the reference sequencing library, and wherein an initial known amount of each capture probe is used to form the first set of capture probes; determining a sequencing depth attributable to each capture probe; selecting a subsequent known amount of each capture probe based on the initial known amount and the sequencing depth attributable to said capture probe, wherein the subsequent known amount of each capture probe is selected to minimize a difference between a predicted sequencing depth profile and a desired sequencing depth profile; and constructing the balanced set of capture probes by combining at least a fraction of the capture probes at the subsequent known amount of each capture probe in the balanced set of capture probes. In some embodiments, minimization of the difference is constrained by a minimum subsequent amount or a maximum subsequent amount of each capture probe. In some embodiments, the desired sequencing depth profile is uniform. In some embodiments, the desired sequencing depth profile is non-uniform. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecule is a cell-free DNA molecule, such as a ctDNA molecule or a cfDNA molecule.

In some embodiments, there is provided a method of identifying an error in a nucleic acid sequence, comprising sequencing a first strand of a duplex nucleic acid molecule, resulting in a first strand read; sequencing a second strand of the duplex nucleic acid molecule, resulting in a second strand read; comparing the first strand read to the second strand read; wherein the duplex nucleic acid molecule is ligated to a sequencing adapter; and the sequencing adapter is randomly selected from a plurality of sequencing adapters comprising a first sequencing adapter comprising a first duplex molecular barcode n nucleotides in length; and a second sequencing adapter comprising a second duplex molecular barcode n+x nucleotides in length, wherein x is not zero; and wherein the duplex nucleic acid molecule is enriched using a set of capture probes for a region of interest, wherein the set of capture probes is prepared by sequencing a reference sequencing library comprising a plurality of nucleic acid molecules enriched using a first set of capture probes, wherein each capture probe comprises a sequence that is substantially complementary to a portion of or adjacent to a region of interest included in the reference sequencing library, and wherein an initial known amount of each capture probe is used to form the first set of capture probes; determining a sequencing depth attributable to each capture probe; selecting a subsequent known amount of each capture probe based on the initial known amount and the sequencing depth attributable to said capture probe, wherein the subsequent known amount of each capture probe is selected to minimize a difference between a predicted sequencing depth profile and a desired sequencing depth profile; and constructing the balanced set of capture probes by combining at least a fraction of the capture probes at the subsequent known amount of each capture probe in the balanced set of capture probes. In some embodiments, minimization of the difference is constrained by a minimum subsequent amount or a maximum subsequent amount of each capture probe. In some embodiments, the desired sequencing depth profile is uniform. In some embodiments, the desired sequencing depth profile is non-uniform. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecule is a cell-free DNA molecule, such as a ctDNA molecule or a cfDNA molecule.

In some embodiments, there is provided a method of identifying an error in a nucleic acid sequence, comprising sequencing a set of amplified first strands formed from a first strand of a duplex nucleic acid molecule, resulting in a set of first strand reads; sequencing a set of amplified second strands formed from a second strand of the duplex nucleic acid molecule, resulting in a set of second strand reads; constructing a first strand consensus sequence using the set of first strand reads; constructing a second strand consensus sequence using the set of second strand reads; and comparing the first strand consensus sequence to the second strand consensus sequence; wherein the duplex nucleic acid molecule is ligated to a sequencing adapter prior to being amplified; and the sequencing adapter is randomly selected from a plurality of sequencing adapters comprising a first sequencing adapter comprising a first duplex molecular barcode n nucleotides in length; and a second sequencing adapter comprising a second duplex molecular barcode n+x nucleotides in length, wherein x is not zero; and wherein the duplex nucleic acid molecule is enriched using a set of capture probes for a region of interest, wherein the set of capture probes is prepared by sequencing a reference sequencing library comprising a plurality of nucleic acid molecules enriched using a first set of capture probes, wherein each capture probe comprises a sequence that is substantially complementary to a portion of or adjacent to a region of interest included in the reference sequencing library, and wherein an initial known amount of each capture probe is used to form the first set of capture probes; determining a sequencing depth attributable to each capture probe; selecting a subsequent known amount of each capture probe based on the initial known amount and the sequencing depth attributable to said capture probe, wherein the subsequent known amount of each capture probe is selected to minimize a difference between a predicted sequencing depth profile and a desired sequencing depth profile; and constructing the balanced set of capture probes by combining at least a fraction of the capture probes at the subsequent known amount of each capture probe in the balanced set of capture probes. In some embodiments, minimization of the difference is constrained by a minimum subsequent amount or a maximum subsequent amount of each capture probe. In some embodiments, the desired sequencing depth profile is uniform. In some embodiments, the desired sequencing depth profile is non-uniform. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecule is a cell-free DNA molecule, such as a ctDNA molecule or a cfDNA molecule.

In some embodiments, there is provided a method of determining the number of unique nucleic acid molecules in a nucleic acid library, comprising sequencing a set of amplified first strands formed from a first strand of a duplex nucleic acid molecule, resulting in a set of first strand reads; compiling the set of first strand reads; and counting the number of sets of nucleic acid molecule reads; wherein the duplex nucleic acid molecule is ligated to a sequencing adapter prior to being amplified; and the sequencing adapter is randomly selected from a plurality of sequencing adapters comprising a duplex molecular barcode with a predetermined sequence; and wherein the duplex nucleic acid molecule is enriched using a set of capture probes for a region of interest, wherein the set of capture probes is prepared by sequencing a reference sequencing library comprising a plurality of nucleic acid molecules enriched using a first set of capture probes, wherein each capture probe comprises a sequence that is substantially complementary to a portion of or adjacent to a region of interest included in the reference sequencing library, and wherein an initial known amount of each capture probe is used to form the first set of capture probes; determining a sequencing depth attributable to each capture probe; selecting a subsequent known amount of each capture probe based on the initial known amount and the sequencing depth attributable to said capture probe, wherein the subsequent known amount of each capture probe is selected to minimize a difference between a predicted sequencing depth profile and a desired sequencing depth profile; and constructing the balanced set of capture probes by combining at least a fraction of the capture probes at the subsequent known amount of each capture probe in the balanced set of capture probes. In some embodiments, minimization of the difference is constrained by a minimum subsequent amount or a maximum subsequent amount of each capture probe. In some embodiments, the desired sequencing depth profile is uniform. In some embodiments, the desired sequencing depth profile is non-uniform. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecules comprise cell-free DNA molecules, such as ctDNA molecules or cfDNA molecules.

In some embodiments, there is provided a method of determining the number of unique nucleic acid molecules in a sequencing library, comprising sequencing a set of amplified first strands formed from a first strand of a duplex nucleic acid molecule, resulting in a set of first strand reads; compiling the set of first strand reads; and counting the number of sets of nucleic acid molecule reads; wherein the duplex nucleic acid molecule is ligated to a sequencing adapter prior to being amplified; and the sequencing adapter is randomly selected from a plurality of sequencing adapters comprising a first sequencing adapter comprising a first duplex molecular barcode n nucleotides in length; and a second sequencing adapter comprising a second duplex molecular barcode n+x nucleotides in length, wherein x is not zero; and wherein the duplex nucleic acid molecule is enriched using a set of capture probes for a region of interest, wherein the set of capture probes is prepared by sequencing a reference sequencing library comprising a plurality of nucleic acid molecules enriched using a first set of capture probes, wherein each capture probe comprises a sequence that is substantially complementary to a portion of or adjacent to a region of interest included in the reference sequencing library, and wherein an initial known amount of each capture probe is used to form the first set of capture probes; determining a sequencing depth attributable to each capture probe; selecting a subsequent known amount of each capture probe based on the initial known amount and the sequencing depth attributable to said capture probe, wherein the subsequent known amount of each capture probe is selected to minimize a difference between a predicted sequencing depth profile and a desired sequencing depth profile; and constructing the balanced set of capture probes by combining at least a fraction of the capture probes at the subsequent known amount of each capture probe in the balanced set of capture probes. In some embodiments, minimization of the difference is constrained by a minimum subsequent amount or a maximum subsequent amount of each capture probe. In some embodiments, the desired sequencing depth profile is uniform. In some embodiments, the desired sequencing depth profile is non-uniform. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecules comprise cell-free DNA molecules, such as ctDNA molecules or cfDNA molecules.

In some embodiments, there is provided a method of determining the number of unique nucleic acid molecules in a sequencing library, comprising sequencing a set of amplified first strands formed from a first strand of a duplex nucleic acid molecule, resulting in a set of first strand reads; sequencing a set of amplified second strands formed from a second strand of a duplex nucleic acid molecule, resulting in a set of second strand reads; compiling the set of first strand reads; compiling the set of second strand reads; matching the set of first strand reads to the set of second strand reads; and counting the number of matched sets; wherein the duplex nucleic acid molecule is ligated to a sequencing adapter prior to being amplified; and the sequencing adapter is randomly selected from a plurality of sequencing adapters comprising a duplex molecular barcode with a predetermined sequence; and wherein the duplex nucleic acid molecule is enriched using a set of capture probes for a region of interest, wherein the set of capture probes is prepared by sequencing a reference sequencing library comprising a plurality of nucleic acid molecules enriched using a first set of capture probes, wherein each capture probe comprises a sequence that is substantially complementary to a portion of or adjacent to a region of interest included in the reference sequencing library, and wherein an initial known amount of each capture probe is used to form the first set of capture probes; determining a sequencing depth attributable to each capture probe; selecting a subsequent known amount of each capture probe based on the initial known amount and the sequencing depth attributable to said capture probe, wherein the subsequent known amount of each capture probe is selected to minimize a difference between a predicted sequencing depth profile and a desired sequencing depth profile; and constructing the balanced set of capture probes by combining at least a fraction of the capture probes at the subsequent known amount of each capture probe in the balanced set of capture probes. In some embodiments, minimization of the difference is constrained by a minimum subsequent amount or a maximum subsequent amount of each capture probe. In some embodiments, the desired sequencing depth profile is uniform. In some embodiments, the desired sequencing depth profile is non-uniform. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecules comprise cell-free DNA molecules, such as ctDNA molecules or cfDNA molecules.

In some embodiments, there is provided a method of determining the number of unique nucleic acid molecules in a sequencing library, comprising sequencing a set of amplified first strands formed from a first strand of a duplex nucleic acid molecule, resulting in a set of first strand reads; sequencing a set of amplified second strands formed from a second strand of a duplex nucleic acid molecule, resulting in a set of second strand reads; compiling the set of first strand reads; compiling the set of second strand reads; matching the set of first strand reads to the set of second strand reads; and counting the number of matched sets; wherein the duplex nucleic acid molecule is ligated to a sequencing adapter prior to being amplified; and the sequencing adapter is randomly selected from a plurality of sequencing adapters comprising a first sequencing adapter comprising a first duplex molecular barcode n nucleotides in length; and a second sequencing adapter comprising a second duplex molecular barcode n+x nucleotides in length, wherein x is not zero; and wherein the duplex nucleic acid molecule is enriched using a set of capture probes for a region of interest, wherein the set of capture probes is prepared by sequencing a reference sequencing library comprising a plurality of nucleic acid molecules enriched using a first set of capture probes, wherein each capture probe comprises a sequence that is substantially complementary to a portion of or adjacent to a region of interest included in the reference sequencing library, and wherein an initial known amount of each capture probe is used to form the first set of capture probes; determining a sequencing depth attributable to each capture probe; selecting a subsequent known amount of each capture probe based on the initial known amount and the sequencing depth attributable to said capture probe, wherein the subsequent known amount of each capture probe is selected to minimize a difference between a predicted sequencing depth profile and a desired sequencing depth profile; and constructing the balanced set of capture probes by combining at least a fraction of the capture probes at the subsequent known amount of each capture probe in the balanced set of capture probes. In some embodiments, minimization of the difference is constrained by a minimum subsequent amount or a maximum subsequent amount of each capture probe. In some embodiments, the desired sequencing depth profile is uniform. In some embodiments, the desired sequencing depth profile is non-uniform. In some embodiments, the sequencing adapters further comprise a constant 3'-overhang (such as a thymine nucleotide). In some embodiments, the molecular barcodes are color balanced or base-composition balanced. In some embodiments, the plurality of sequencing adapters comprises between about 2 and about 500 unique molecular barcodes. In some embodiments, the edit distance between each molecular barcode is 2 or more. In some embodiments, the sequencing adapters comprise a sample index (which may be included in the sequencing adapter before ligation or incorporated into the sequencing adapter during amplification). In some embodiments, the sample index comprises a first portion and a second portion (which may be on the same nucleic acid strand or on different nucleic acid strands of the sequencing adapter). In some embodiments, the plurality of sequence adapters comprises Y-shaped sequencing adapters, U-shaped sequencing adapters, or a combination thereof. In some embodiments, the nucleic acid molecules comprise cell-free DNA molecules, such as ctDNA molecules or cfDNA molecules.

EMBODIMENTS

Embodiment 1

A method of sequencing a nucleic acid molecule, comprising:
sequencing a first strand of a duplex nucleic acid molecule, resulting in a first strand read;
wherein the duplex nucleic acid molecule is ligated to a sequencing adapter prior to being amplified; and the sequencing adapter is randomly selected from a plurality of sequencing adapters comprising a duplex molecular barcode with a predetermined sequence.

Embodiment 2

A method of sequencing a nucleic acid molecule, comprising:
sequencing a set of amplified first strands formed from a first strand of a duplex nucleic acid molecule, resulting in a set of first strand reads; and
constructing a first strand consensus sequence using the set of first strand reads;
wherein the duplex nucleic acid molecule is ligated to a sequencing adapter prior to being amplified; and the sequencing adapter is randomly selected from a plu-

Embodiment 3

The method according to embodiment 1 or 2, wherein the plurality of sequencing adapters comprises:
- a first sequencing adapter comprising a first duplex molecular barcode n nucleotides in length with a predetermined sequence; and
- a second sequencing adapter comprising a second duplex molecular barcode n+x nucleotides in length with a predetermined sequence, wherein x is not zero.

Embodiment 4

A method of sequencing a nucleic acid molecule, comprising:
- sequencing a first strand of a duplex nucleic acid molecule, resulting in a first strand read;
- wherein the duplex nucleic acid molecule is ligated to a sequencing adapter; and the sequencing adapter is randomly selected from a plurality of sequencing adapters comprising:
  - a first sequencing adapter comprising a first duplex molecular barcode n nucleotides in length; and
  - a second sequencing adapter comprising a second duplex molecular barcode n+x nucleotides in length, wherein x is not zero.

Embodiment 5

A method of sequencing a nucleic acid molecule, comprising:
- sequencing a set of amplified first strands formed from a first strand of a duplex nucleic acid molecule, resulting in a set of first strand reads; and
- constructing a first strand consensus sequence using the set of first strand reads;
- wherein the duplex nucleic acid molecule is ligated to a sequencing adapter prior to being amplified; and the sequencing adapter is randomly selected from a plurality of sequencing adapters comprising:
  - a first sequencing adapter comprising a first duplex molecular barcode n nucleotides in length; and
  - a second sequencing adapter comprising a second duplex molecular barcode n+x nucleotides in length, wherein x is not zero.

Embodiment 6

The method of any one of embodiments 3-5, wherein the plurality of sequencing adapters further comprises a third sequencing adapter comprising a third duplex molecular barcode n+y nucleotides in length with a predetermined sequence, wherein y is not zero or x.

Embodiment 7

The method of embodiment 6, wherein x is 1 and y is 2.

Embodiment 8

The method of any one of embodiments 3-7, wherein n is between 8 and 16.

Embodiment 9

The method of any one of embodiments 3-8, wherein n is 12.

Embodiment 10

The method of any one of embodiments 1-7, further comprising amplifying the first strand of the duplex nucleic acid molecule.

Embodiment 11

The method of any one of embodiments 2, 3, and 5-10, further comprising compiling the set of first strand reads.

Embodiment 12

The method of embodiment 11, wherein the set of first strand reads is compiled based on sequence distance or alignment to a reference sequence.

Embodiment 13

The method of any one of embodiments 2, 3, and 5-12, wherein constructing the first strand consensus sequence comprises:
- comparing the first strand reads in the set of first strand reads;
- identifying and removing errors in the set of first strand reads; and
- constructing an error-corrected first-strand consensus sequence.

Embodiment 14

The method of any one of embodiments 2, 3, and 5-12, wherein constructing the first strand consensus sequence comprises:
- constructing a first strand consensus sequence from the set of first strand reads;
- comparing the first strand consensus sequence to the set of first strand reads;
- identifying and removing errors in the set of first strand reads; and
- constructing an error-corrected first strand consensus sequence.

Embodiment 15

The method of any one of embodiments 1-14, wherein the first strand is sequenced in a first direction and a second direction.

Embodiment 16

The method of any one of embodiments 2, 3, and 5-15, further comprising:
- sequencing a set of amplified second strands formed from a second strand of the duplex nucleic acid molecule, resulting in a set of second strand reads; and constructing a second strand consensus sequence using the set of second strand reads.

Embodiment 17

The method of embodiment 16, wherein the second strand is sequenced in a first direction and a second direction.

Embodiment 18

The method of embodiment 16 or 17, further comprising amplifying the second strand of the duplex nucleic acid molecule to form the amplified second strands.

Embodiment 19

The method of any one of embodiments 16-18, further comprising compiling the set of second strand reads.

Embodiment 20

The method of any one of embodiments 16-19, further comprising compiling the set of second strand reads based on sequence distance or alignment to a reference sequence.

Embodiment 21

The method of any one of embodiments 16-20, further comprising:
 comparing the first strand consensus sequence and the second strand consensus sequence;
 identifying and removing errors in the set of first strand reads and the set of second strand reads; and
 constructing an error-corrected duplex consensus sequence.

Embodiment 22

The method of any one of embodiments 1-21, further comprising ligating sequencing adapters from the plurality of sequencing adapters to duplex nucleic acid molecules.

Embodiment 23

The method of any one of embodiments 1-22, wherein the sequencing adapters in the plurality of sequence adapters comprise a first constant 3'-overhang, and the duplex nucleic acid molecule comprises a second constant 3'-overhang complementary to the first 3'-overhang prior to ligation.

Embodiment 24

The method of embodiment 23, wherein the first constant 3'-overhang is a thymine nucleotide and the second constant 3'-overhang is an adenine nucleotide.

Embodiment 25

The method of any one of embodiments 1-24, wherein the number of unique molecular barcodes in the plurality of sequencing adapters is between 2 and about 500.

Embodiment 26

The method of any one of embodiments 1-25, wherein the ratio of A/C to G/T nucleotides at any given position of the molecular barcodes is between about 2:1 and about 1:2 at the corresponding position relative to the length of the shortest molecular barcode in the plurality of sequencing adapters.

Embodiment 27

The method of any one of embodiments 1-26, wherein the ratio of A/C to G/T nucleotides at any given position of the molecular barcodes is about 1:1 at the corresponding position relative to the shortest molecular barcode in the plurality of sequencing adapters.

Embodiment 28

The method of any one of embodiments 1-27, wherein:
 the proportion of adenine at any given position of the molecular barcodes is between 0.2 and 0.4 at the corresponding position relative to the shortest molecular barcode in the plurality of sequencing adapters;
 the proportion of cytosine at any given position of the molecular barcodes is between 0.2 and 0.4 at the corresponding position relative to the shortest molecular barcode in the plurality of sequencing adapters;
 the proportion of thymine at any given position of the molecular barcodes is between 0.2 and 0.4 at the corresponding position relative to the shortest molecular barcode in the plurality of sequencing adapters; and
 the proportion of guanine at any given position of the molecular barcodes is between 0.2 and 0.4 at the corresponding position relative to the shortest molecular barcode in the plurality of sequencing adapters.

Embodiment 29

The method of any one of embodiments 1-28, wherein:
 the proportion of adenine within any given molecular barcodes is between 0.2 and 0.3;
 the proportion of cytosine within any given molecular barcodes is between 0.2 and 0.3;
 the proportion of thymidine within any given molecular barcodes is between 0.2 and 0.3; and
 the proportion of guanine within any given molecular barcodes is between 0.2 and 0.3.

Embodiment 30

The method of any one of embodiments 1-29, wherein the edit distance between each molecular barcode is 2 or more.

Embodiment 31

The method of any one of embodiments 1-30, wherein the sequencing adapters in the composition comprise a primer annealing site.

Embodiment 32

The method of any one of embodiments 1-31, wherein the sequencing adapters comprise a sample index nucleic acid sequence.

Embodiment 33

The method of embodiment 32, wherein the sample index is incorporated into the sequencing adapter by amplifying the nucleic acid molecule.

Embodiment 34

The method of embodiment 32, wherein the sample index is ligated to the sequencing adapter.

Embodiment 35

The method of any one of embodiments 32-34, wherein the sample index nucleic acid sequence comprises a first portion and a second portion.

Embodiment 36

The method of embodiment 35, wherein:
the first portion is within a first nucleic strand; and
the second portion is within a second nucleic acid strand.

Embodiment 37

The method of any one of embodiments 32-36, wherein the sample index nucleic acid sequence is between about 6 and about 20 nucleotides in length.

Embodiment 38

The method of any one of embodiments 32-37, wherein the first portion and the second portion are each between about 3 and about 10 nucleotides in length.

Embodiment 39

The method of any one of embodiments 35-38, wherein the first portion and the second portion are of equal length.

Embodiment 40

The method of any one of embodiments 32-39, wherein the sample index nucleic acid sequence is about 16 nucleotides in length.

Embodiment 41

The method of any one of embodiments 32-40, wherein:
the proportion of adenine within the sample index nucleic acid sequence is between 0.2 and 0.4;
the proportion of cytosine within the sample index nucleic acid sequence is between 0.2 and 0.4;
the proportion of thymidine within the sample index nucleic acid sequence is between 0.2 and 0.4; and
the proportion of guanine within the sample index nucleic acid sequence is between 0.2 and 0.4.

Embodiment 42

The method of any one of embodiments 1-41, wherein the plurality of sequence adapters comprises U-shaped sequence adapters, Y-shaped sequence adapters, or a combination thereof.

Embodiment 43

A method of identifying an error in a nucleic acid sequence, comprising:
sequencing a first strand of a duplex nucleic acid molecule, resulting in a first strand read;
sequencing a second strand of the duplex nucleic acid molecule, resulting in a second strand read; and
comparing the first strand read to the second strand read;
wherein the duplex nucleic acid molecule is ligated to a sequencing adapter; and the sequencing adapter is randomly selected from a plurality of sequencing adapters comprising a duplex molecular barcode with a predetermined sequence.

Embodiment 44

A method of identifying an error in a nucleic acid sequence, comprising:
sequencing a set of amplified first strands formed from a first strand of a duplex nucleic acid molecule, resulting in a set of first strand reads;
sequencing a set of amplified second strands formed from a second strand of the duplex nucleic acid molecule, resulting in a set of second strand reads;
constructing a first strand consensus sequence using the set of first strand reads;
constructing a second strand consensus sequence using the set of second strand reads; and
comparing the first strand consensus sequence to the second strand consensus sequence;
wherein the duplex nucleic acid molecule is ligated to a sequencing adapter prior to being amplified; and the sequencing adapter is randomly selected from a plurality of sequencing adapters comprising a duplex molecular barcode with a predetermined sequence.

Embodiment 45

A method of identifying an error in a nucleic acid sequence, comprising:
sequencing a first strand of a duplex nucleic acid molecule, resulting in a first strand read;
sequencing a second strand of the duplex nucleic acid molecule, resulting in a second strand read;
comparing the first strand read to the second strand read;
wherein the duplex nucleic acid molecule is ligated to a sequencing adapter; and the sequencing adapter is randomly selected from a plurality of sequencing adapters comprising:
a first sequencing adapter comprising a first duplex molecular barcode n nucleotides in length; and
a second sequencing adapter comprising a second duplex molecular barcode n+x nucleotides in length, wherein x is not zero.

Embodiment 46

A method of identifying an error in a nucleic acid sequence, comprising:
sequencing a set of amplified first strands formed from a first strand of a duplex nucleic acid molecule, resulting in a set of first strand reads;
sequencing a set of amplified second strands formed from a second strand of the duplex nucleic acid molecule, resulting in a set of second strand reads;
constructing a first strand consensus sequence using the set of first strand reads;
constructing a second strand consensus sequence using the set of second strand reads; and
comparing the first strand consensus sequence to the second strand consensus sequence;
wherein the duplex nucleic acid molecule is ligated to a sequencing adapter prior to being amplified; and the sequencing adapter is randomly selected from a plurality of sequencing adapters comprising:
a first sequencing adapter comprising a first duplex molecular barcode n nucleotides in length; and
a second sequencing adapter comprising a second duplex molecular barcode n+x nucleotides in length, wherein x is not zero.

Embodiment 47

The method according to any one of embodiments 43-46, wherein the first strand is sequenced in a first direction and a second direction.

Embodiment 48

The method according to embodiment 47, wherein the second strand is sequenced in a first direction and a second direction.

Embodiment 49

The method according to any one of embodiments 1-48, wherein the duplex nucleic acid molecule is ligated to two sequencing adapters.

Embodiment 50

The method according to any one of embodiments 1-49, wherein the duplex nucleic acid molecule is a cell-free DNA molecule.

Embodiment 51

The method according to embodiment 50, wherein the duplex nucleic acid molecule is a cell-free tumor DNA molecule or a cell-free fetal DNA molecule.

Embodiment 52

The method according to any one of embodiments 1-51, wherein the duplex nucleic acid molecule is enriched from a nucleic acid library.

Embodiment 53

The method according to embodiment 52, wherein the duplex nucleic acid molecule is enriched using a set of capture probes for a region of interest.

Embodiment 54

The method of embodiment 53, wherein the set of capture probes is balanced to provide a reduced sequencing depth variance relative to a set of capture probes comprising a plurality of approximately equally represented capture probes.

Embodiment 55

The method of embodiment 53 or 54, wherein the set of capture probes is prepared by:
sequencing a reference sequencing library comprising a plurality of nucleic acid molecules enriched using a first set of capture probes, wherein each capture probe comprises a sequence that is substantially complementary to a portion of or adjacent to a region of interest included in the reference sequencing library, and wherein an initial known amount of each capture probe is used to form the first set of capture probes;
determining a sequencing depth attributable to each capture probe;
selecting a subsequent known amount of each capture probe based on the initial known amount and the sequencing depth attributable to said capture probe, wherein the subsequent known amount of each capture probe is selected to minimize a difference between a predicted sequencing depth profile and a desired sequencing depth profile; and
constructing the balanced set of capture probes by combining at least a fraction of the capture probes at the subsequent known amount of each capture probe in the balanced set of capture probes.

Embodiment 56

The method of embodiment 55, wherein minimization of the difference is constrained by a minimum subsequent amount or a maximum subsequent amount of each capture probe.

Embodiment 57

The method of embodiment 55 or 56, wherein the desired sequencing depth profile is uniform.

Embodiment 58

The method of embodiment 55 or 56, wherein the desired sequencing depth profile is non-uniform.

Embodiment 59

The method of any one of embodiments 55-58, wherein the difference between the predicted sequencing depth profile and the desired sequencing depth profile is defined by an objective function.

Embodiment 60

The method of embodiment 59, wherein the desired sequencing depth profile is implied by the objective function.

Embodiment 61

The method of any one of embodiments 55-60, wherein the initial known amount is an initial known volume and the subsequent known amount is a subsequent known volume.

Embodiment 62

The method of any one of embodiments 55-61, wherein the initial known amount is an initial known mass or an initial known number of moles, and the subsequent known amount is a subsequent known mass or a subsequent known number of moles.

Embodiment 63

The method of any one of embodiments 55-62, wherein the initial known amount is an initial known relative amount and the subsequent known amount is a subsequent known relative amount.

Embodiment 64

The method of any one of embodiments 55-63, wherein the sequencing depth is based on a number of sequencing reads that comprise a sequence substantially complementary to a sequence within the capture probe.

Embodiment 65

The method of any one of embodiments 55-64, wherein the sequencing depth is based on a number of sequencing reads that comprise a sequence substantially complementary to at least half of the capture probe.

Embodiment 66

The method of embodiment 64 or 65, wherein the number of sequencing reads is a number of consensus sequencing reads.

Embodiment 67

The method of any one of embodiments 64-66, wherein the number of sequencing reads is a number of duplex consensus sequencing reads.

Embodiment 68

The method of any one of embodiments 55-67, wherein the capture probes are not substantially complementary to overlapping portions of the region of interest.

Embodiment 69

The method of any one of embodiments 55-68, wherein at least two capture probes in the plurality of capture probes are substantially complementary to overlapping portions of the region of interest.

Embodiment 70

The method of any one of embodiments 55-69, wherein the method comprises obtaining for each capture probe a binding fraction based on the sequencing depth attributable to the capture probe; and wherein the subsequent known amount is based on the initial known amount and the binding fraction.

Embodiment 71

The method of any one of embodiments 55-70, wherein the method comprises obtaining for each capture probe a binding fraction, wherein the binding fraction is determined for the fraction of nucleic acid molecules comprising a segment substantially complementary to at least half of the capture probe that bound to the capture probe during enrichment of the reference sequencing library based on the sequencing depth attributable to the capture probe; and wherein the subsequent known amount is based on the initial known amount and the fraction.

Embodiment 72

The method of embodiment 70 or 71, wherein obtaining the binding fraction comprises approximating the sequencing depth for a given capture probe i as a Poisson distribution:

$$d_{is} = \text{Poisson}(N_s \pi_i)$$

wherein:
  $d_{is}$ is the determined sequencing depth attributable to the capture probe i;
  $N_s$ is the number of nucleic acid molecules in reference sequencing library s; and
  $\pi_i$ is the binding fraction for capture probe i.

Embodiment 73

The method of embodiment 72, wherein $\pi_i$ is determined by fitting a maximum likelihood model or a Markov chain Monte Carlo model.

Embodiment 74

The method of any one of embodiments 55-73, wherein the difference is defined by an objective function of the subsequent amounts of the capture probes in the balanced set of capture probes, according to:

$$f(\vec{v}) = V(\vec{\pi}(\vec{v}))$$

wherein:

$$(\vec{\pi}(\vec{v}))_i = \left(1 + \frac{\gamma_i}{v_i c_i}\right)^{-1}$$

wherein:
  $V(\ )$ is a user-defined objective function for the set of capture probes;
  $(\vec{\pi}(\vec{v}))_i$ is the binding fraction for capture probe i for the vector $\vec{\pi}(\vec{v})$;
  $c_i$ is an effective concentration for capture probe i for the vector $\vec{\pi}(\vec{v})$;
  $v_i$ is the subsequent amount of capture probe i for the vector $\vec{\pi}(\vec{v})$; and
  $\gamma_i$ is the initial amount of capture probe i for the vector $\vec{\pi}(\vec{v})$.

Embodiment 75

The method of any one of embodiments 55-74, wherein the difference is an objective function defined by a coefficient of variation.

Embodiment 76

The method of any one of embodiments 55-75, further comprising:
  enriching the reference sequencing library using the balanced set of capture probes;
  sequencing the reference sequencing library enriched using the balanced set of capture probes;
  determining a sequencing depth attributable to each capture probe in the balanced set of capture probes;
  selecting a second subsequent known amount of each capture probe based on the subsequent known amount of said capture probe in the balanced set of capture probes and the sequencing depth attributable to said capture probe, wherein the second subsequent known amount of each capture probe is selected to minimize a difference between a second predicted sequencing depth profile and the desired sequencing depth profile; and constructing a re-balanced set of capture probes by combining at least a fraction of the capture probes at the second subsequent known amount of each capture probe in the re-balanced set of capture probes.

Embodiment 77

The method of embodiment 76, wherein minimization of the difference is constrained by a minimum second subsequent amount or a maximum second subsequent amount of each capture probe.

Embodiment 78

The method of any one of embodiments 55-77, wherein constructing the balanced set of capture probes comprises combining each capture probe in the first set of capture probes at the subsequent known amount of each capture probe in the balanced set capture probe.

Embodiment 79

A composition comprising a plurality of sequencing adapters comprising a duplex molecular barcode having a nondegenerate sequence.

Embodiment 80

The composition according to embodiment 79, wherein the plurality of sequencing adapters comprises:
a first sequencing adapter comprising a first duplex molecular barcode n nucleotides in length; and
a second sequencing adapter comprising a second duplex molecular barcode n+x nucleotides in length, wherein x is not zero.

Embodiment 81

A composition comprising:
a first sequencing adapter comprising a first duplex molecular barcode n nucleotides in length; and
a second sequencing adapter comprising a second duplex molecular barcode n+x nucleotides in length, wherein x is not zero.

Embodiment 82

The composition of embodiment 80 or 81, wherein the composition further comprises a third sequencing adapter comprising a third molecular barcode comprising a nucleic acid duplex n+y nucleotides in length, wherein y is not zero or x.

Embodiment 83

The composition of embodiment 82, wherein x is 1 and y is 2.

Embodiment 84

The composition of any one of embodiments 80-83, wherein n is between 8 and 16.

Embodiment 85

The composition of any one of embodiments 80-84, wherein n is 12.

Embodiment 86

The composition of any one of embodiments 79-85, wherein the sequencing adapters in the composition comprise a constant 3'-overhang.

Embodiment 87

The composition of embodiment 86, wherein the constant 3'-overhang is a thymine nucleotide.

Embodiment 88

The composition of any one of embodiments 79-87, wherein the number of unique molecular barcodes in the plurality of sequencing adapters is between 2 and about 500.

Embodiment 89

The composition of any one of embodiments 79-88, wherein the ratio of A/C to G/T nucleotides at any given position of the molecular barcodes is between about 2:1 and about 1:2 at the corresponding position relative to the shortest molecular barcode in the plurality of sequencing adapters.

Embodiment 90

The composition of any one of embodiments 79-89, wherein the ratio of A/C to G/T nucleotides at any given position of the molecular barcodes is about 1:1 at the corresponding position relative to the shortest molecular barcode in the plurality of sequencing adapters.

Embodiment 91

The composition of any one of embodiments 79-90, wherein:
the proportion of adenine at any given position of the molecular barcodes is between 0.2 and 0.4 at the corresponding position relative to the shortest molecular barcode in the plurality of sequencing adapters;
the proportion of cytosine at any given position of the molecular barcodes is between 0.2 and 0.4 at the corresponding position relative to the shortest molecular barcode in the plurality of sequencing adapters;
the proportion of thymine at any given position of the molecular barcodes is between 0.2 and 0.4 at the corresponding position relative to the shortest molecular barcode in the plurality of sequencing adapters; and
the proportion of guanine at any given position of the molecular barcodes is between 0.2 and 0.4 at the corresponding position relative to the shortest molecular barcode in the plurality of sequencing adapters.

Embodiment 92

The composition of any one of embodiments 79-91, wherein the proportion of adenine within any given molecular barcodes is between 0.2 and 0.4;
the proportion of cytosine within any given molecular barcodes is between 0.2 and 0.4;

the proportion of thymidine within any given molecular barcodes is between 0.2 and 0.4; and the proportion of guanine within any given molecular barcodes is between 0.2 and 0.4.

Embodiment 93

The composition of any one of embodiments 79-92, wherein the edit distance between each molecular barcode is 2 or more.

Embodiment 94

The composition of any one of embodiments 79-93, wherein the sequencing adapters in the composition comprise a primer annealing site.

Embodiment 95

The composition of any one of embodiments 79-94, wherein the sequencing adapters comprise a sample index.

Embodiment 96

The composition of embodiment 95, wherein the sample index comprises a first portion and a second portion.

Embodiment 97

The composition of embodiment 96, wherein:
the first portion is within a first nucleic strand; and
the second portion is within a second nucleic acid strand.

Embodiment 98

The composition of any one of embodiments 95-97, wherein the sample index is between about 6 and about 20 nucleotides in length.

Embodiment 99

The composition of any one of embodiments 95-98, wherein the first portion and the second portion are each between about 3 and about 10 nucleotides in length.

Embodiment 100

The composition of any one of embodiments 96-99, wherein the first portion and the second portion are of equal length.

Embodiment 101

The composition of any one of embodiments 96-100, wherein the sample index is about 16 nucleotides in length.

Embodiment 102

The composition of any one of embodiments 96-101, wherein:
the proportion of adenine within the sample index is between 0.2 and 0.4;
the proportion of cytosine within the sample index is between 0.2 and 0.4;
the proportion of thymine within the sample index is between 0.2 and 0.4; and
the proportion of guanine within the sample index is between 0.2 and 0.4.

Embodiment 103

The composition of any one of embodiments 79-102, wherein the plurality of sequence adapters comprises U-shaped sequencing adapters, Y-shaped sequencing adapters, or a combination thereof.

Embodiment 104

A nucleic acid sequencing library comprising a plurality of nucleic acid inserts ligated to at least one sequencing adapter randomly selected from a plurality of sequencing adapters comprising a duplex molecular barcode having a nondegenerate sequence.

Embodiment 105

The nucleic acid sequencing library according to embodiment 104, wherein the plurality of sequencing adapters comprises:
a first sequencing adapter comprising a first molecular barcode comprising a nucleic acid duplex n nucleotides in length; and
a second sequencing adapter comprising a second molecular barcode comprising a nucleic acid duplex n+x nucleotides in length, wherein x is not zero.

Embodiment 106

A nucleic acid sequencing library comprising a plurality of nucleic acid inserts ligated to at least one sequencing adapter, wherein the sequencing adapter is randomly selected from a plurality of sequencing adapters;
wherein the plurality of sequencing adapters comprises:
a first sequencing adapter comprising a first molecular barcode comprising a nucleic acid duplex n nucleotides in length; and
a second sequencing adapter comprising a second molecular barcode comprising a nucleic acid duplex n+x nucleotides in length, wherein x is not zero.

Embodiment 107

The nucleic acid sequencing library of any one of embodiments 104-106, wherein the nucleic acid inserts in the plurality of nucleic acid inserts are ligated to two sequencing adapters from the plurality of sequencing adapters.

Embodiment 108

The nucleic acid sequencing library of any one of embodiments 104-107, wherein the sequencing adapters comprise a sample index.

Embodiment 109

The nucleic acid sequencing library of any one of embodiments 104-108, wherein the nucleic acid inserts comprise a cell-free DNA molecule.

Embodiment 110

The nucleic acid sequencing library of embodiment 109, wherein the nucleic acid inserts comprise a cell-free tumor DNA molecule or a cell-free fetal DNA molecule.

Embodiment 111

The nucleic acid sequencing library of any one of embodiments 104-110, wherein the nucleic acid inserts are enriched from a nucleic acid library.

Embodiment 112

The nucleic acid sequencing library of embodiment 111, wherein the nucleic acid inserts are enriched using a set of capture probes for a region of interest.

Embodiment 113

The nucleic acid sequencing library of embodiment 112, wherein the set of capture probes is balanced to provide a reduced sequencing depth variance relative to a set of capture probes comprising a plurality of approximately equally represented capture probes.

Embodiment 114

The nucleic acid sequencing library of embodiment 112 or 113, wherein the set of capture probes is prepared by:
  sequencing a reference sequencing library comprising a plurality of nucleic acid molecules enriched using a first set of capture probes, wherein each capture probe comprises a sequence that is substantially complementary to a portion of or adjacent to a region of interest included in the reference sequencing library, and wherein an initial known amount of each capture probe is used to form the first set of capture probes;
  determining a sequencing depth attributable to each capture probe;
  selecting a subsequent known amount of each capture probe based on the initial known amount and the sequencing depth attributable to said capture probe, wherein the subsequent known amount of each capture probe is selected to minimize a difference between a predicted sequencing depth profile and a desired sequencing depth profile; and
  constructing the balanced set of capture probes by combining at least a fraction of the capture probes at the subsequent known amount of each capture probe in the balanced set of capture probes.

Embodiment 115

The nucleic acid sequencing library of embodiment 114, wherein minimization of the difference is constrained by a minimum subsequent amount or a maximum subsequent amount of each capture probe.

Embodiment 116

The nucleic acid sequencing library of embodiment 114 or 115, wherein the desired sequencing depth profile is uniform.

Embodiment 117

The nucleic acid sequencing library of embodiment 114 or 115, wherein the desired sequencing depth profile is non-uniform.

Embodiment 118

The nucleic acid sequencing library of any one of embodiments 114-117, wherein the difference between the predicted sequencing depth profile and the desired sequencing depth profile is defined by an objective function.

Embodiment 119

The nucleic acid sequencing library of embodiment 118, wherein the desired sequencing depth profile is implied by the objective function.

Embodiment 120

The nucleic acid sequencing library of any one of embodiments 114-119, wherein the initial known amount is an initial known volume and the subsequent known amount is a subsequent known volume.

Embodiment 121

The nucleic acid sequencing library of any one of embodiments 114-120, wherein the initial known amount is an initial known mass or an initial known number of moles, and the subsequent known amount is a subsequent known mass or a subsequent known number of moles.

Embodiment 122

The nucleic acid sequencing library of any one of embodiments 114-121, wherein the initial known amount is an initial known relative amount and the subsequent known amount is a subsequent known relative amount.

Embodiment 123

The nucleic acid sequencing library of any one of embodiments 114-122, wherein the sequencing depth is based on a number of sequencing reads that comprise a sequence substantially complementary to a sequence within the capture probe.

Embodiment 124

The nucleic acid sequencing library of any one of embodiments 114-123, wherein the sequencing depth is based on a number of sequencing reads that comprise a sequence substantially complementary to at least half of the capture probe.

Embodiment 125

The nucleic acid sequencing library of embodiment 123 or 124, wherein the number of sequencing reads is a number of consensus sequencing reads.

Embodiment 126

The nucleic acid sequencing library of any one of embodiments 123-125, wherein the number of sequencing reads is a number of duplex consensus sequencing reads.

Embodiment 127

The nucleic acid sequencing library of any one of embodiments 114-126, wherein the capture probes are not substantially complementary to overlapping portions of the region of interest.

Embodiment 128

The nucleic acid sequencing library of any one of embodiments 114-127, wherein at least two capture probes in the plurality of capture probes are substantially complementary to overlapping portions of the region of interest.

Embodiment 129

The nucleic acid sequencing library of any one of embodiments 114-128, wherein the method comprises obtaining for each capture probe a binding fraction based on the sequencing depth attributable to the capture probe; and wherein the subsequent known amount is based on the initial known amount and the binding fraction.

Embodiment 130

The nucleic acid sequencing library of any one of embodiments 114-129, wherein the method comprises obtaining for each capture probe a binding fraction, wherein the binding fraction is determined for the fraction of nucleic acid molecules comprising a segment substantially complementary to at least half of the capture probe that bound to the capture probe during enrichment of the reference sequencing library based on the sequencing depth attributable to the capture probe; and wherein the subsequent known amount is based on the initial known amount and the fraction.

Embodiment 131

The nucleic acid sequencing library of embodiment 129 or 130, wherein obtaining the binding fraction comprises approximating the sequencing depth for a given capture probe i as a Poisson distribution:

$$d_{is} = \text{Poisson}(N_s \pi_i)$$

wherein:
  $d_{is}$ is the determined sequencing depth attributable to the capture probe i;
  $N_s$ is the number of nucleic acid molecules in reference sequencing library s; and
  $\pi_i$ is the binding fraction for capture probe i.

Embodiment 132

The nucleic acid sequencing library of embodiment 131, wherein $\pi_i$ is determined by fitting a maximum likelihood model or a Markov chain Monte Carlo model.

Embodiment 133

The nucleic acid sequencing library of any one of embodiments 114-132, wherein the difference is defined by an objective function of the subsequent amounts of the capture probes in the balanced set of capture probes, according to:

$$f(\vec{v}) = V(\vec{\pi}(\vec{v}))$$

wherein:

$$(\vec{\pi}(\vec{v}))_i = \left(1 + \frac{\gamma_i}{v_i c_i}\right)^{-1}$$

wherein:
  $V(\ )$ is a user-defined objective function for the set of capture probes;
  $(\vec{\pi}(\vec{v}))_i$ is the binding fraction for capture probe i for the vector $\vec{\pi}(\vec{v})$;
  $c_i$ is an effective concentration for capture probe i for the vector $\vec{\pi}(\vec{v})$;
  $v_i$ is the subsequent amount of capture probe i for the vector $\vec{\pi}(\vec{v})$; and
  $\gamma_i$ is the initial amount of capture probe i for the vector $\vec{\pi}(\vec{v})$.

Embodiment 134

The nucleic acid sequencing library of any one of embodiments 114-133, wherein the difference is an objective function defined by a coefficient of variation.

Embodiment 135

The nucleic acid sequencing library of any one of embodiments 114-134, further comprising:
  enriching the reference sequencing library using the balanced set of capture probes;
  sequencing the reference sequencing library enriched using the balanced set of capture probes;
  determining a sequencing depth attributable to each capture probe in the balanced set of capture probes;
  selecting a second subsequent known amount of each capture probe based on the subsequent known amount of said capture probe in the balanced set of capture probes and the sequencing depth attributable to said capture probe, wherein the second subsequent known amount of each capture probe is selected to minimize a difference between a second predicted sequencing depth profile and the desired sequencing depth profile; and
  constructing a re-balanced set of capture probes by combining at least a fraction of the capture probes at the second subsequent known amount of each capture probe in the re-balanced set of capture probes.

Embodiment 136

The nucleic acid sequencing library of embodiment 135, wherein minimization of the difference is constrained by a minimum second subsequent amount or a maximum second subsequent amount of each capture probe.

Embodiment 137

The nucleic acid sequencing library of any one of embodiments 114-136, wherein constructing the balanced set of capture probes comprises combining each capture probe in the first set of capture probes at the subsequent known amount of each capture probe in the balanced set capture probe.

Embodiment 138

A pooled nucleic acid sequencing library comprising a first nucleic acid sequencing library and a second nucleic acid sequencing library,
  wherein the first nucleic acid sequencing library comprises a first plurality of nucleic acid inserts bound to at least one sequencing adapter from a first plurality of sequencing adapters comprising:
    a first duplex molecular barcode having a nondegenerate sequence; and
    a first sample index;

wherein the second nucleic acid sequencing library comprises a second plurality of nucleic acid inserts bound to at least one sequencing adapter from a second plurality of sequencing adapters comprising:
  a second duplex molecular barcode having a nondegenerate sequence; and
  a second sample index; and
wherein the first sample index and the second sample index are different.

Embodiment 139

The pooled nucleic acid sequencing library of embodiment 138, wherein the first molecular barcode and the second molecular barcode have the same sequence.

Embodiment 140

The pooled nucleic acid sequencing library of embodiment 138, wherein the first molecular barcode and the second molecular barcode have different sequences.

Embodiment 141

A pooled nucleic acid sequencing library comprising a first nucleic acid sequencing library and a second nucleic acid sequencing library,
  wherein the first nucleic acid sequencing library comprises a first plurality of nucleic acid inserts bound to at least one sequencing adapter from a first plurality of sequencing adapters comprising:
    a first sequencing adapter comprising a first molecular barcode comprising a nucleic acid duplex n nucleotides in length; and
    a second sequencing adapter comprising a second molecular barcode comprising a nucleic acid duplex n+x nucleotides in length, wherein x is not zero; and
    wherein the first sequencing adapter and the second sequencing adapter comprise a first sample index sequence
  wherein the second nucleic acid sequencing library comprises a second plurality of polynucleotides bound to at least one sequencing adapter from a second plurality of sequencing adapters comprising:
    a third sequencing adapter comprising a third molecular barcode comprising a nucleic acid duplex m nucleotides in length; and
    a fourth sequencing adapter comprising a fourth molecular barcode comprising a nucleic acid duplex m+a nucleotides in length, wherein a is not zero; and
    wherein the third sequencing adapter and the fourth sequencing adapter comprise a second sample index sequence
  wherein the first sample index sequence and the second sample index sequence are different.

Embodiment 142

The pooled nucleic acid sequencing library of embodiment 141, wherein the first molecular barcode and the third molecular barcode are the same.

Embodiment 143

The pooled nucleic acid sequencing library of embodiment 142, wherein the second molecular barcode and the fourth molecular barcode are the same.

Embodiment 144

The pooled nucleic acid sequencing library of any one of embodiments 138-143, wherein the nucleic acid inserts comprise a cell-free DNA molecule.

Embodiment 145

The pooled nucleic acid sequencing library of embodiment 144, wherein the nucleic acid inserts comprise a cell-free tumor DNA molecule or a cell-free fetal DNA molecule.

Embodiment 146

The pooled nucleic acid sequencing library of any one of embodiments 138-145, wherein the nucleic acid inserts are enriched from a nucleic acid library.

Embodiment 147

The pooled nucleic acid sequencing library of embodiment 146, wherein the nucleic acid inserts are enriched using a set of capture probes for a region of interest.

Embodiment 148

The pooled nucleic acid sequencing library of embodiment 147, wherein the set of capture probes is balanced to provide a reduced sequencing depth variance relative to a set of capture probes comprising a plurality of approximately equally represented capture probes.

Embodiment 149

The pooled nucleic acid sequencing library of embodiment 147 or 148, wherein the set of capture probes is prepared by:
  sequencing a reference sequencing library comprising a plurality of nucleic acid molecules enriched using a first set of capture probes, wherein each capture probe comprises a sequence that is substantially complementary to a portion of or adjacent to a region of interest included in the reference sequencing library, and wherein an initial known amount of each capture probe is used to form the first set of capture probes;
  determining a sequencing depth attributable to each capture probe;
  selecting a subsequent known amount of each capture probe based on the initial known amount and the sequencing depth attributable to said capture probe, wherein the subsequent known amount of each capture probe is selected to minimize a difference between a predicted sequencing depth profile and a desired sequencing depth profile; and
  constructing the balanced set of capture probes by combining at least a fraction of the capture probes at the subsequent known amount of each capture probe in the balanced set of capture probes.

Embodiment 150

The pooled nucleic acid sequencing library of embodiment 149, wherein minimization of the difference is constrained by a minimum subsequent amount or a maximum subsequent amount of each capture probe.

Embodiment 151

The pooled nucleic acid sequencing library of embodiment 149 or 150, wherein the desired sequencing depth profile is uniform

Embodiment 152

The pooled nucleic acid sequencing library of embodiment 149 or 150, wherein the desired sequencing depth profile is non-uniform.

Embodiment 153

The pooled nucleic acid sequencing library of any one of embodiments 149-152, wherein the difference between the predicted sequencing depth profile and the desired sequencing depth profile is defined by an objective function.

Embodiment 154

The pooled nucleic acid sequencing library of embodiment 153, wherein the desired sequencing depth profile is implied by the objective function.

Embodiment 155

The pooled nucleic acid sequencing library of any one of embodiments 149-154, wherein the initial known amount is an initial known volume and the subsequent known amount is a subsequent known volume.

Embodiment 156

The pooled nucleic acid sequencing library of any one of embodiments 149-155, wherein the initial known amount is an initial known mass or an initial known number of moles, and the subsequent known amount is a subsequent known mass or a subsequent known number of moles.

Embodiment 157

The pooled nucleic acid sequencing library of any one of embodiments 149-156, wherein the initial known amount is an initial known relative amount and the subsequent known amount is a subsequent known relative amount.

Embodiment 158

The pooled nucleic acid sequencing library of any one of embodiments 149-157, wherein the sequencing depth is based on a number of sequencing reads that comprise a sequence substantially complementary to a sequence within the capture probe.

Embodiment 159

The pooled nucleic acid sequencing library of any one of embodiments 149-158, wherein the sequencing depth is based on a number of sequencing reads that comprise a sequence substantially complementary to at least half of the capture probe.

Embodiment 160

The pooled nucleic acid sequencing library of embodiment 158 or 158, wherein the number of sequencing reads is a number of consensus sequencing reads.

Embodiment 161

The pooled nucleic acid sequencing library of any one of embodiments 158-160, wherein the number of sequencing reads is a number of duplex consensus sequencing reads.

Embodiment 162

The pooled nucleic acid sequencing library of any one of embodiments 149-161, wherein the capture probes are not substantially complementary to overlapping portions of the region of interest.

Embodiment 163

The pooled nucleic acid sequencing library of any one of embodiments 149-162, wherein at least two capture probes in the plurality of capture probes are substantially complementary to overlapping portions of the region of interest.

Embodiment 164

The pooled nucleic acid sequencing library of any one of embodiments 149-163, wherein the method comprises obtaining for each capture probe a binding fraction based on the sequencing depth attributable to the capture probe; and wherein the subsequent known amount is based on the initial known amount and the binding fraction.

Embodiment 165

The pooled nucleic acid sequencing library of any one of embodiments 149-164, wherein the method comprises obtaining for each capture probe a binding fraction, wherein the binding fraction is determined for the fraction of nucleic acid molecules comprising a segment substantially complementary to at least half of the capture probe that bound to the capture probe during enrichment of the reference sequencing library based on the sequencing depth attributable to the capture probe; and wherein the subsequent known amount is based on the initial known amount and the fraction.

Embodiment 166

The pooled nucleic acid sequencing library of embodiment 164 or 165, wherein obtaining the binding fraction comprises approximating the sequencing depth for a given capture probe i as a Poisson distribution:

$$d_{is} = \text{Poisson}(N_s \pi_i)$$

wherein:
- $d_{is}$ is the determined sequencing depth attributable to the capture probe i;
- $N_s$ is the number of nucleic acid molecules in reference sequencing library s; and
- $\pi_i$ is the binding fraction for capture probe i.

Embodiment 167

The pooled nucleic acid sequencing library of embodiment 166, wherein $\pi_i$ is determined by fitting a maximum likelihood model or a Markov chain Monte Carlo model.

Embodiment 168

The pooled nucleic acid sequencing library of any one of embodiments 149-167, wherein the difference is defined by an objective function of the subsequent amounts of the capture probes in the balanced set of capture probes, according to:

$$f(\vec{v}) = V(\vec{\pi}(\vec{v}))$$

wherein:

$$(\vec{\pi}(\vec{v}))_i = \left(1 + \frac{\gamma_i}{v_i c_i}\right)^{-1}$$

wherein:
- V( ) is a user-defined objective function for the set of capture probes;
- $(\vec{\pi}(\vec{v}))_i$ is the binding fraction for capture probe i for the vector $\vec{\pi}(\vec{v})$;
- $c_i$ is an effective concentration for capture probe i for the vector $\vec{\pi}(\vec{v})$;
- $v_i$ is the subsequent amount of capture probe i for the vector $\vec{\pi}(\vec{v})$; and
- $\gamma_i$ is the initial amount of capture probe i for the vector $\vec{\pi}(\vec{v})$.

Embodiment 169

The pooled nucleic acid sequencing library of any one of embodiments 149-168, wherein the difference is an objective function defined by a coefficient of variation.

Embodiment 170

The pooled nucleic acid sequencing library of any one of embodiments 149-169, further comprising:
- enriching the reference sequencing library using the balanced set of capture probes;
- sequencing the reference sequencing library enriched using the balanced set of capture probes;
- determining a sequencing depth attributable to each capture probe in the balanced set of capture probes;
- selecting a second subsequent known amount of each capture probe based on the subsequent known amount of said capture probe in the balanced set of capture probes and the sequencing depth attributable to said capture probe, wherein the second subsequent known amount of each capture probe is selected to minimize a difference between a second predicted sequencing depth profile and the desired sequencing depth profile; and
- constructing a re-balanced set of capture probes by combining at least a fraction of the capture probes at the second subsequent known amount of each capture probe in the re-balanced set of capture probes.

Embodiment 171

The pooled nucleic acid sequencing library of embodiment 170, wherein minimization of the difference is constrained by a minimum second subsequent amount or a maximum second subsequent amount of each capture probe.

Embodiment 172

The nucleic acid sequencing library of any one of embodiments 149-171, wherein constructing the balanced set of capture probes comprises combining each capture probe in the first set of capture probes at the subsequent known amount of each capture probe in the balanced set capture probe.

Embodiment 173

The nucleic acid sequencing library of any one of embodiments 104-137 or the pooled nucleic acid sequencing library of any one of embodiments 138-172, wherein the nucleic acid inserts are ligated to two sequencing adapters.

Embodiment 174

A method of determining the number of unique nucleic acid molecules in a nucleic acid library, comprising:
- sequencing a set of amplified first strands formed from a first strand of a duplex nucleic acid molecule, resulting in a set of first strand reads;
- compiling the set of first strand reads; and
- counting the number of sets of nucleic acid molecule reads;
- wherein the duplex nucleic acid molecule is ligated to a sequencing adapter prior to being amplified; and the sequencing adapter is randomly selected from a plurality of sequencing adapters comprising a duplex molecular barcode with a predetermined sequence.

Embodiment 175

A method of determining the number of unique nucleic acid molecules in a sequencing library, comprising:
- sequencing a set of amplified first strands formed from a first strand of a duplex nucleic acid molecule, resulting in a set of first strand reads;
- compiling the set of first strand reads; and
- counting the number of sets of nucleic acid molecule reads;
- wherein the duplex nucleic acid molecule is ligated to a sequencing adapter prior to being amplified; and the sequencing adapter is randomly selected from a plurality of sequencing adapters comprising:
  - a first sequencing adapter comprising a first duplex molecular barcode n nucleotides in length; and
  - a second sequencing adapter comprising a second duplex molecular barcode n+x nucleotides in length, wherein x is not zero.

Embodiment 176

A method of determining the number of unique nucleic acid molecules in a sequencing library, comprising:
- sequencing a set of amplified first strands formed from a first strand of a duplex nucleic acid molecule, resulting in a set of first strand reads;
- sequencing a set of amplified second strands formed from a second strand of a duplex nucleic acid molecule, resulting in a set of second strand reads;
- compiling the set of first strand reads;
- compiling the set of second strand reads;

matching the set of first strand reads to the set of second strand reads; and counting the number of matched sets;

wherein the duplex nucleic acid molecule is ligated to a sequencing adapter prior to being amplified; and the sequencing adapter is randomly selected from a plurality of sequencing adapters comprising a duplex molecular barcode with a predetermined sequence.

Embodiment 177

A method of determining the number of unique nucleic acid molecules in a sequencing library, comprising:

sequencing a set of amplified first strands formed from a first strand of a duplex nucleic acid molecule, resulting in a set of first strand reads;

sequencing a set of amplified second strands formed from a second strand of a duplex nucleic acid molecule, resulting in a set of second strand reads;

compiling the set of first strand reads;

compiling the set of second strand reads;

matching the set of first strand reads to the set of second strand reads; and counting the number of matched sets;

wherein the duplex nucleic acid molecule is ligated to a sequencing adapter prior to being amplified; and the sequencing adapter is randomly selected from a plurality of sequencing adapters comprising:

a first sequencing adapter comprising a first duplex molecular barcode n nucleotides in length; and a second sequencing adapter comprising a second duplex molecular barcode n+x nucleotides in length, wherein x is not zero.

EXAMPLES

Example 1

In a first sample, a plurality of sequencing adapters were mixed with a DNA library. The plurality of sequencing adapters included 96 unique molecular barcodes of 12, 13, or 14 nucleotides in length. The sequencing adapters further had a 3'-overhang thymine nucleotide adjacent to the molecular barcode. The nucleic acid molecules in the DNA library were treated such that they had a 3'-overhang adenine nucleotide. The sequencing adapters were ligated to the nucleic acid molecules, amplified, enriched for a region of interest, and sequenced using an Illumina HiSeq2500 sequencer. The total number of bases sequenced was determined, and is present in FIG. 10.

In a second sample, a plurality of sequencing adapters were mixed with a DNA library. The plurality of sequencing adapters included 96 unique molecular barcodes of equal length (12 nucleotides long). The sequencing adapters further had a 3'-overhang thymine nucleotide adjacent to the molecular barcode. The nucleic acid molecules in the DNA library were treated such that they had a 3'-overhang adenine nucleotide. The sequencing adapters were ligated to the nucleic acid molecules, amplified, enriched for a region of interest, and sequenced using an Illumina HiSeq2500 sequencer. The total number of bases sequenced was determined, and is present in FIG. 10.

Figure 10:
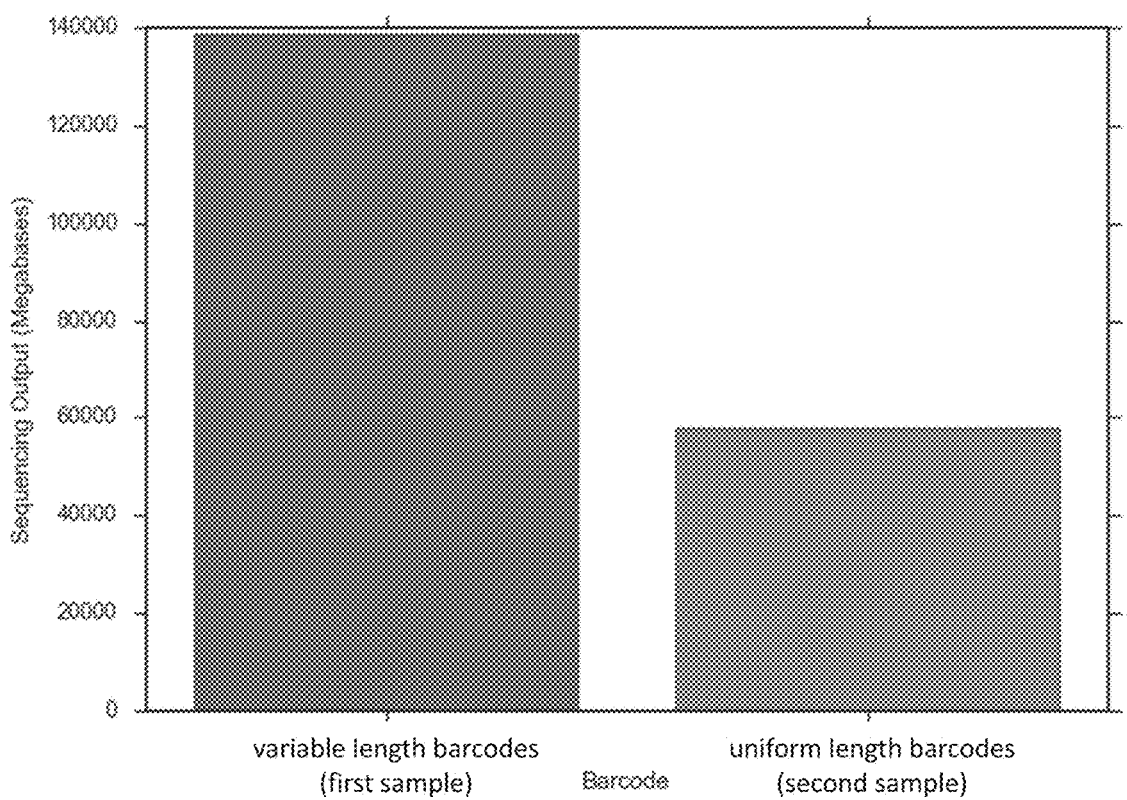
FIG. 10 presents the sequencing output for a DNA library that was sequenced using sequencing adapters with variable length molecular barcodes versus the same DNA library that was sequenced using sequencing adapters with uniform length molecular barcodes.

As illustrated in FIG. 10, use of the variable length molecular barcodes (first sample) resulted in a nearly two-fold increase in sequencing output compared to molecular barcodes of equal length (second sample).

Example 2

A DNA library containing DNA fragments from a healthy individual was combined with a composition comprising 96 unique sequencing adapters with known molecular barcodes 12, 13, or 14 nucleotides in length. The nucleic acid molecules in the DNA sequencing library were amplified, enriched for particular genes of interest, and sequenced using an Illumina HiSeq2500 sequencer. The sequences were then analyzed either by (1) ignoring the molecular barcodes when building a consensus sequence (Sample 1), (2) by ignoring the strand-of-origin of the molecular barcode, thus not comparing to its complement strand, and (3) by comparing the sequenced strand to its original complement strand, thereby correcting for chemical errors.

Figure 11:
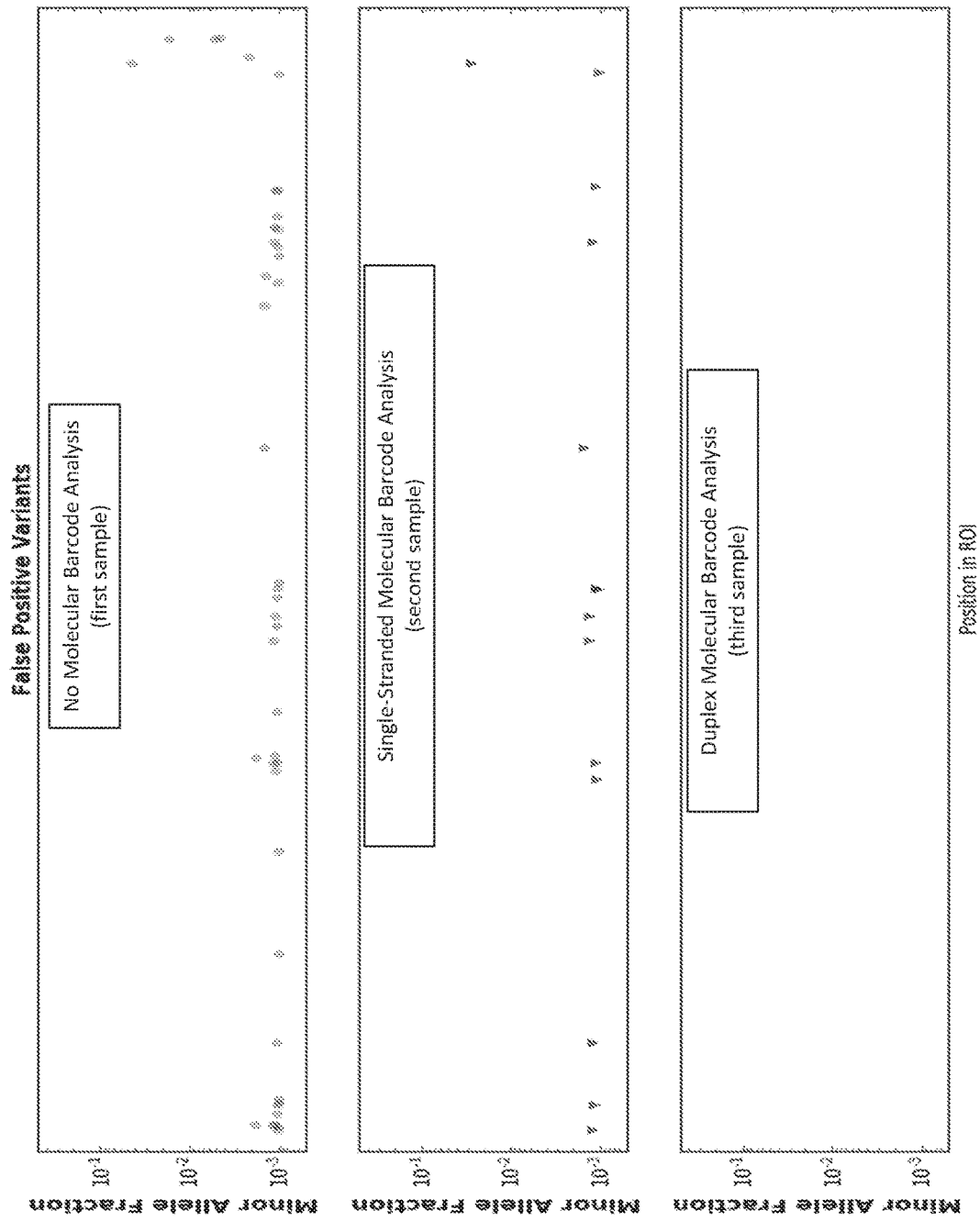
FIG. 11 presents false positive variants that were generated from sequencing a DNA library from a healthy subject. The DNA bound to sequencing adapters as described herein and analyzed either by ignoring the molecular barcodes (first sample), using a single-strand computational analysis by ignoring the strand-of-origin of the molecular barcodes (second sample), and by constructing a consensus sequence that was error-corrected by comparing complement strand sequences (third sample).

Because the DNA library was taken from a healthy individual, any sequencing reads that do not support the genotype were considered errors (i.e., false positive variants) in the sequencing reads. The allele fraction of sequencing reads that do not support the healthy genotype are plotted against the genomic position, and presented in FIG. 11 for each of the three samples.

Figure 12:
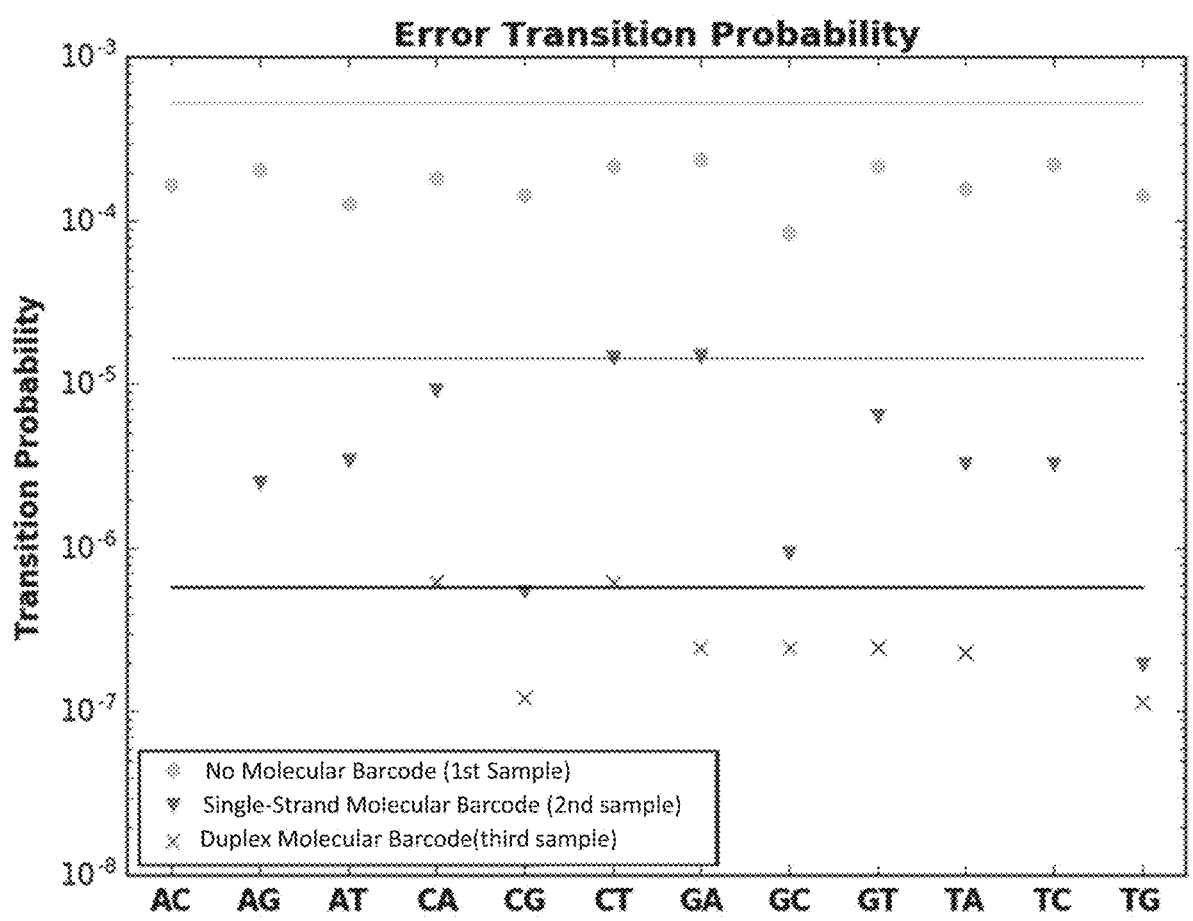
FIG. 12 presents the error transition probability (that is, the probability that a base will be erroneously read as a different base) for a sample using no barcodes, a sample using known molecular barcodes followed by constructing a consensus sequencing using a single-strand computational analysis, and a sample using known molecular barcodes followed by constructing a consensus sequence that was error-corrected by comparing complement strand sequences.

The error rates for individual base-wise error modes (such as an adenine base incorrectly being determined in place of a cytosine base) was also determined for each of the three samples, and is presented in FIG. 12. "AC" indicates bases that should have been adenine, but were incorrectly sequenced as cytosine. This notation is the same for the other error transitions (e.g., AG, AT, CA, CG, CT, etc.). Solid lines indicate the global error rates for all error transitions. Using single-stranded molecular barcode analysis (sample 2) reduces the error rates for most transitions relative to the sample with no molecular barcode analysis (sample 1). Use of duplex molecular barcode analysis (sample 3) further decreases the transition error rate, and some error modes (A to C, A to G, A to T, and T to C) had such low transition error rates that there were no recorded occurrences.

Example 3

Seven unique DNA libraries were separately combined with a composition comprising a plurality of sequencing adapters. The plurality of sequencing adapters had a total of 96 unique molecular barcodes. Additionally, the sequencing adapters included a sample index, which was unique for each of the unique DNA libraries. Thus, each of the seven unique DNA libraries were combined received the same set of 96 molecular barcodes, but a distinct sample index. After the sequencing adapters were combined with the DNA libraries, the sequencing adapters were annealed to the DNA molecules. The DNA libraries were then pooled, amplified, and sequenced.

Figure 13:
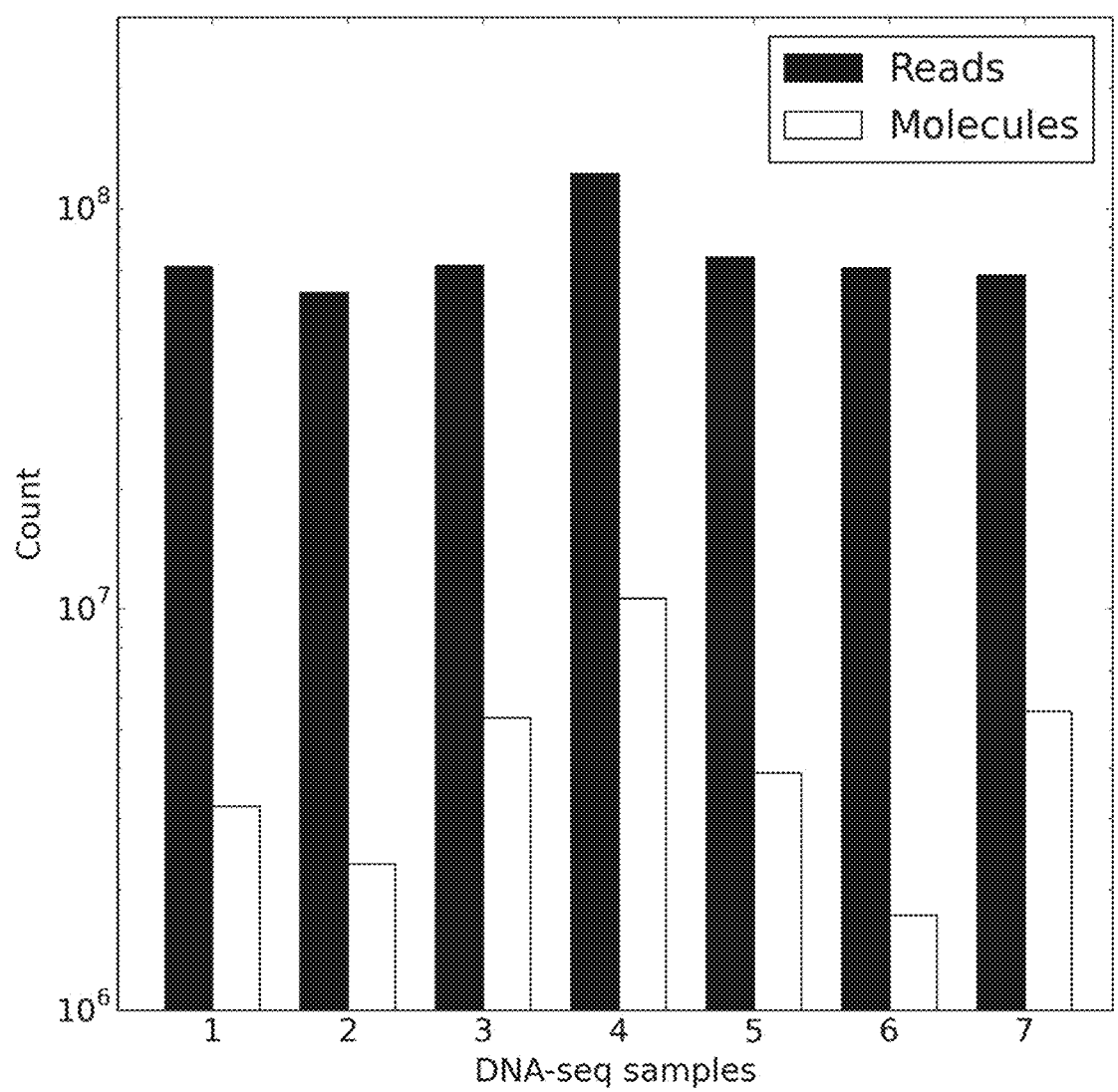
FIG. 13 presents the number of strand reads and the number of original nucleic acid molecules counted in seven separate DNA libraries that were pooled together and jointly sequenced.

The sequencing reads were separated into distinct libraries on the basis of the sample indices. Sets of strand reads were then compiled for each distinct library, and the sets were matched with complementary sets of strand reads. The total number of matched sets in each library represented the number of unique DNA molecules in each of the DNA libraries. The total number of strand reads and the represented number of unique DNA molecules in the original DNA sample library is presented in FIG. 13.

Example 4

To test the sensitivity of the molecular barcodes described herein, a cell line mixture (Horizon Discovery Structural Multiplex Reference Standard—catalog #753) with 49 known single nucleotide polymorphisms (also referred to as "SNPs," "single nucleotide variants", or "SNVs") in the region of interest was sheared and size selected (average fragment size of about 170 base pairs). The fragments resulting from the shearing and size selection simulate cell-free DNA. The fragments were treated such that they had a 3'-overhang adenine nucleotide, and combined with identically processed (i.e., fragmented) health genomic DNA (gDNA) at various concentrations.

Figure 14:
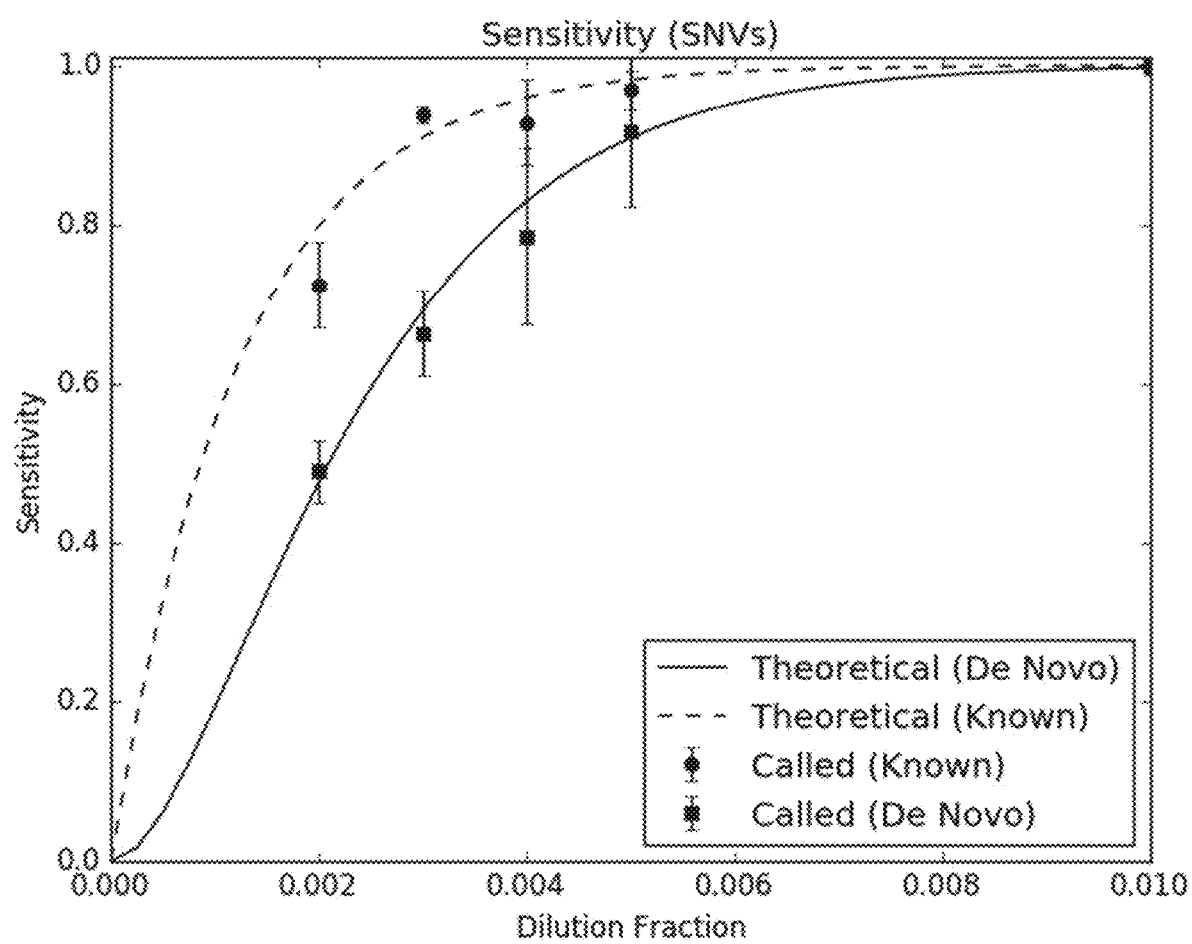
FIG. 14 plots the sensitivity for correctly identifying SNPs in a simulated cell-free DNA that was mixed with healthy, fragmented genomic DNA for various dilution fractions for known or de novo variants using the molecular barcodes and methods described herein.

A plurality of sequencing adapters were mixed with the combined simulated cell-free DNA and fragmented gDNA. The plurality of sequencing adapters included 96 unique molecular barcodes of equal length (12 nucleotides long). The sequencing adapters further had a 3'-overhang thymine nucleotide adjacent to the molecular barcode. The sequencing adapters were ligated to the nucleic acid molecules, amplified, enriched for a region of interest, and sequenced. FIG. 14 plots the sensitivity for correctly identifying SNPs in the simulated cell-free DNA for various dilution fractions for known or de novo variants.

Example 5

A set of capture probes having 583 biotinylated DNA capture probes of 120 bases in length was formed by combining 2.0 uL of each individual capture probe at approximately equimolar concentrations. The set of capture probes was then combined with a healthy cell-free DNA reference sequencing library comprising nucleic acid molecules bound to sequencing adapters (including molecular barcodes). Nucleic acid molecules in the reference sequencing library that hybridized to the capture probes in the set of capture probes were isolated from the non-hybridized nucleic acid molecules, thereby forming the enriched reference sequencing library. The enriched reference sequencing library was PCR amplified and sequenced using an Illumina HiSeq2500 sequencer. Consensus sequences were formed by collapsing all sequencing reads associated with the same molecular barcodes. The sequencing reads were then aligned to the hg19 human genome and the sequencing depth attributable to each capture probe was determined by counting the number of consensus molecules observed that contained at least half of the sequence of the capture probe. The sequencing depth attributable to the capture probes is plotted as a histogram in FIG. 15A, where histogram measures the number of collapsed sequencing reads for each probe with at least 50% overlap with the probe of interest.

The set of capture probes was balanced to minimize the difference between a predicted sequencing depth profile and a uniform desired sequencing depth profile. Minimum capture probe volumes were limited to 0.75 uL and maximum capture probe volumes were limited to 4 uL. To balance the set of capture probes, for each capture probe a binding fraction of the nucleic acid molecules comprising a segment substantially complementary to at least half of the capture probe that bound to the capture probe during enrichment of the sequencing libraries was obtained by approximating the sequencing depth for each capture probe as a Poisson distribution and fitting a maximum likelihood model for the binding fraction. The coefficient of variation (standard deviation divided by the mean) of the predicted sequencing depths was minimized, subject to the aforementioned volume constraints, to determine subsequent volumes for each capture probe. A balanced set of capture probes was constructed using the subsequent volumes for each capture probe. The balanced set of capture probes was used to enrich the reference sequencing library, and the sequencing depths attributable to the capture probes in the balanced capture probe library are shown in FIG. 15B.

Figure 15A:
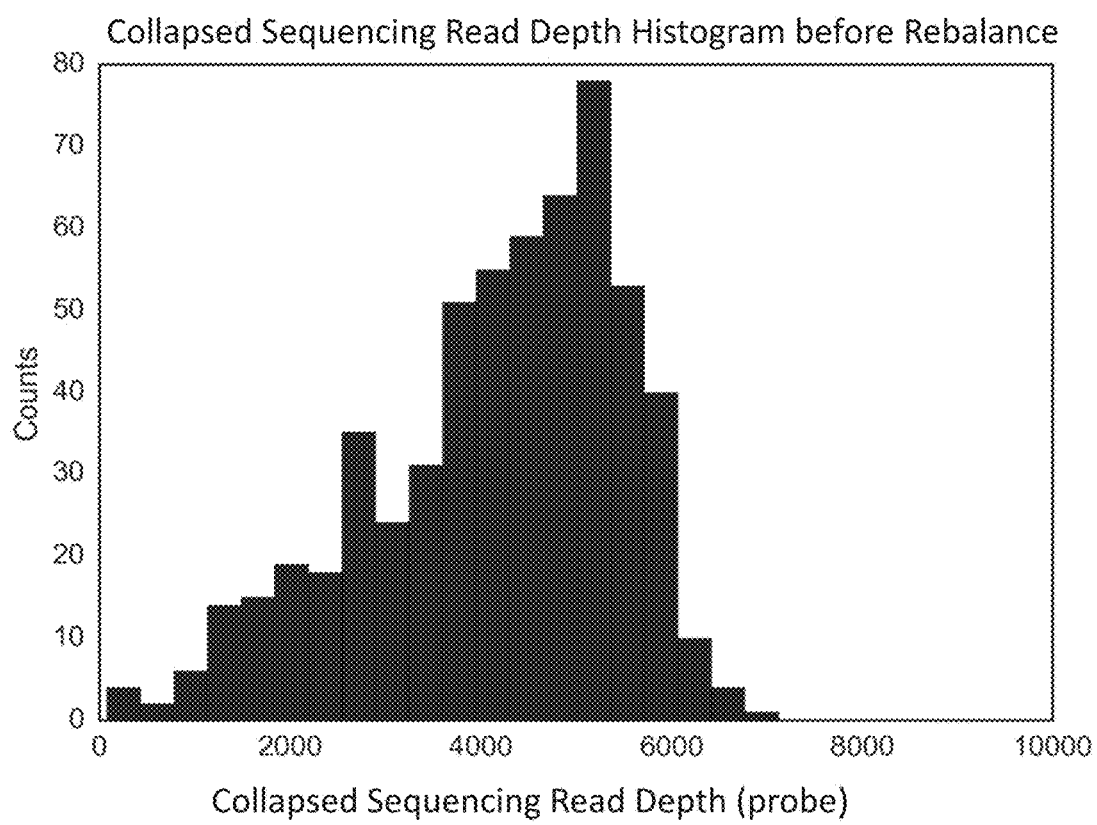
FIG. 15A shows a histogram plotting the number of capture probes in the capture probe library for which a given number of collapsed sequencing reads with at least 50% overlap with a probe can be attributed prior to balancing the capture probe library.
Figure 15B:
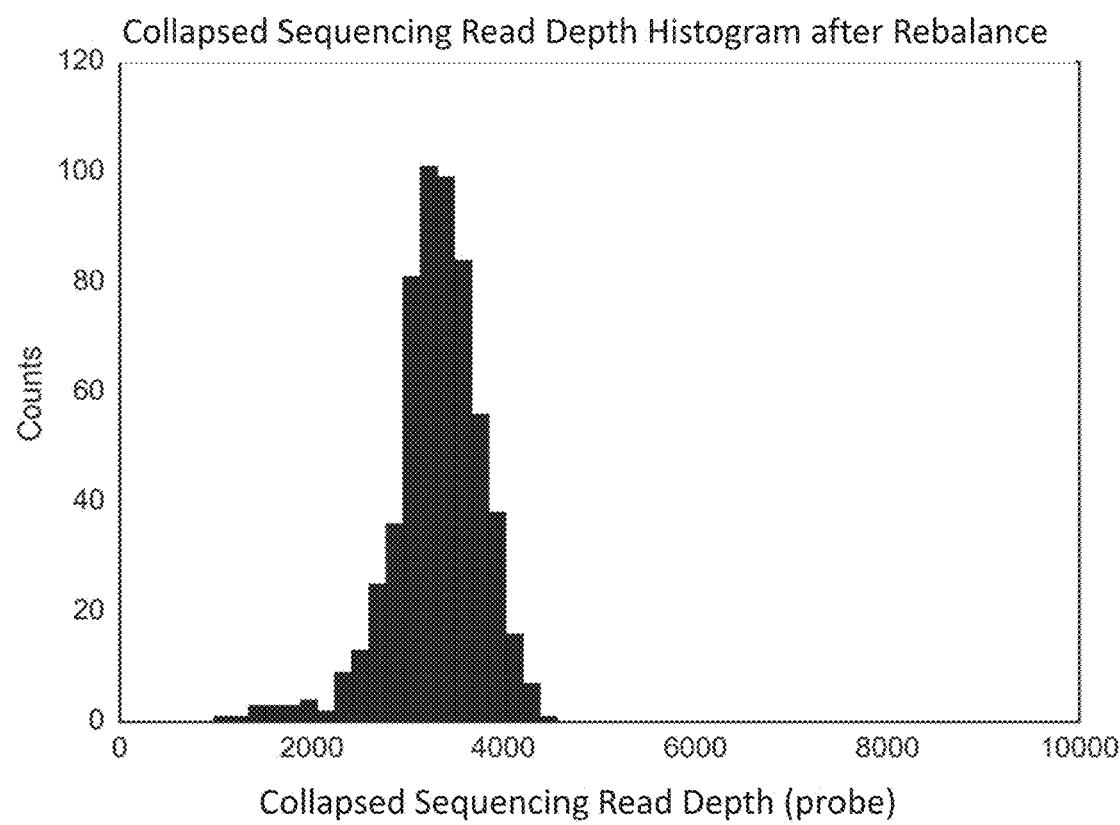
FIG. 15B shows a histogram plotting the number of capture probes in the capture probe library for which a given number of collapsed sequencing reads with at least 50% overlap with a probe can be attributed after to balancing the capture probe library. The capture probes enriched the region of interest by hybridizing to nucleic acid molecules in the sequencing library and isolating the hybridized nucleic acid molecules.
Figure 16A:
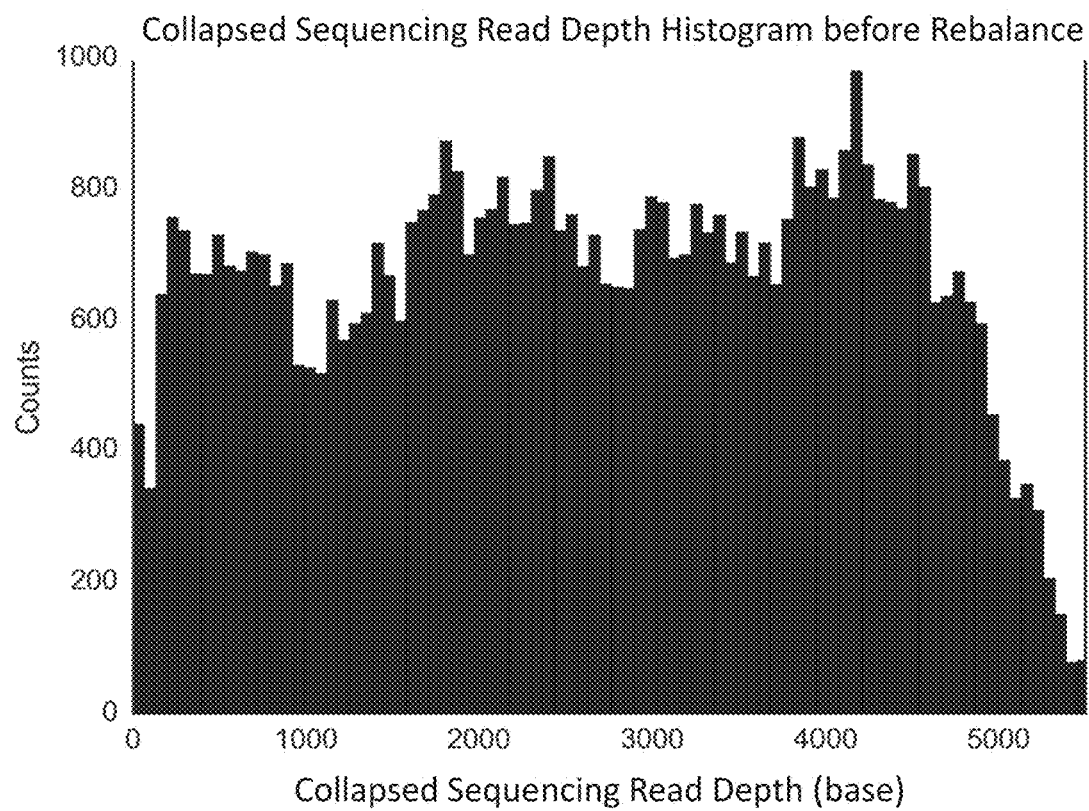
FIG. 16A shows a histogram plotting the number of individual bases in the region of interest that obtained a given number of collapsed sequencing reads prior to balancing the capture probe library.
Figure 16B:
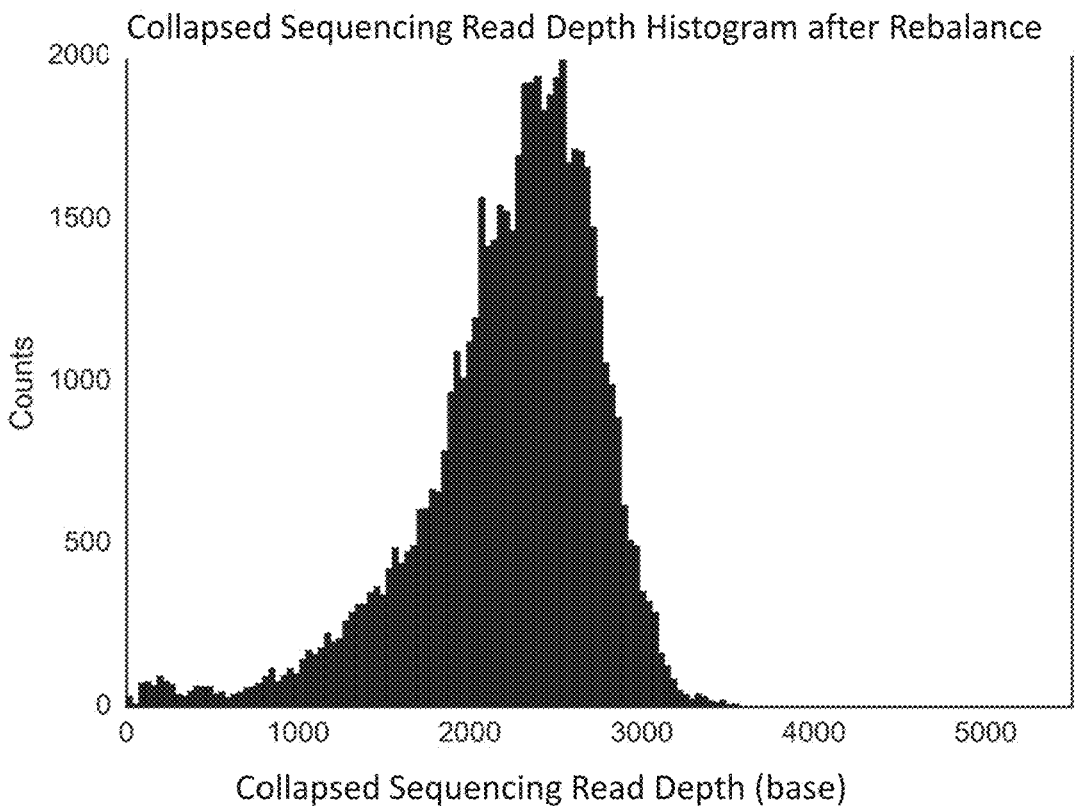
FIG. 16B shows a histogram plotting the number of individual bases in the region of interest that obtained a given number of collapsed sequencing reads after balancing the capture probe library. The capture probes enriched the region of interest by hybridizing to nucleic acid molecules in the sequencing library and isolating the hybridized nucleic acid molecules.

As can be seen in FIG. 15A and FIG. 15B, the rebalanced capture probe library results in a narrower distribution of probe counts. Before balancing, the sequencing depth distribution ranged from 0 to about 7000. After rebalancing, the sequencing depth peaked at 3500, and the number of counts with a sequencing depth under 500 is greatly reduced. The per-base depth profiles, obtained by counting the number of collapsed reads aligning to each base in an approximately 56 kB region of interest, also shows a narrower distribution (FIG. 16A, FIG. 16B).

Example 6

Figure 18:
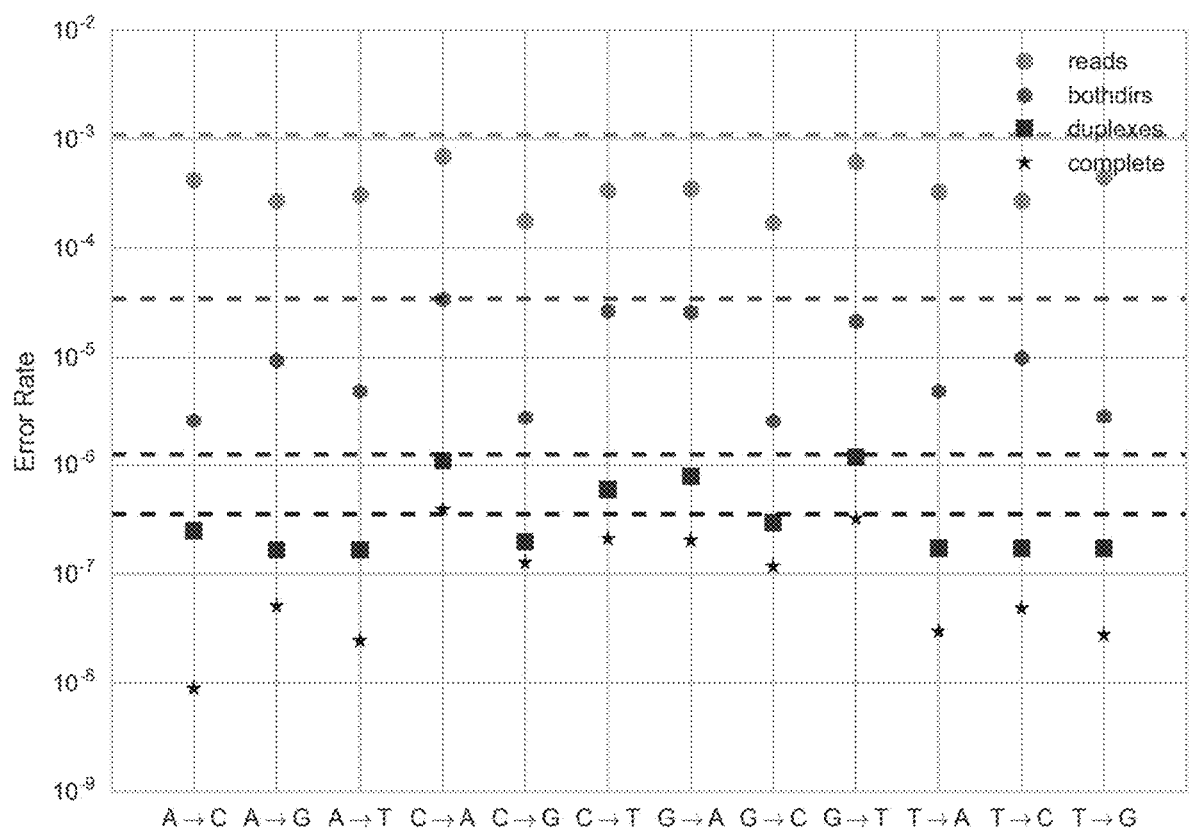
FIG. 18 shows the comparative error rate when sequencing duplex nucleic acid molecules in each of the four modes of sequencing illustrated in FIG. 17A-E. These include sequencing of a single strand in a single direction ("reads"), a single strand in both directions ("bothdirs"), both strands of the duplex nucleic acid molecule with each strand sequenced in a single direction ("duplexes"), and both strands of the duplex nucleic acid molecule with each strand sequenced in both directions ("complete").

Genomic DNA and cell-free DNA samples were taken from 36 healthy individuals. The duplex nucleic acid molecules were ligated to sequencing adapters containing molecular barcodes, amplified, and sequenced. The germline genotypes were estimated and deviations from each sample's genotype were considered as errors. The sequenced fragments were analyzed based on sequencing of a single strand in a single direction ("reads"), a single strand in both directions ("bothdirs"), both strands of the duplex nucleic acid molecule with each strand sequenced in a single direction ("duplexes"), and both strands of the duplex nucleic acid molecule with each strand sequenced in both directions ("complete"). These results are shown in FIG. 18, which shows "reads" giving the highest error, followed by "bothdirs," which is followed by the "duplexes". Sequencing of both strands of the duplex nucleic acid molecule with each strand sequenced in both directions ("complete") showed the lowest error rate for all mutation types.

What is claimed is:
1. A method of sequencing a nucleic acid molecule, comprising:
(i) mixing a plurality of sequencing adaptors comprising at least a first sequence adaptor and a second sequence adaptor with a duplex nucleic acid molecule;
(ii) ligating the first sequence adapter and the second sequence adapter to the duplex nucleic acid molecule prior to amplification of the duplex nucleic acid molecule,
wherein the first sequence adapter is a U-shaped sequence adapter or a Y-shaped sequence adapter, and
wherein the first sequence adapter comprises a first duplex molecular barcode consisting of n base positions and a predetermined base fraction at one or more base positions across a plurality of duplex molecular barcodes,
wherein n is between 8 and 16,
wherein the second sequence adapter is a U-shaped sequence adapter or a Y-shaped sequence adapter, and
wherein the second sequence adapter comprises a second duplex molecular barcode consisting of n+x base positions and a predetermined base fraction at one or more base positions across the plurality of duplex molecular barcodes,
wherein n is between 8 and 16 and x is 1,
wherein the second duplex molecular barcode has more base positions than the first duplex molecular barcode, and
wherein the sequence adapters in the plurality of sequence adapters each comprise a first constant

3'-overhang comprising a thymine residue directly adjacent to the duplex molecular barcode, and wherein for each duplex molecular barcode other than the first duplex molecular barcode a thymine residue does not immediately precede the first constant 3'-overhang of each sequence adapter;

(iii) amplifying a first strand of the duplex nucleic acid molecule;

(iv) sequencing a set of amplified first strands formed from the first strand of the duplex nucleic acid molecule, resulting in a set of first strand reads; and (v) constructing a first strand consensus sequence using the set of first strand reads.

2. The method of claim 1, wherein the plurality of sequencing adapters further comprises a third sequencing adapter comprising a third duplex molecular barcode consisting of n+y base positions, wherein n is between 8 and 16 and y is not zero or x, and wherein the third duplex molecular barcode has more base positions than the first duplex molecular barcode.

3. The method of claim 1, further comprising compiling the set of first strand reads.

4. The method of claim 3, wherein the set of first strand reads is compiled based on sequence distance or alignment to a reference sequence.

5. The method of claim 1, wherein constructing the first strand consensus sequence comprises:

comparing the first strand reads in the set of first strand reads;

identifying and removing errors in the set of first strand reads; and constructing an error-corrected first-strand consensus sequence.

6. The method of claim 1, wherein constructing the first strand consensus sequence comprises:

constructing a first strand consensus sequence from the set of first strand reads;

comparing the first strand consensus sequence to the set of first strand reads;

identifying and removing errors in the set of first strand reads; and constructing an error-corrected first strand consensus sequence.

7. The method of claim 1, wherein the first strand is sequenced in a first direction and a second direction.

8. The method of claim 1, further comprising:

amplifying a second strand of the duplex nucleic acid molecule in the amplification step to form amplified second strands;

sequencing a set of amplified second strands formed from a second strand of the duplex nucleic acid molecule, resulting in a set of second strand reads; and constructing a second strand consensus sequence using the set of second strand reads.

9. The method of claim 8, wherein the second strand is sequenced in a first direction and a second direction.

10. The method of claim 8, further comprising compiling the set of second strand reads.

11. The method of claim 8, further comprising compiling the set of second strand reads based on sequence distance or alignment to a reference sequence.

12. The method of claim 8, further comprising:

comparing the first strand consensus sequence and the second strand consensus sequence;

identifying and removing errors in the set of first strand reads and the set of second strand reads; and constructing an error-corrected duplex consensus sequence.

13. The method of claim 1, wherein the duplex nucleic acid molecule comprises a second constant 3'-overhang complementary to the first constant 3'-overhang.

14. The method of claim 1, wherein the ratio of A/C to G/T nucleotides at any given position of each duplex molecular barcode is between about 2:1 and about 1:2 at the corresponding position relative to the length of the shortest duplex molecular barcode in the plurality of sequencing adapters.

15. The method of claim 1, wherein the predetermined base fraction comprises between 0.2 and 0.4 for each of adenine, cytosine, thymine, and guanine.

16. The method of claim 1, wherein each duplex molecular barcode comprises an edit distance of 2 or more from another duplex molecular barcode and wherein said edit distance is the minimum number of single-base changes that two or more sequences must undergo to result in identity between the sequences.

17. The method of claim 1, wherein each sequencing adapter comprises a sample index nucleic acid sequence, and where:

the proportion of adenine within the sample index nucleic acid sequence is between 0.2 and 0.4;

the proportion of cytosine within the sample index nucleic acid sequence is between 0.2 and 0.4;

the proportion of thymidine within the sample index nucleic acid sequence is between 0.2 and 0.4; and the proportion of guanine within the sample index nucleic acid sequence is between 0.2 and 0.4.

18. The method of claim 1, wherein the duplex nucleic acid molecule is a cell-free DNA molecule.

19. The method according to claim 1, wherein the duplex nucleic acid molecule is enriched from a nucleic acid library using a set of capture probes for a region of interest, and wherein the set of capture probes is balanced to provide a reduced sequencing depth variance relative to a set of capture probes comprising a plurality of approximately equally represented capture probes.

* * * * *